(12) United States Patent
Kim et al.

(10) Patent No.: US 11,649,225 B2
(45) Date of Patent: *May 16, 2023

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Chi-Sik Kim, Gyeonggi-do (KR); Kyoung-Jin Park, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 313 days.

This patent is subject to a terminal disclaimer.

(21) Appl. No.: 16/651,393

(22) PCT Filed: Oct. 23, 2018

(86) PCT No.: PCT/KR2018/012546
§ 371 (c)(1),
(2) Date: Mar. 27, 2020

(87) PCT Pub. No.: WO2019/083248
PCT Pub. Date: May 2, 2019

(65) Prior Publication Data
US 2020/0299274 A1     Sep. 24, 2020

(30) Foreign Application Priority Data

Oct. 27, 2017 (KR) .................. 10-2017-0140855
Oct. 12, 2018 (KR) .................. 10-2018-0122069

(51) Int. Cl.
| | | |
|---|---|---|
| *C07D 403/12* | (2006.01) | |
| *C07D 403/14* | (2006.01) | |
| *C07D 405/14* | (2006.01) | |
| *C07D 409/14* | (2006.01) | |
| *H01L 51/50* | (2006.01) | |
| *C09K 11/06* | (2006.01) | |
| *H01L 51/00* | (2006.01) | |

(52) U.S. Cl.
CPC ......... *C07D 403/12* (2013.01); *C07D 403/14* (2013.01); *C07D 405/14* (2013.01); *C07D 409/14* (2013.01); *H01L 51/0061* (2013.01); *H01L 51/0067* (2013.01); *H01L 51/0072* (2013.01); *H01L 51/0073* (2013.01); *H01L 51/0074* (2013.01)

(58) Field of Classification Search
CPC .. C07D 403/12; C07D 403/14; C07D 405/14; C07D 409/14; H01L 51/0061; H01L 51/0067; H01L 51/0072; H01L 51/0073; H01L 51/0074; H01L 51/50; C09K 11/06; C09K 2211/1029; C09K 2211/1033; C09K 2211/1037; C09K 2211/1044; C09K 2211/1048; C09K 2211/1051
See application file for complete search history.

(56) References Cited

U.S. PATENT DOCUMENTS

| 8,227,798 B2 | 7/2012 | Kai et al. | |
|---|---|---|---|
| 2017/0098778 A1* | 4/2017 | Oh | ...................... C07D 251/24 |
| 2022/0181558 A1* | 6/2022 | Jun | ...................... C07D 251/24 |

FOREIGN PATENT DOCUMENTS

| KR | 2015-0001101 A | 1/2015 |
|---|---|---|
| KR | 2015-0006199 A | 1/2015 |
| WO | 2015041428 A1 | 3/2015 |

* cited by examiner

*Primary Examiner* — Sun Jae Yoo
(74) *Attorney, Agent, or Firm* — G. Creston Campbell

(57) ABSTRACT

The present disclosure relates to an organic electroluminescent compound and an organic electroluminescent device comprising the same. The organic electroluminescent device having a low driving voltage and/or a high luminous efficiency and/or a long lifespan can be provided, by comprising an organic electroluminescent compound according to the present disclosure.

3 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound that can be used in an organic electroluminescent device (OLED) field and an organic electroluminescent device comprising the same

BACKGROUND ART

An organic electroluminescent device (OLED) changes electric energy into light by the injection of a charge into an organic light-emitting material, and commonly comprises an anode, a cathode, and an organic layer formed between the two electrodes. The organic layer of the organic electroluminescent device may be composed of a hole injection layer, a hole transport layer, a hole auxiliary layer, a light-emitting auxiliary layer, an electron blocking layer, a light-emitting layer (containing host and dopant materials), an electron buffer layer, a hole blocking layer, an electron transport layer, an electron injection layer, etc., as necessary.

The light-emission mechanism of the organic electroluminescent device is as follows. A hole injected from an anode to the valance band (Highest Occupied Molecular Orbital: HOMO) of a hole injection layer (HIL) moves to a light-emitting layer through a hole transport layer (HTL). At the same time, an electron moves from a cathode to a light-emitting layer through an electron injection layer to form excitons by combination with the holes. The exciton emits lights as it returns to the ground state.

Using this principle of such an organic electroluminescent device, the first organic electroluminescent device was developed by Eastman Kodak in 1987, by using TPD (N,N'-Diphenyl-N,N'-bis(methylphenyl)-(1,1'-biphenyl)-4,4'-diamine) as a hole transport layer and $Alq_3$ (tris(8-hydroxyquinoline) aluminium complex) as a light-emitting layer (see Appl. Phys. Lett. 51, 913, 1987).

The most important factor determining luminous efficiency in an organic electroluminescent device is light-emitting materials. The light-emitting materials are required to have the following features: high quantum efficiency, high movement degree of an electron and a hole, and uniformity and stability of the formed light-emitting material layer. The light-emitting material is classified into blue, green, and red light-emitting materials according to the light-emitting color, and further includes yellow or orange light-emitting materials.

Meanwhile, when only one compound is used as a light-emitting material, there arises the problem that the maximum light-emission wavelength shifts to a long wavelength due to intermolecular interaction and the color purity decreases, or the efficiency of the device decreases due to the light-emission attenuating effect. Thus, a host/dopant system can be used as a light-emitting material in order to increase luminous efficiency and stability through increasing color purity and energy transfer.

The principle is that when a dopant having excellent luminous efficiency and a smaller energy band gap than a host mainly constituting the light-emitting layer is mixed in the light-emitting layer in a small amount, excitons generated in the host move into the dopant, so that light is emitted with high efficiency. Wherein, the wavelength of the host moves into the wavelength band of the dopant, so that light of the desired wavelength can be obtained according to the type of dopant to be used.

Conventionally, a co-host has been used which simultaneously uses a hole transporting host and an electron transporting host as a phosphorescence green host (PGH), and wherein carbazole or arylamine, having a fast hole mobility, has been used as the hole transporting host (KR 1474232 B1). However, when the arylamine, having a high hole mobility, is used as the PGH, there has been a problem in that it is not suitable as a hole transporting host since a side reaction, as described below, occurs.

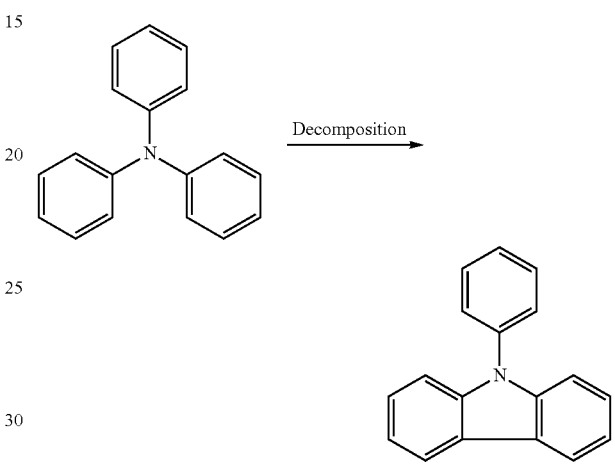

DISCLOSURE OF INVENTION

Technical Problem

The object of the present disclosure is to provide an organic electroluminescent compound capable of firstly producing an organic electroluminescent device having a low driving voltage and/or a high luminous efficiency and/or a long lifespan, and secondly, to provide the organic electroluminescent device comprising the organic electroluminescent compound.

Solution to Problem

As a result of intensive studies to solve the technical problem above, the present inventors solved the problem of arylamine being the hole transporting host used as the conventional phosphorescence green host by introducing a heteroaryl group not having α-Hydrogen, such as pyridine or pyrimidine, which is able to reduce the reactivity of a non-covalent electron pair possessed by an amine. Particularly, the present inventors found that when an organic electroluminescent compound according to one embodiment is used as a light-emitting material by introducing a substituent to the 5-position carbon of pyridine or pyrimidine, being the central core, the aforementioned conventional side reaction does not occur and the organic electroluminescent compound has a high LUMO level and excellent hole mobility. Consequently, the organic electroluminescent compound according to one embodiment can provide an organic electroluminescent device having a low driving voltage and/or a high luminous efficiency and/or a long lifespan.

More specifically, the above objective can be achieved through the organic electroluminescent compound represented by the following formula 1:

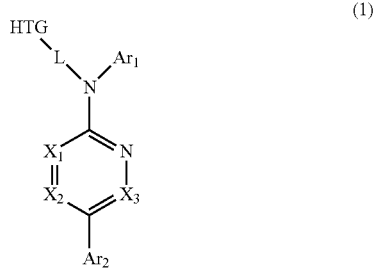

wherein, $X_1$ to $X_3$ each independently represent N or CH;

$Ar_1$ and $Ar_2$ each independently represent a substituted or unsubstituted (C6-C30)aryl or a substituted or unsubstituted (3- to 30-membered)heteroaryl; or may be linked to an adjacent substituent to form a substituted or unsubstituted, (C3-C30) mono- or polycyclic, alicyclic or aromatic ring, or the combination thereof;

L represents a single bond, a substituted or unsubstituted (C6-C30)arylene, or a substituted or unsubstituted (3- to 30-membered)heteroarylene;

HTG represents a substituted or unsubstituted (3- to 30-membered)heteroaryl;

and when L represents a single bond, $Ar_1$ may be linked to HTG to form a mono- or polycyclic ring.

Advantageous Effects of Invention

The organic electroluminescent device having a low driving voltage and/or a high luminous efficiency and/or a long lifespan can be prepared, by comprising an organic electroluminescent compound according to the present disclosure.

MODE FOR THE INVENTION

Hereinafter, the present disclosure will be described in detail. However, the following description is intended to explain the invention, and is not meant in any way to restrict the scope of the invention.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material, etc.

The organic electroluminescent material in the present disclosure may comprise at least one compound represented by the following formula 1. For example, the compound represented by the following formula 1 may be comprised in the light-emitting layer, and when being comprised in the light-emitting layer, the compound of formula 1 may be comprised as a host, more specifically as a phosphorescence green host.

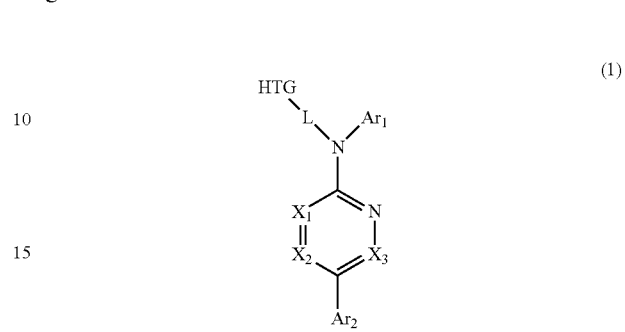

The compound represented by formula 1 above will be described in more detail, as follows.

In formula 1, $X_1$ to $X_3$ each independently represent N or CH; preferably, $X_1$ represents N, and $X_2$ and $X_3$ represent CH; or $X_1$ to $X_3$ may all be CH.

In formula 1, $Ar_1$ and $Ar_2$ each independently represent a substituted or unsubstituted (C6-C30)aryl or a substituted or unsubstituted (3- to 30-membered)heteroaryl; or may be linked to an adjacent substituent to form a substituted or unsubstituted, (C3-C30) mono- or polycyclic, alicyclic or aromatic ring, or the combination thereof; preferably, may be a substituted or unsubstituted (C6-C25)aryl or a substituted or unsubstituted (5- to 25-membered)heteroaryl; or may be linked to an adjacent substituent to form a substituted or unsubstituted, (C5-C25) mono- or polycyclic, alicyclic or aromatic ring; more preferably, may be an unsubstituted (C6-C18)aryl or an unsubstituted (5- to 18-membered)heteroaryl; or may be linked to an adjacent substituent to form a substituted or unsubstituted (C5-C18) mono- or polycyclic, alicyclic or aromatic ring.

In one embodiment, $Ar_1$ and $Ar_2$ of formula 1 each independently may be a substituted or unsubstituted phenyl, a substituted or unsubstituted biphenyl, a substituted or unsubstituted terphenyl, a substituted or unsubstituted naphthyl, a substituted or unsubstituted fluorenyl, a substituted or unsubstituted dibenzofuranyl, a substituted or unsubstituted dibenzothiophenyl, or a substituted or unsubstituted carbazolyl.

In one embodiment, $Ar_2$ of formula 1 may be linked to an adjacent substituent, i.e., central core, to form a substituted or unsubstituted [1]benzofuro[2,3-d]pyrimidine or a substituted or unsubstituted 9H-Pyrimido[4,5-b]indole.

In formula 1, L represents a single bond, a substituted or unsubstituted (C6-C30)arylene, or a substituted or unsubstituted (3- to 30-membered)heteroarylene; preferably, may be a single bond, a substituted or unsubstituted (C6-C25) arylene, or a substituted or unsubstituted (5- to 25-membered)heteroarylene; more preferably, may be a single bond, an unsubstituted (C6-C18)arylene, or an unsubstituted (5- to 18-membered)heteroarylene.

In one embodiment, L of formula 1 may be a single bond, a substituted or unsubstituted phenylene, or a substituted or unsubstituted carbazolene.

In formula 1, HTG represents a hole transporting group such as a substituted or unsubstituted (3- to 30-membered) heteroaryl which is electron-rich; preferably, may be a substituted or unsubstituted (5- to 25-membered)heteroaryl;

more preferably, may be a (5- to 18-membered)heteroaryl, e.g., the heteroaryl may contain at least one heteroatom selected from N, O, and S.

In one embodiment, the HTG may be represented by any one of the following formulae 1-1 to 1-4, but is not limited thereto.

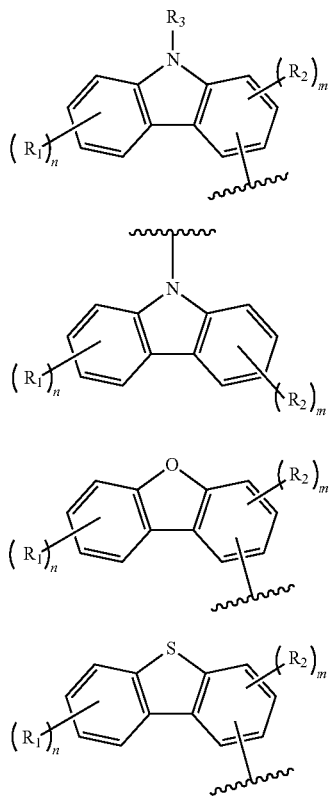

In formulae 1-1 to 1-4,

♦♦♦ means a linkage with L of formula 1, $R_1$ to $R_3$ each independently represent hydrogen, deuterium, halogen, cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or may be linked to an adjacent substituent to form a substituted or unsubstituted (C3-C30) mono- or polycyclic, alicyclic or aromatic ring;

n and m each independently represent an integer of 1 to 4, provided that, in formulae 1-1, 1-3, and 1-4, m represents an integer of 1 to 3.

In formulae 1-1 to 1-4, $R_1$ to $R_3$ each independently may be hydrogen, a substituted or unsubstituted (C6-C30)aryl, or a substituted or unsubstituted (3- to 30-membered)heteroaryl; preferably, may be hydrogen, a substituted or unsubstituted (C6-C25)aryl, or a substituted or unsubstituted (3- to 25-membered)heteroaryl; more preferably, may be hydrogen, a substituted or unsubstituted (C6-C18)aryl, or a substituted or unsubstituted (3- to 18-membered)heteroaryl.

In one embodiment, in formulae 1-1 to 1-4, $R_1$ to $R_3$ each independently may be hydrogen, a substituted or unsubstituted phenyl, a substituted or unsubstituted m-biphenyl, a substituted or unsubstituted p-biphenyl, a substituted or unsubstituted naphthyl, a substituted or unsubstituted dibenzofuranyl, or a substituted or unsubstituted dibenzothiophenyl.

Specifically, the compounds of formulae 1-1 and 1-2 may be represented by any one of the following formulae I-1 to I-3, but are not limited thereto.

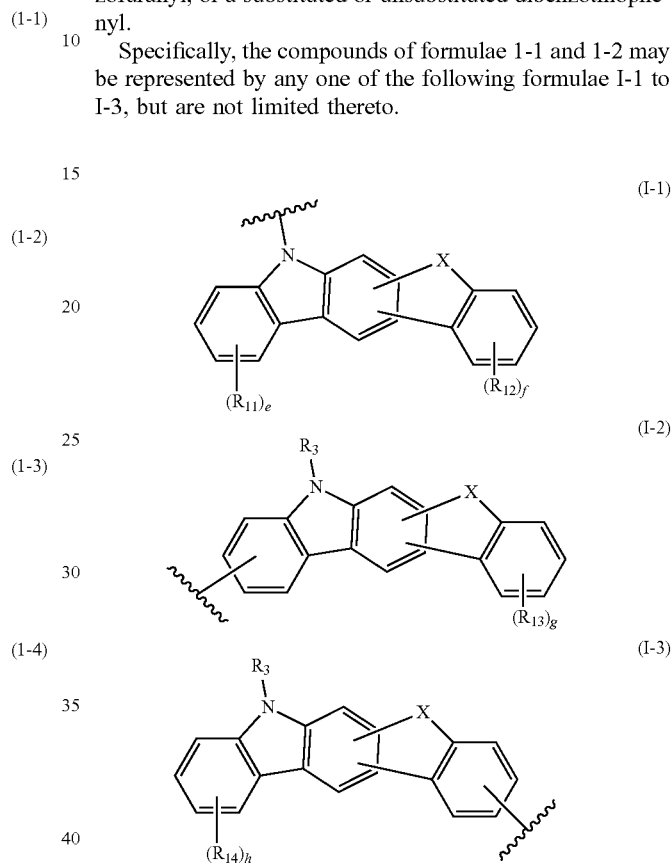

In formulae I-1 to I-3,

♦♦♦ means a linkage with L of formula 1,

X represents O, S, or $NR_4$; preferably, X may be O or $NR_4$.

$R_3$, $R_4$, and $R_{11}$ to $R_{14}$ each independently represent hydrogen, deuterium, halogen, cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; or may be linked to an adjacent substituent to form a substituted or unsubstituted (C3-C30) mono- or polycyclic, alicyclic or aromatic ring;

e, f, g, and h each independently represent an integer from 1 to 4.

In one embodiment, $R_3$ and $R_4$ each independently may be a substituted or unsubstituted (C6-C30)aryl; preferably, may be a substituted or unsubstituted (C6-C25)aryl; more preferably, may be a substituted or unsubstituted (C6-C18)aryl. For example, $R_3$ and $R_4$ may be phenyl.

In formula 1, when L is a single bond, Ar₁ may be linked with HTG to form a mono- or polycyclic ring; preferably, Ar₁ may be linked with HTG to form a substituted or unsubstituted indolocarbazole.

In one embodiment, when the Ar₁ and HTG are linked to each other to form a mono- or polycyclic ring, the compound of formula 1 may be represented by the following formula 2, but is not limited thereto.

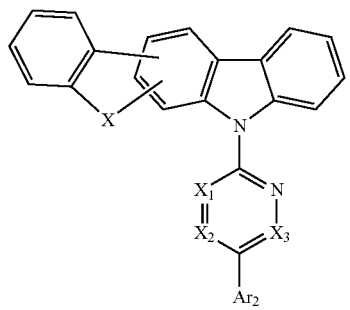

(2)

In formula 2,

X represents O, S, or NR₄;

X₁ to X₃ each independently represent N or CH;

Ar₂ represents a substituted or unsubstituted (C6-C30)aryl or a substituted or unsubstituted (3- to 30-membered)heteroaryl;

R₄ represents hydrogen, deuterium, halogen, cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; or may be linked to an adjacent substituent to form a substituted or unsubstituted (C3-C30) mono- or polycyclic, alicyclic or aromatic ring.

In formula 2, X may be NR₄.

In one embodiment, the compound of formula 2 may be represented by any one of the following formulae 2-1 to 2-6, but is not limited thereto.

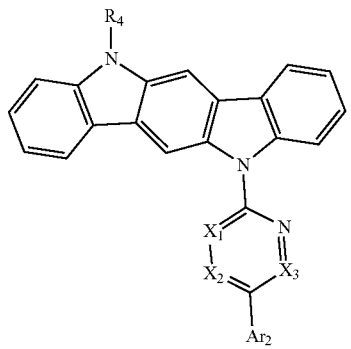

(2-1)

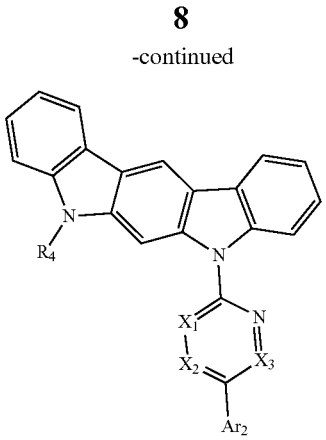

(2-2)

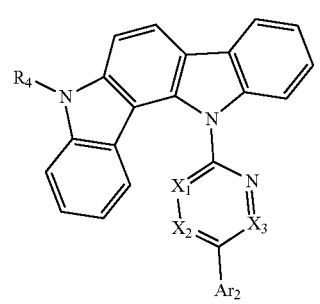

(2-3)

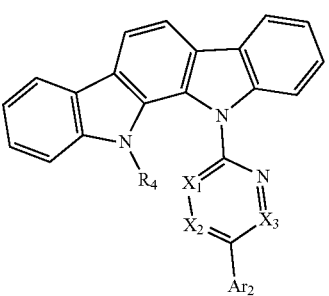

(2-4)

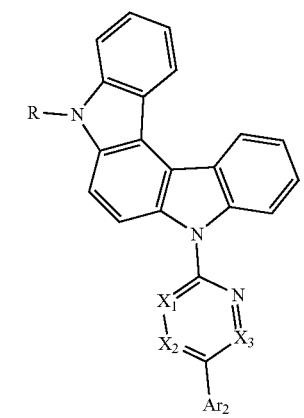

(2-5)

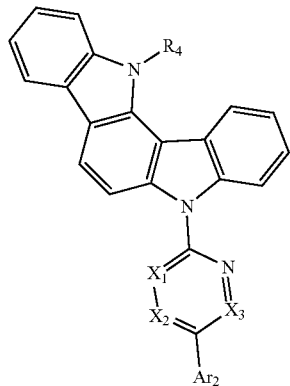

(2-6)

In formulae 2-1 to 2-6, $X_1$ to $X_3$, $R_4$, and $Ar_2$ are as defined in formula 2.

In formula 2, $Ar_2$ represents a substituted or unsubstituted (C6-C30)aryl or a substituted or unsubstituted (3- to 30-membered)heteroaryl; preferably, may be a substituted or unsubstituted (C6-C25)aryl; more preferably, may be a substituted or unsubstituted (C6-C18)aryl.

In one embodiment, $Ar_2$ of formula 2 may be a substituted or unsubstituted phenyl or a substituted or unsubstituted biphenyl.

In formula 2, $R_4$ may be a substituted or unsubstituted (C6-C30)aryl or a substituted or unsubstituted (3- to 30-membered)heteroaryl; preferably, may be a substituted or unsubstituted (C6-C25)aryl, or a substituted or unsubstituted (5- to 25-membered)heteroaryl; more preferably, may be a substituted or unsubstituted (C6-C18)aryl or a substituted or unsubstituted (5- to 18-membered)heteroaryl.

In one embodiment, $R_4$ of formula 2 may be a substituted or unsubstituted phenyl or a substituted or unsubstituted biphenyl.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, and tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is a cycloalkyl having 3 to 7 ring backbone atoms, preferably 5 to 7 ring backbone atoms and at least one heteroatom selected from the group consisting of B, N, O, S, Si, and P, preferably O, S, and N, and includes tetrahydrofuran, pyrrolidine, thiolan, tetrahydropyran, etc. "(C6-C30)aryl(ene)" is a monocyclic or fused ring radical derived from an aromatic hydrocarbon having 6 to 30 ring backbone carbon atoms and may be partially saturated, in which the number of ring backbone carbon atoms is preferably 6 to 25, more preferably 6 to 18. The aryl includes those having a spiro structure, and includes phenyl, biphenyl, terphenyl, naphthyl, binaphthyl, phenylnaphthyl, naphthylphenyl, phenyl terphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "(3- to 30-membered) heteroaryl(ene)" is an aryl group having at least one heteroatom selected from the group consisting of B, N, O, S, Si, and P, and 3 to 30 ring backbone atoms; having preferably 1 to 4 heteroatoms, and may be a monocyclic ring, or a fused ring condensed with at least one benzene ring; may be partially saturated. In addition, the heteroaryl(ene) in the present disclosure may be one formed by linking at least one heteroaryl or aryl group to a heteroaryl group via a single bond(s); may comprise those having a spiro structure; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, di benzocarbazolyl, phenoxazinyl, phenothiazinyl, phenanthridinyl, benzodioxolyl, dihydroacridinyl, etc. "Halogen" includes F, Cl, Br, and I.

In addition, "substituted" in the expression "substituted or unsubstituted" means that a hydrogen atom in a certain functional group is replaced with another atom or functional group, i.e., a substituent. The substituents of the substituted (C1-C30)alkyl, the substituted (C2-C30)alkenyl, the substituted (C2-C30)alkynyl, the substituted (C6-C30)aryl(ene), the substituted (3- to 30-membered)heteroaryl(ene), the substituted (C3-C30)cycloalkyl, the substituted (C1-C30) alkoxy, the substituted tri(C1-C30)alkylsilyl, the substituted di(C1-C30)alkyl(C6-C30)arylsilyl, the substituted (C1-C30) alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C1-C30)alkyl(C6-C30)arylamino, and the substituted (C3-C30) mono- or polycyclic, alicyclic, aromatic ring, or the combination thereof, in formulae 1, 1-1 to 1-4, I-1 to I-3, 2, and 3 are each independently at least one selected from the group consisting of deuterium; halogen; cyano; carboxyl; nitro; hydroxy; (C1-C30)alkyl; halo(C1-C30)alkyl; (C2-C30)alkenyl; (C2-C30)alkynyl; (C1-C30)alkoxy; (C1-C30) alkylthio; (C3-C30)cycloalkyl; (C3-C30)cycloalkenyl; (3- to 7-membered)heterocycloalkyl; (C6-C30)aryloxy; (C6-C30)arylthio; (3- to 30-membered)heteroaryl-substituted or unsubstituted (C6-C30)aryl; (C6-C30)aryl-substituted or unsubstituted (3- to 30-membered)heteroaryl; tri(C1-C30) alkylsilyl; tri(C6-C30)arylsilyl; di(C1-C30)alkyl(C6-C30) arylsilyl; (C1-C30)alkyldi(C6-C30)arylsilyl; amino; a mono- or di-(C1-C30)alkylamino; a mono- or di-(C6-C30) arylamino; (C1-C30)alkyl(C6-C30)arylamino; (C1-C30)alkylcarbonyl; (C1-C30)alkoxycarbonyl; (C6-C30)arylcarbonyl; di(C6-C30)arylboronyl; di(C1-C30)alkylboronyl; (C1-C30)alkyl(C6-C30)arylboronyl; (C6-C30)ar(C1-C30)alkyl; and (C1-C30)alkyl(C6-C30)aryl; preferably, (C1-C20)alkyl, (5- to 25-membered)heteroaryl-substituted or unsubstituted (C6-C25)aryl, or (C6-C25)aryl-substituted or unsubstituted (5- to 25-membered)heteroaryl; more preferably, (C1-C10)alkyl, (5- to 18-membered)heteroaryl-substituted or unsubstituted (C6-C18)aryl or unsubstituted (5- to 8-membered)heteroaryl, e.g., the substituent may be methyl, phenyl, biphenyl, naphthyl, dibenzothiophenyl, or dibenzofuranyl, etc.

Specifically, the organic electroluminescent compound represented by formula 1 may be represented by the following compounds, but is not limited thereto:

C-1

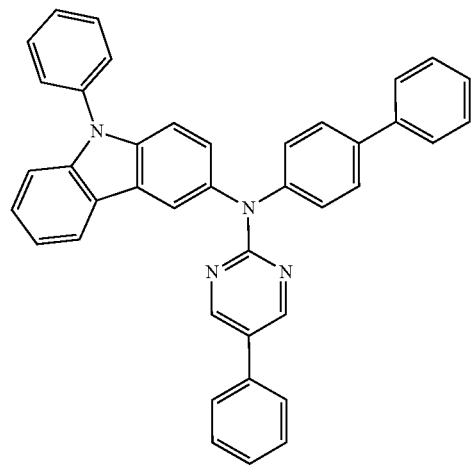

C-2

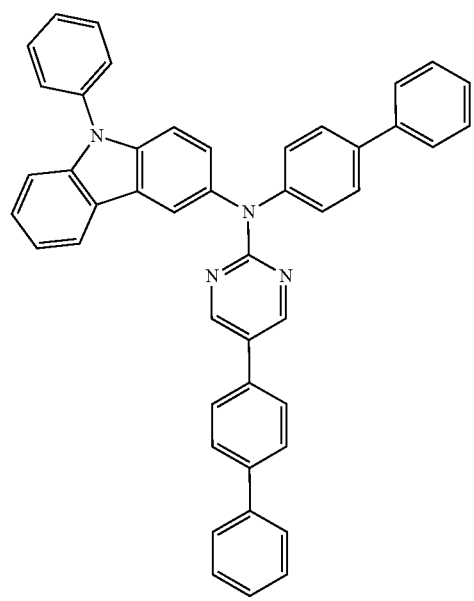

-continued

C-3

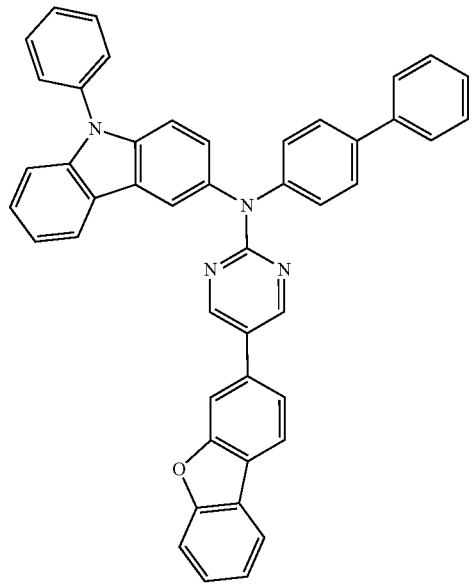

C-4

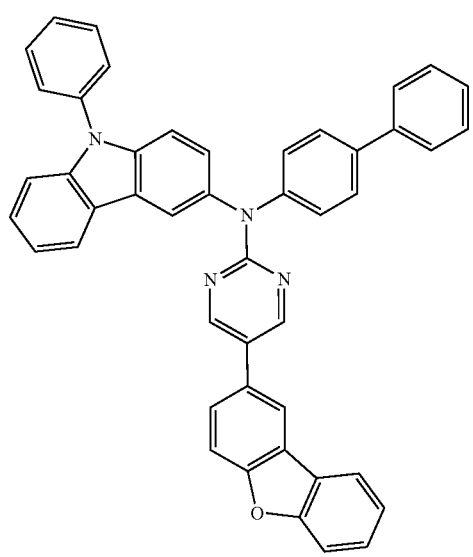

C-5

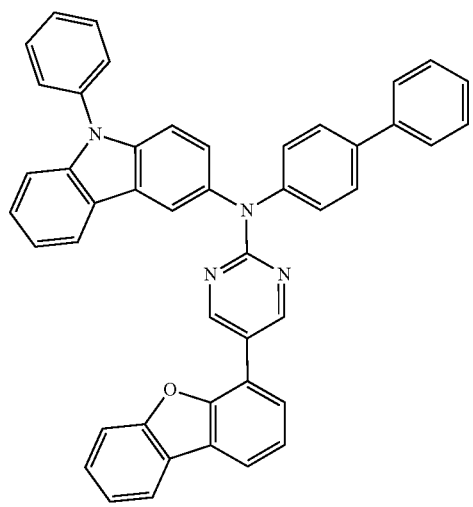

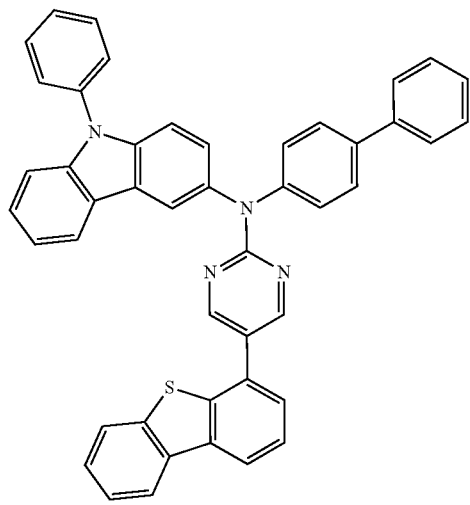
C-6
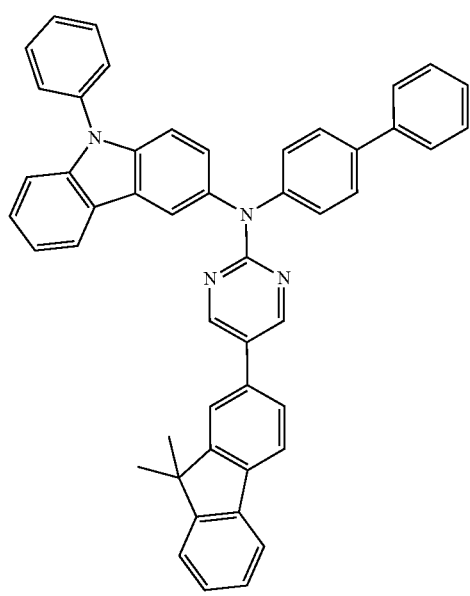
C-7
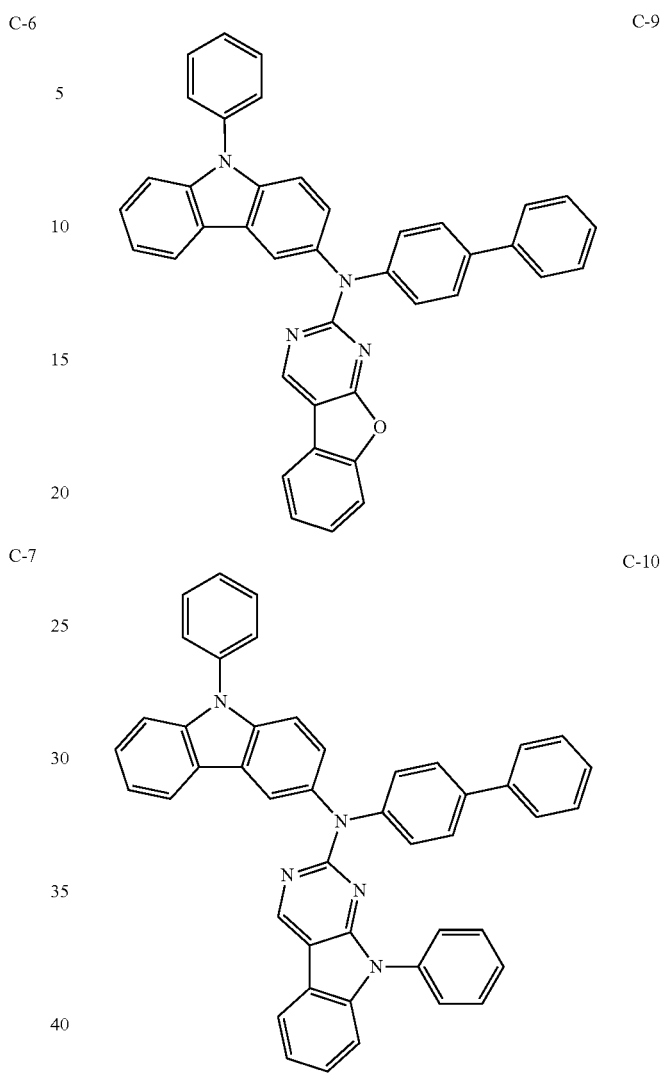
C-8
C-9
C-10
C-11

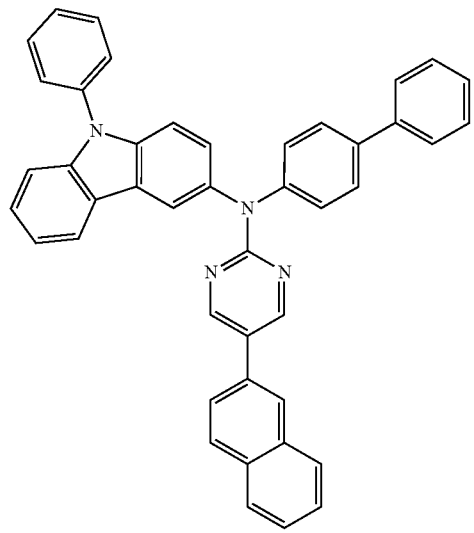
C-12
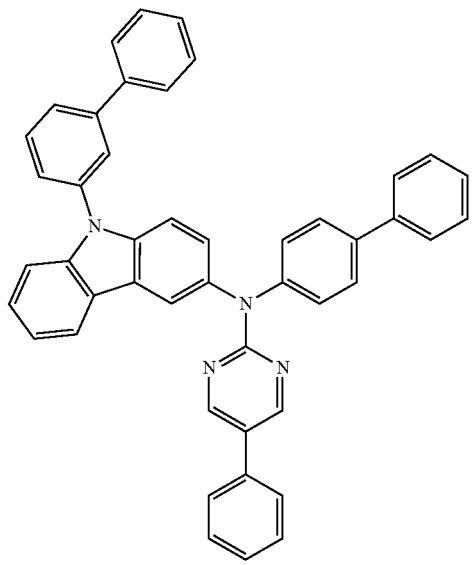
C-14
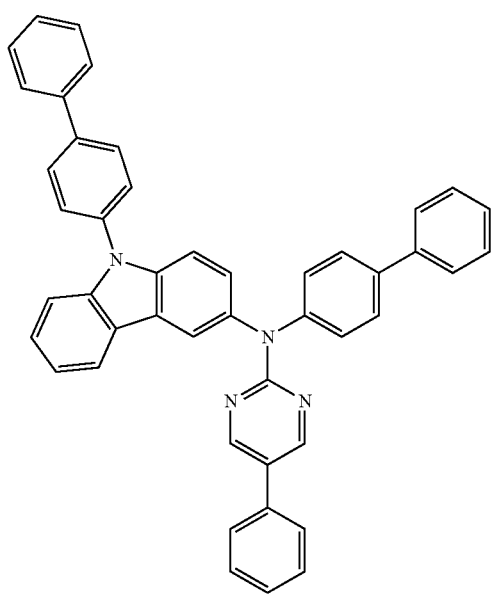
C-13
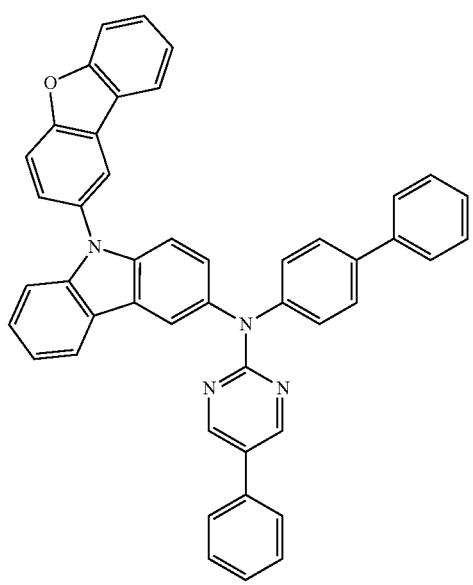
C-15

C-16
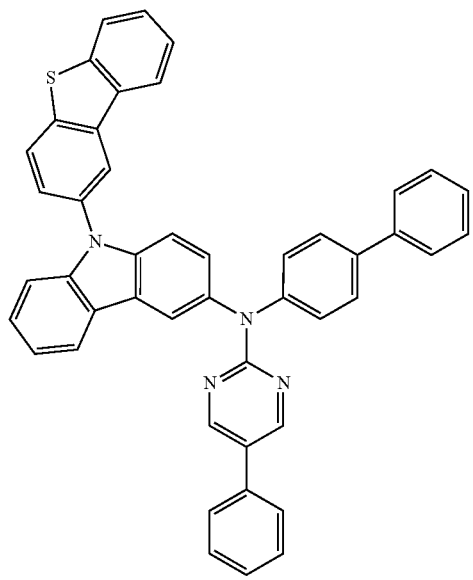
C-18
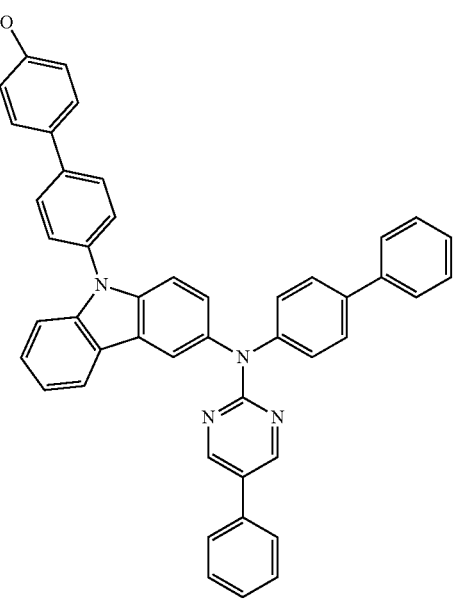
C-17
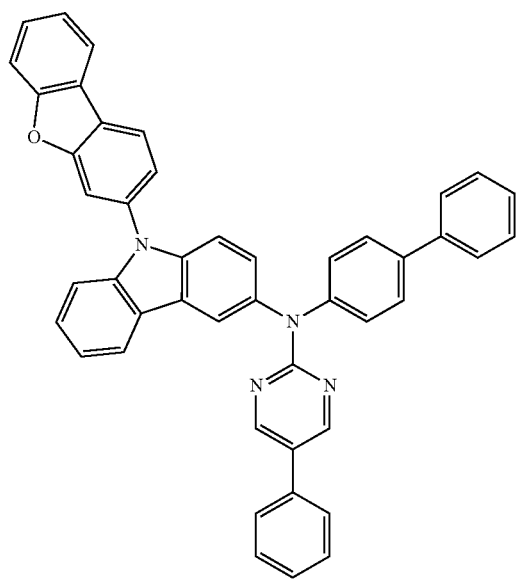
C-19
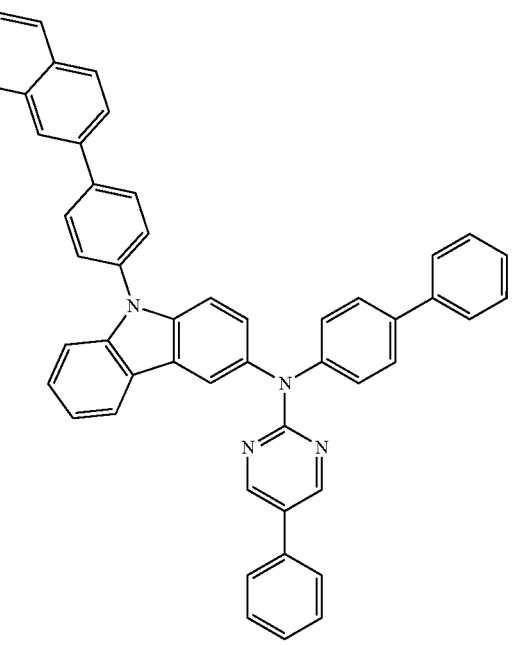

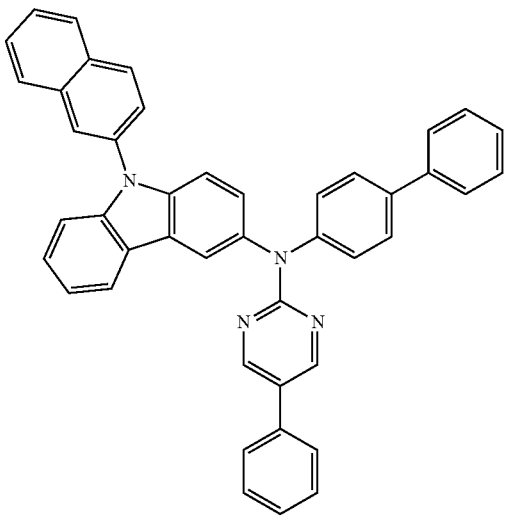
C-20
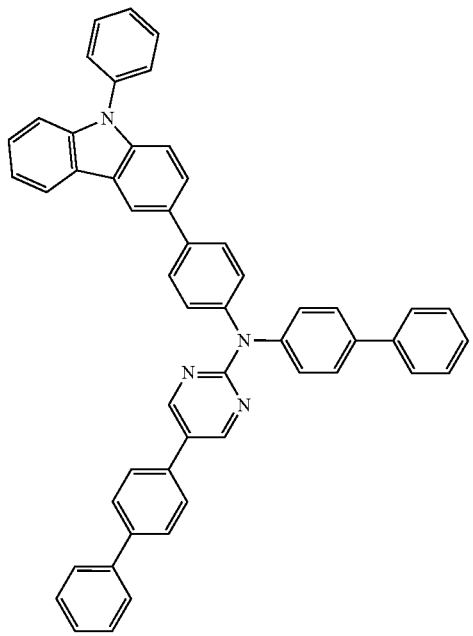
C-22
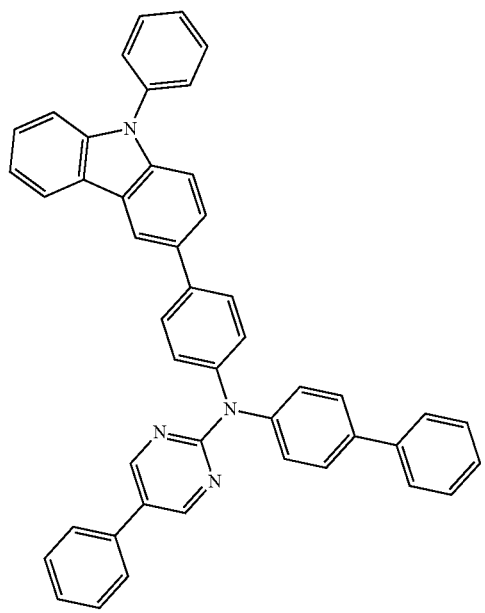
C-21
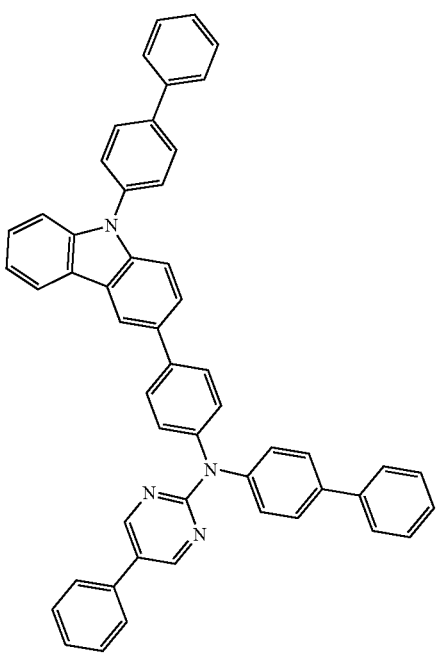
C-23

C-24
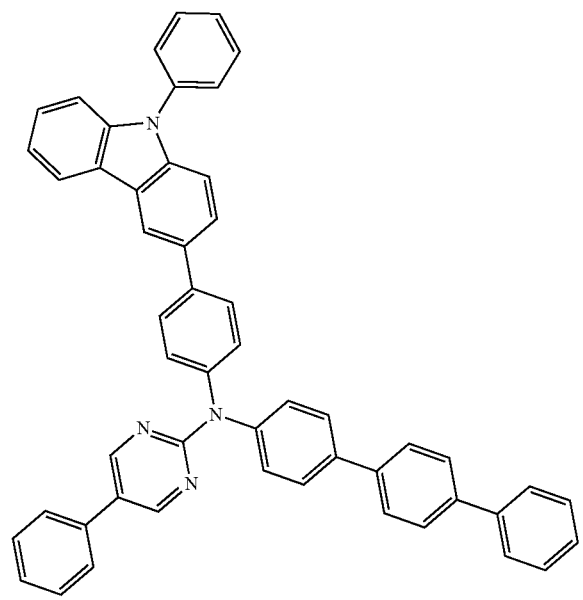
C-25
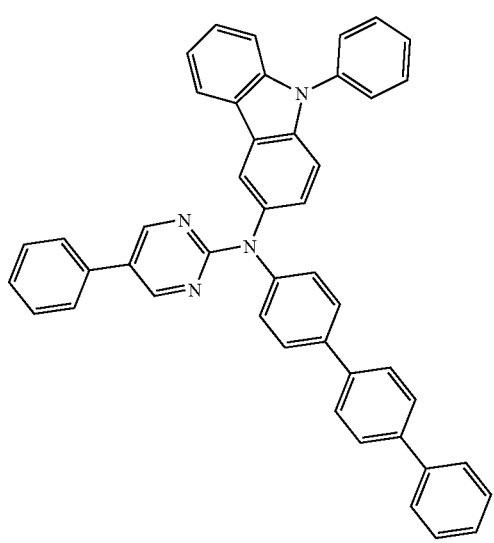
C-26
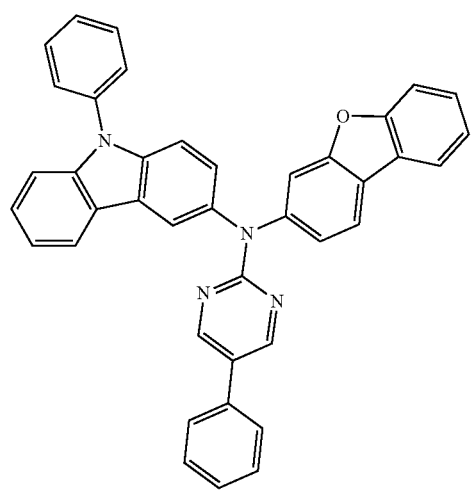
C-27
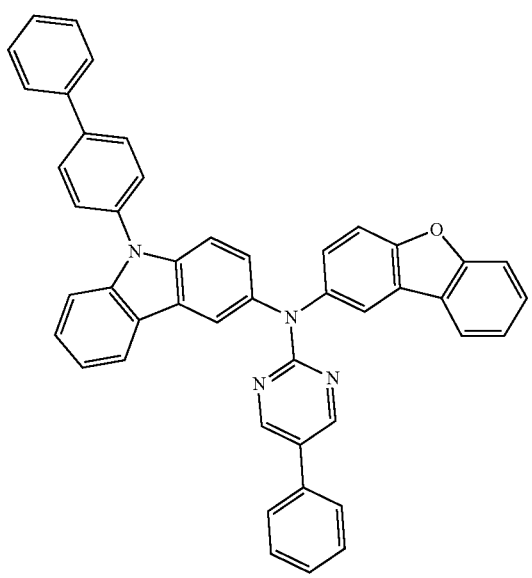
C-28
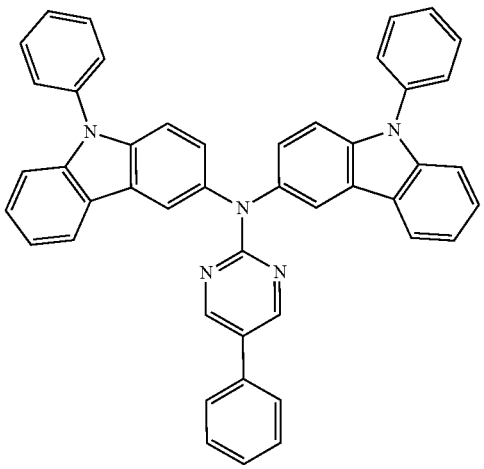
C-29
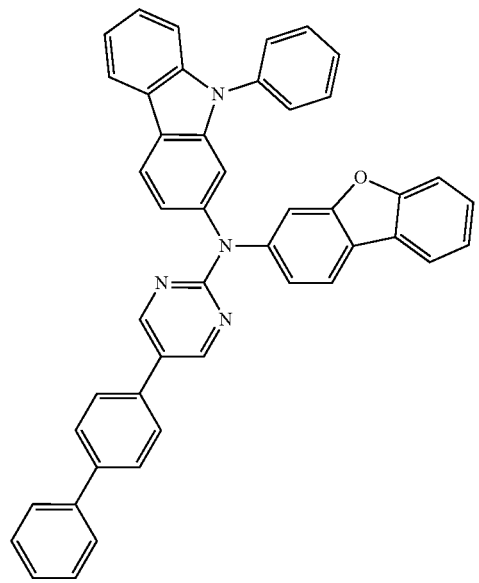

C-30
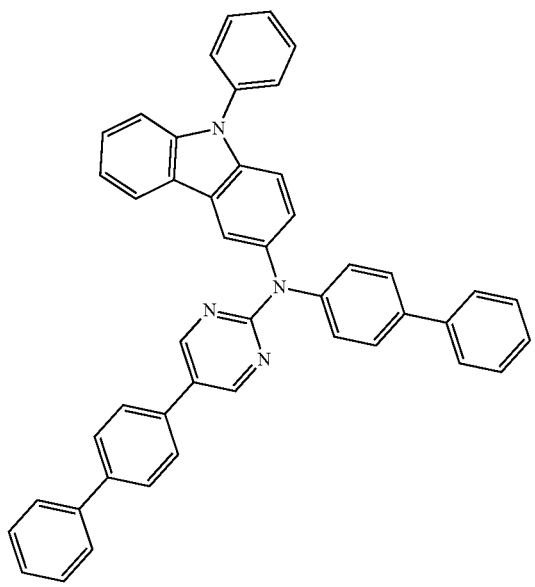
C-31
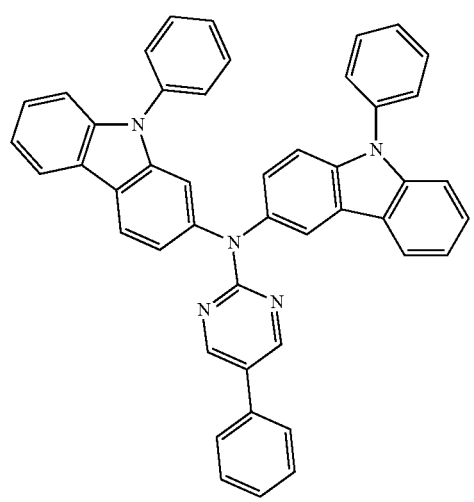
C-32
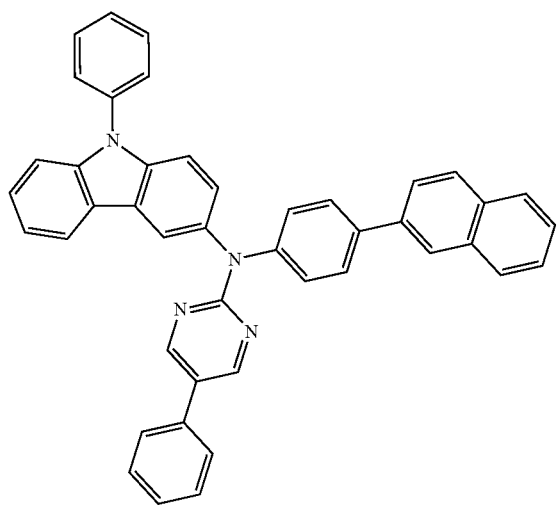
C-33
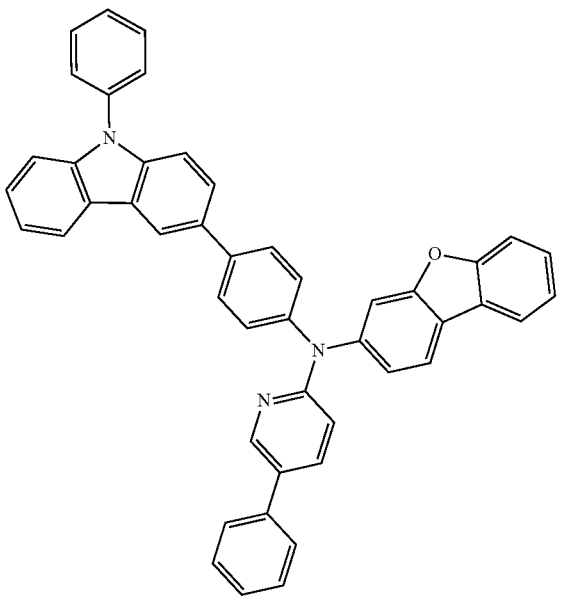
C-34
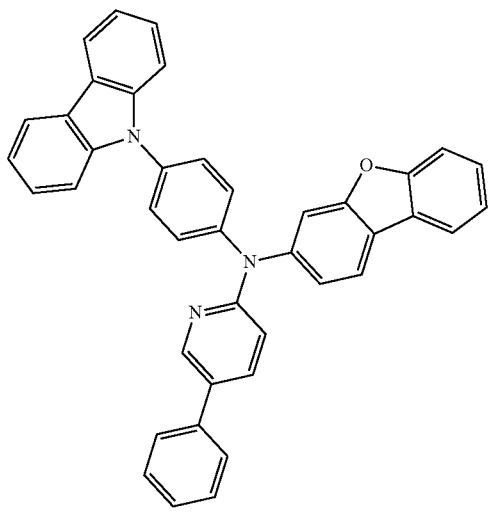
C-35
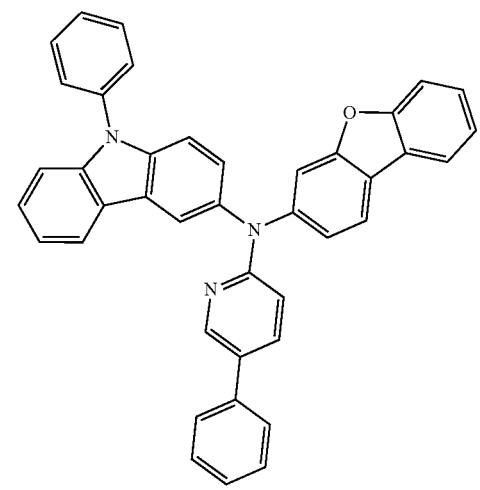

C-36
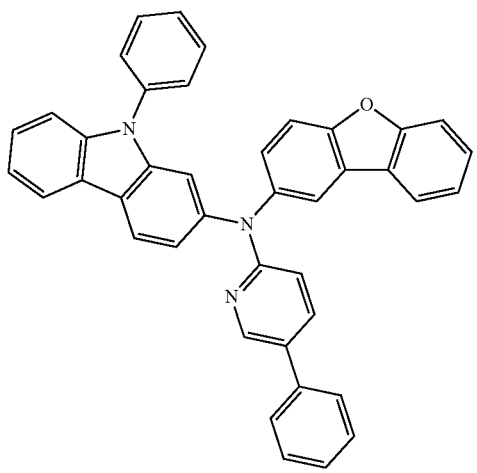
C-37
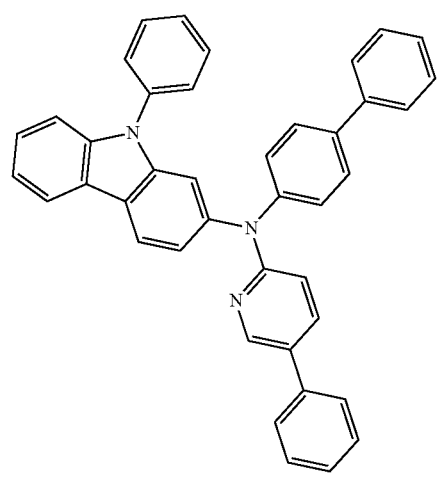
C-38
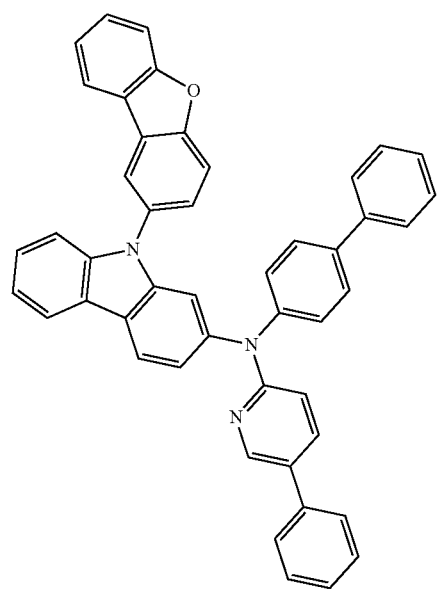
C-39
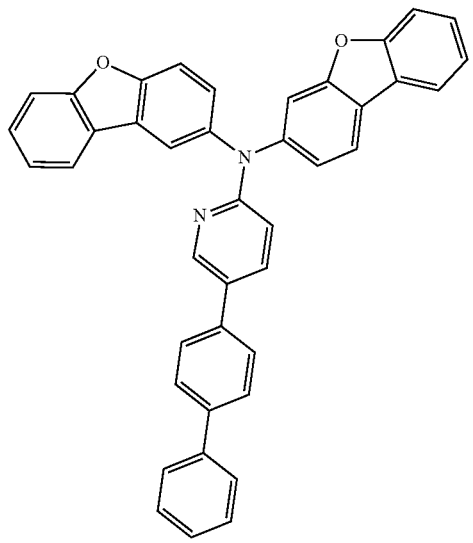
C-40
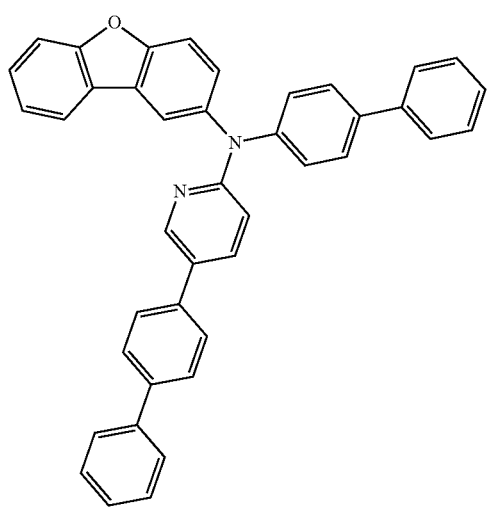
C-41
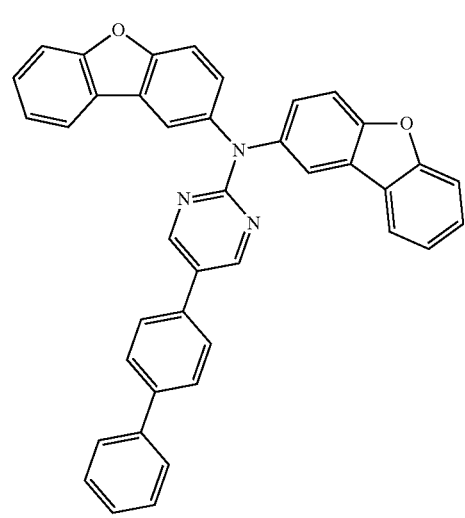

C-42
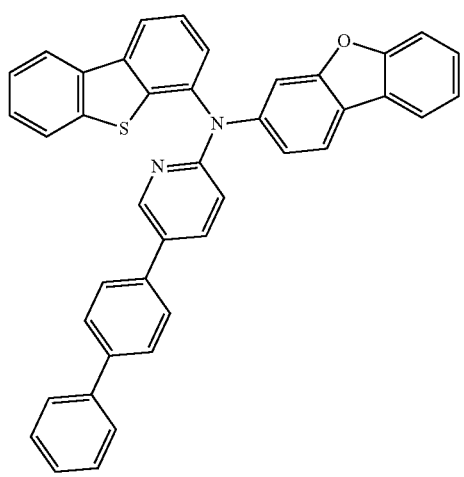
C-45
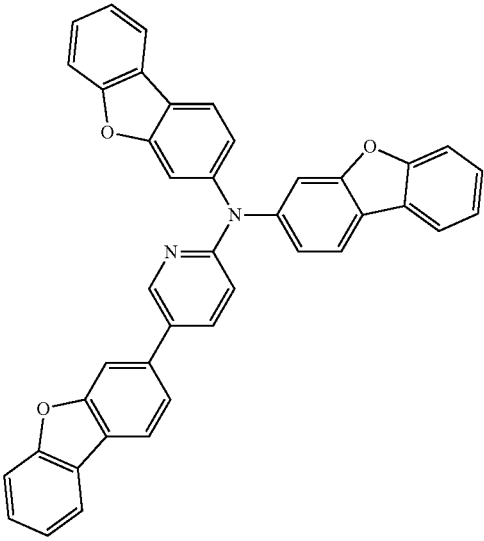
C-43
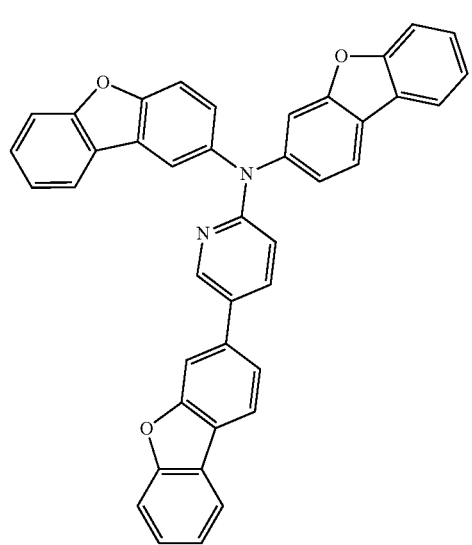
C-44
C-46
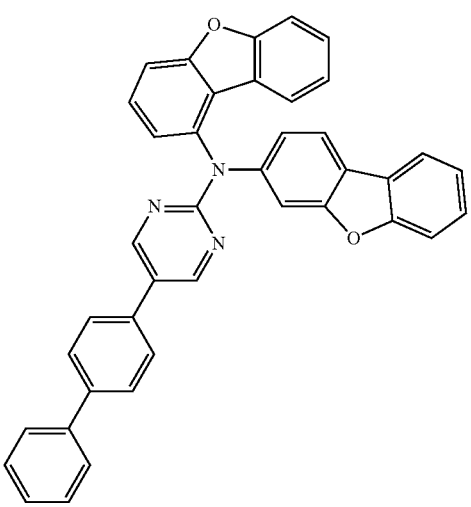

C-47
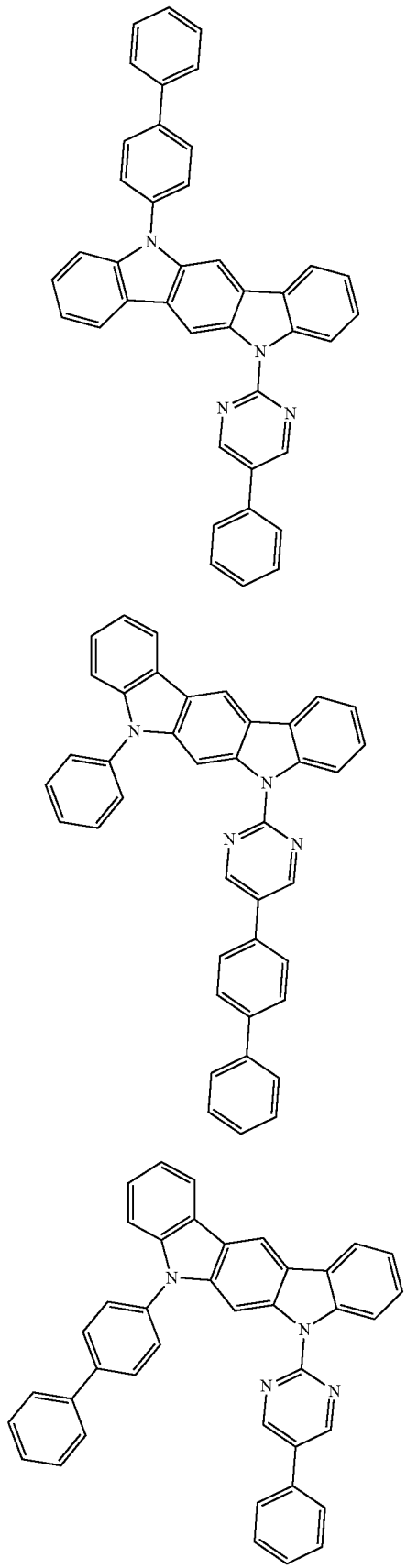
C-48
C-49
C-50
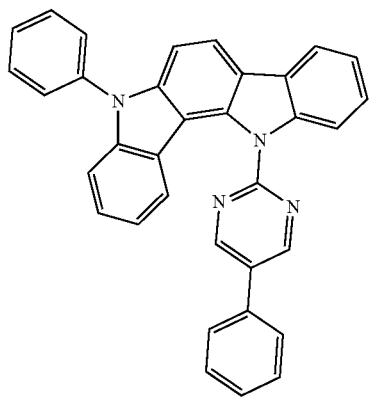
C-51
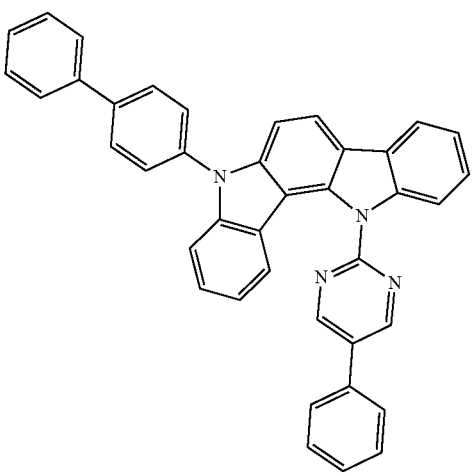
C-52
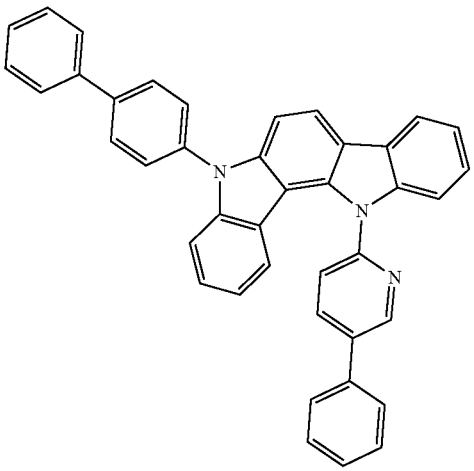

C-53
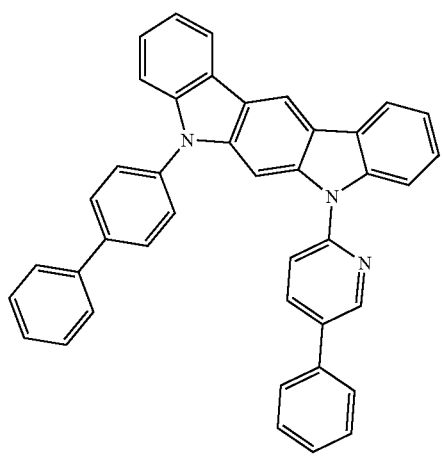
C-54
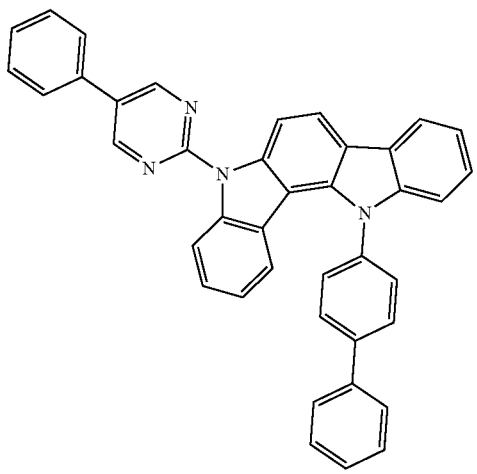
C-55
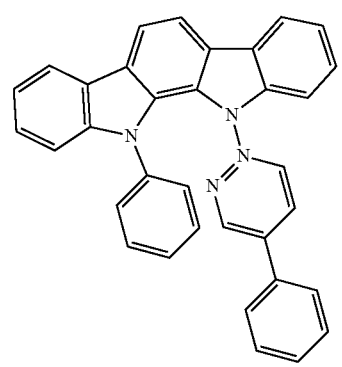
C-56
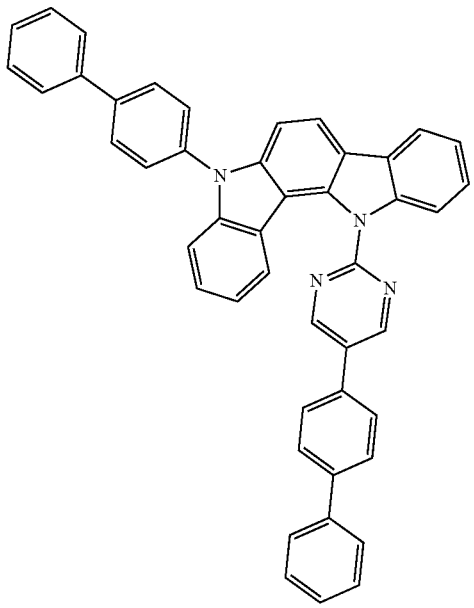
C-57
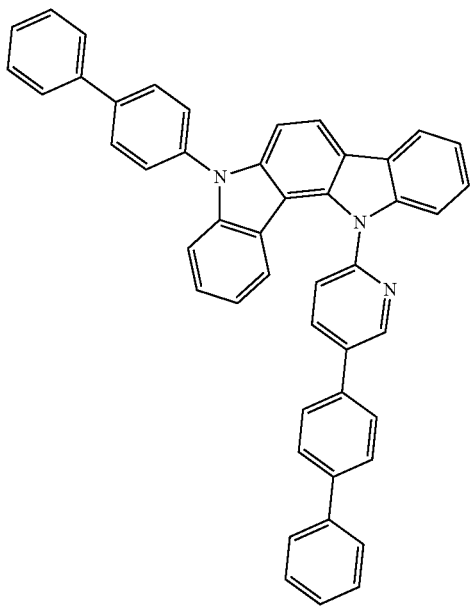

C-58
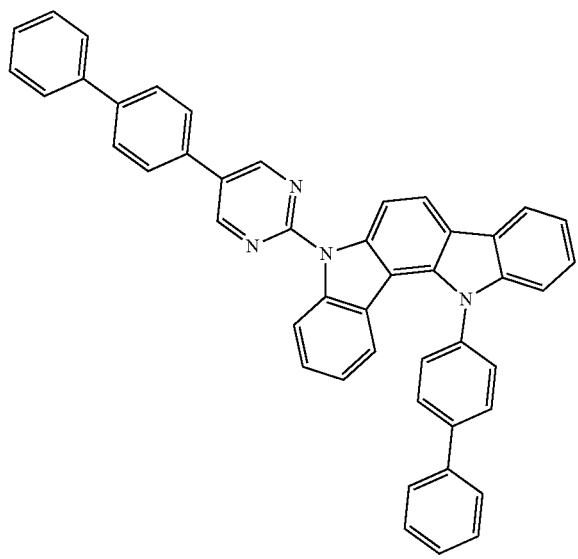
C-59
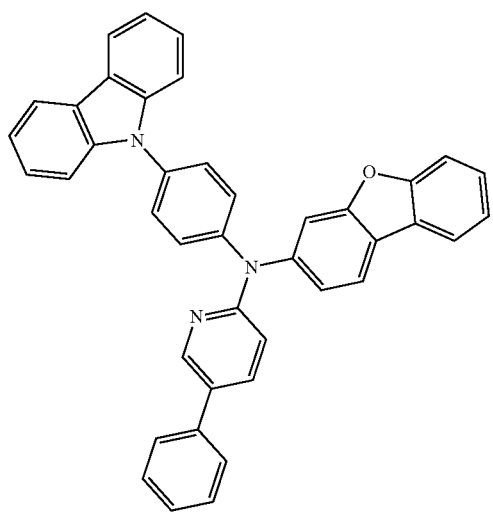
C-60
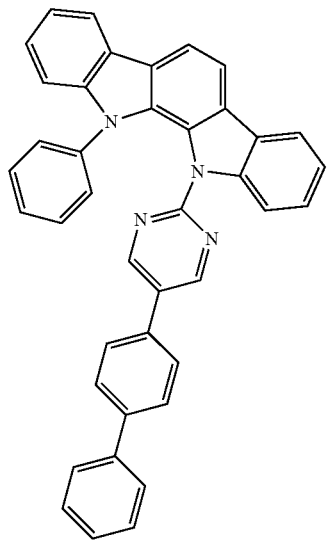
C-61
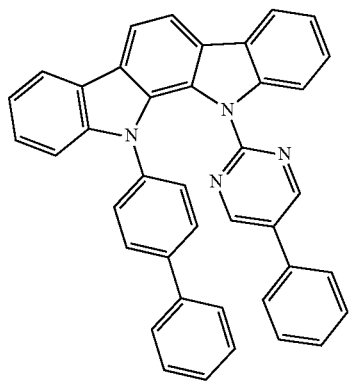
C-62
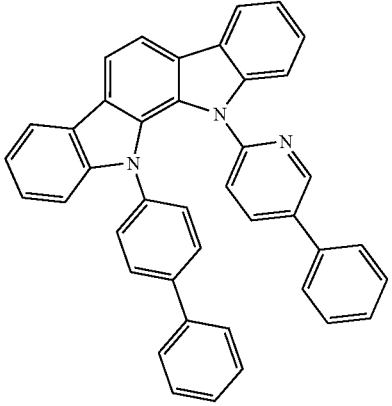
C-63
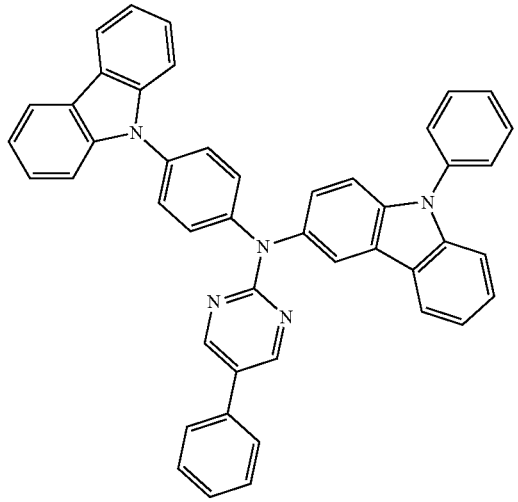

C-64
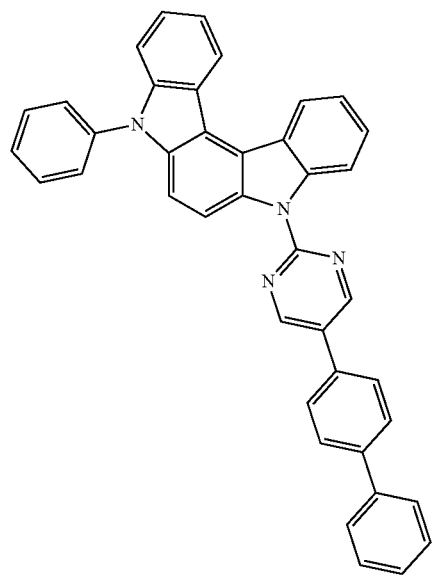
C-65
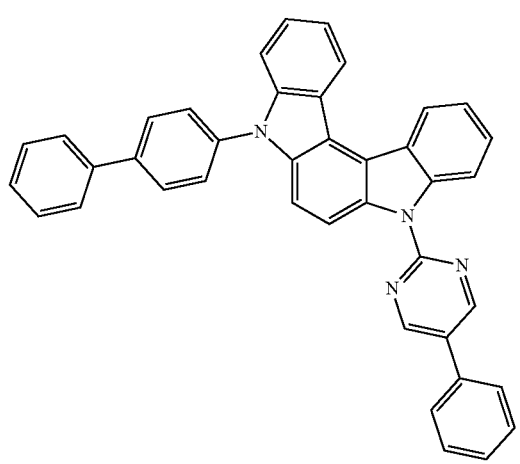
C-66
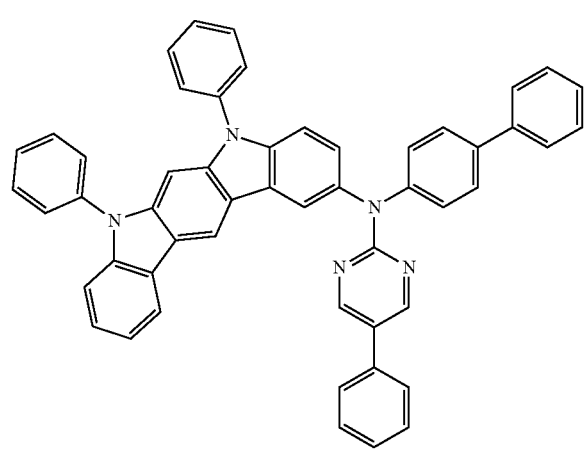
C-67
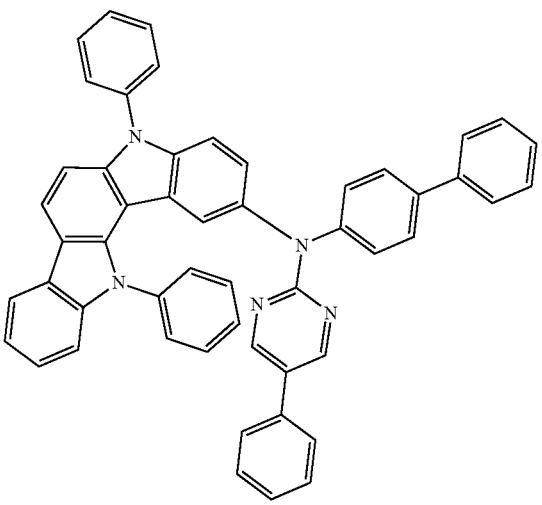
C-68
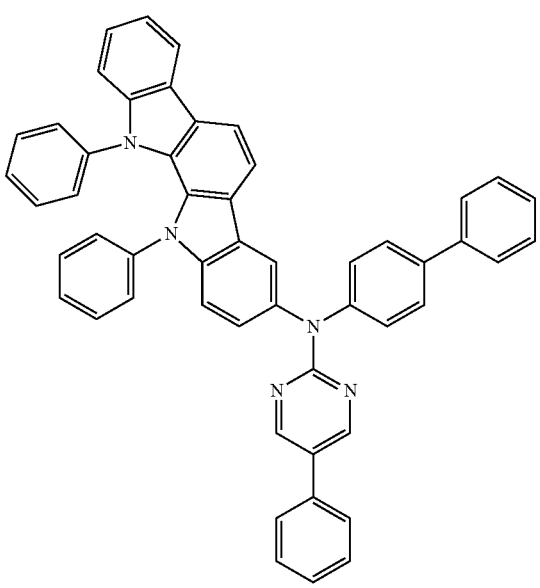

-continued
C-69
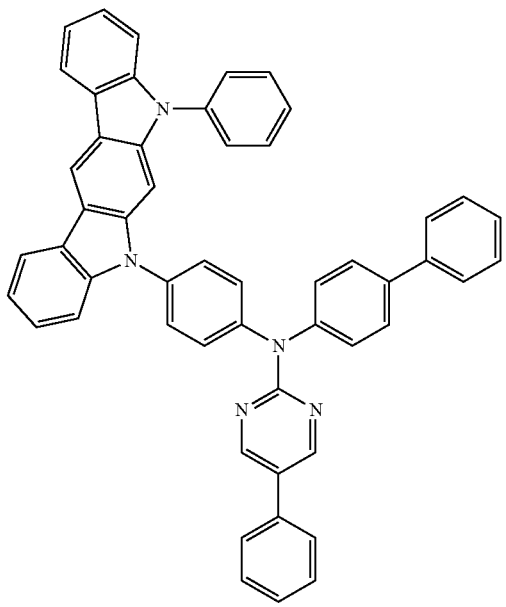
C-70
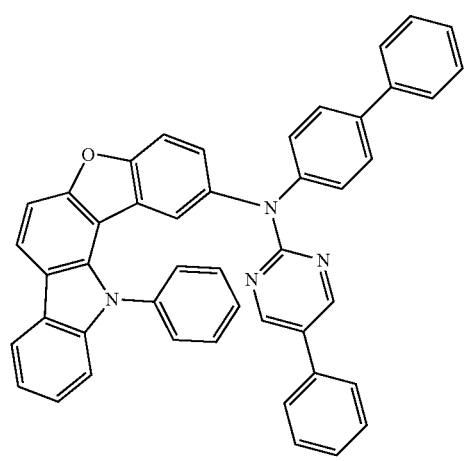
C-71
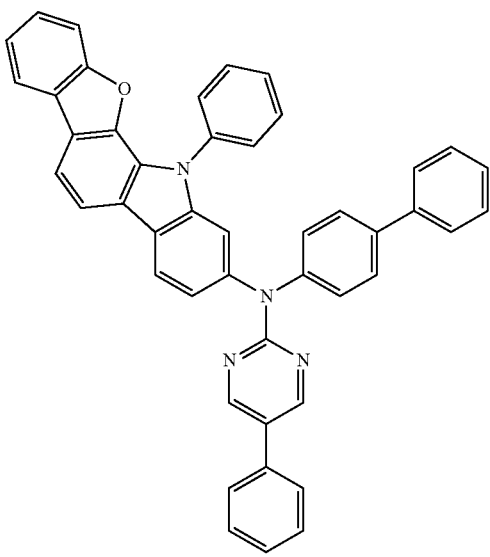
-continued
C-72
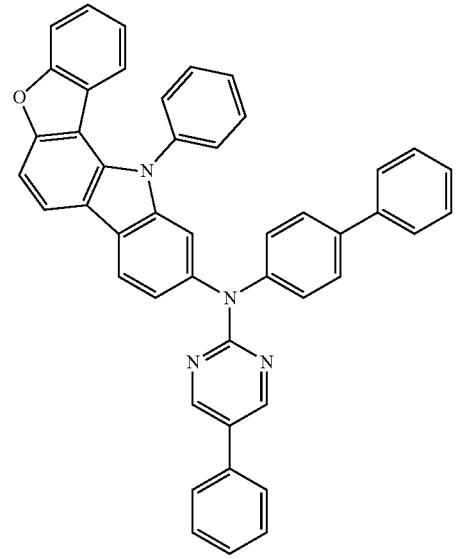
C-73
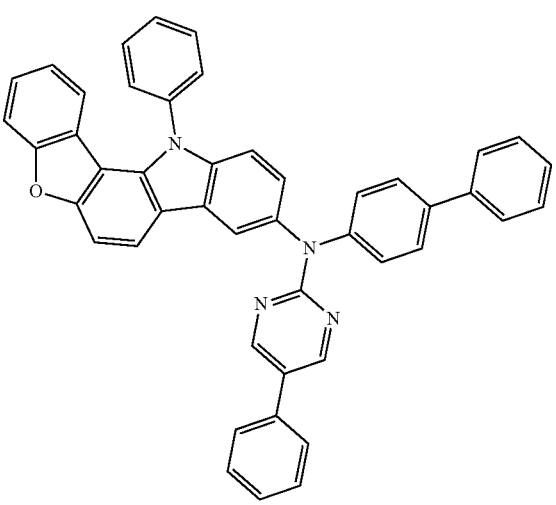
C-74
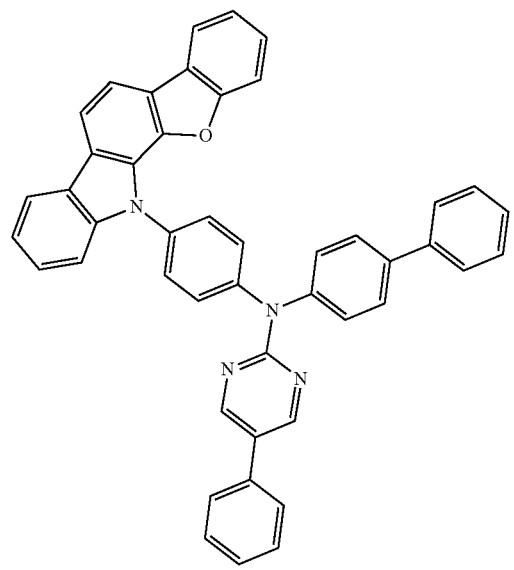

C-75
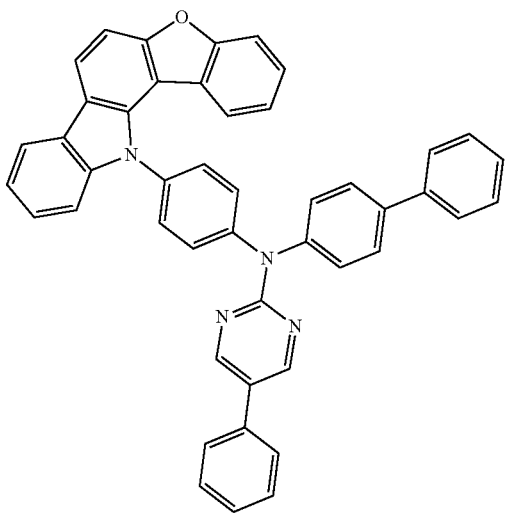
C-78
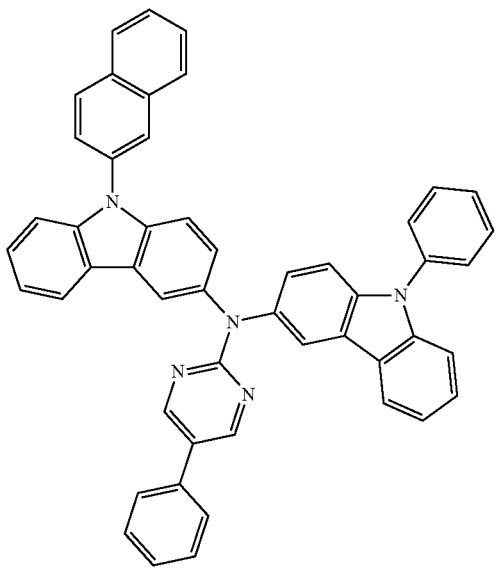
C-76
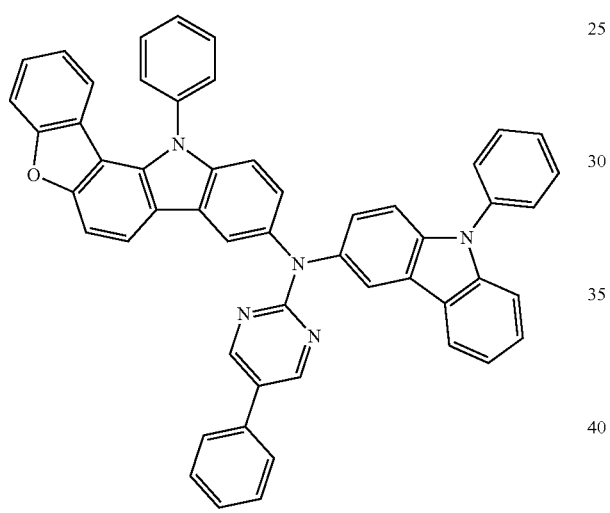
C-77
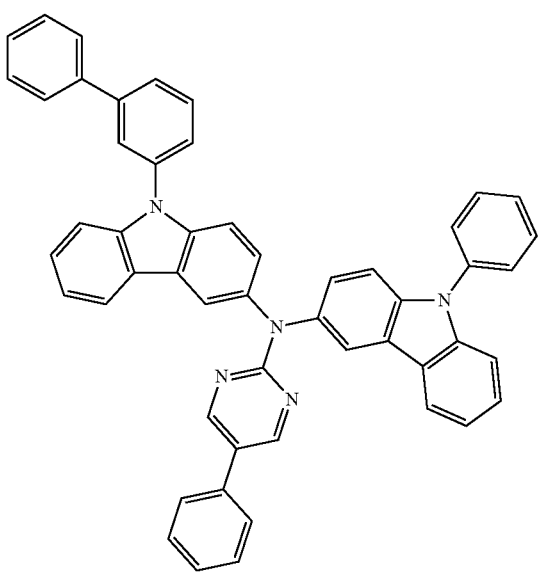
C-79
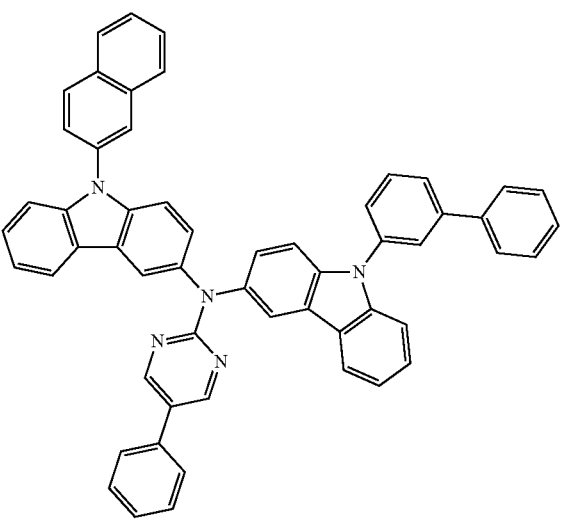

C-80
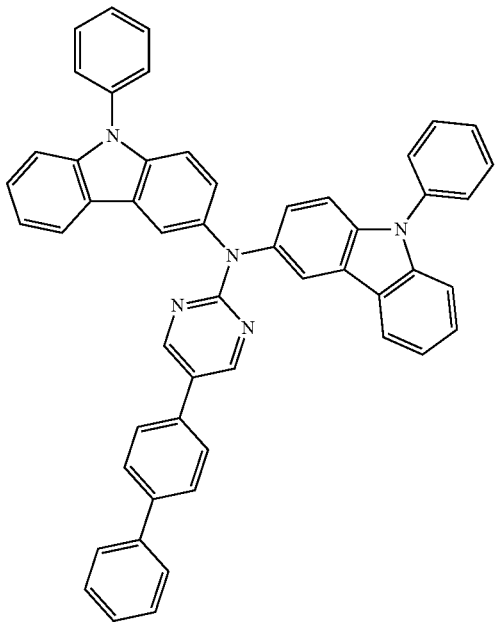

C-81
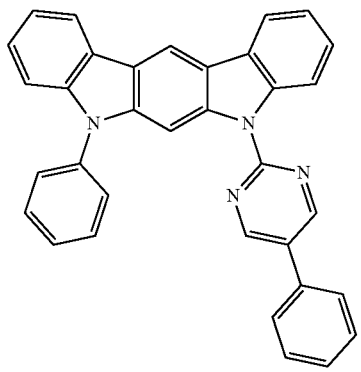

C-82
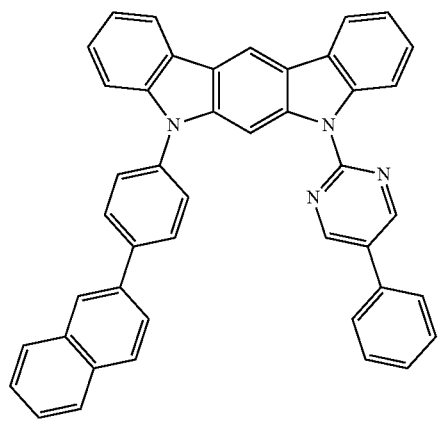

C-83

C-84
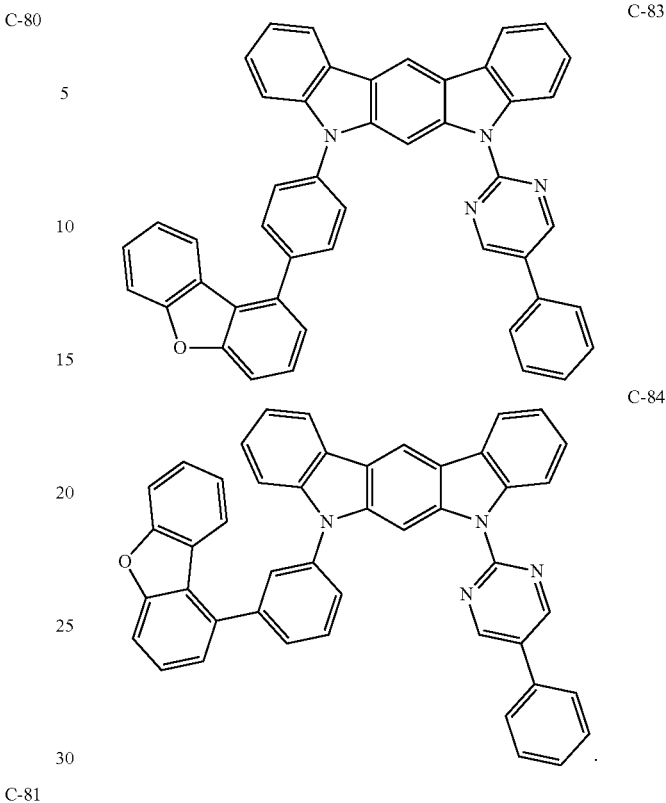

The present disclosure provides an organic electroluminescent material comprising the organic electroluminescent compound of formula 1 and an organic electroluminescent device comprising the organic electroluminescent material.

The organic electroluminescent material may be comprised solely of the organic electroluminescent compound of the present disclosure, or may further comprise conventional materials included in the organic electroluminescent material.

The organic electroluminescent compound according to formula 1 of the present disclosure may be comprised in a hole transport layer (HTL), a light-emitting layer (EML), an electron buffer layer (a compound deposited between the electron transport layer and the light-emitting layer in the deposited device), and an electron transport layer (ETL), etc., preferably a light-emitting layer.

Meanwhile, the organic electroluminescent device according to the present disclosure includes a first electrode; a second electrode; and at least one organic layer interposed between the first electrode and the second electrode. The organic layer may comprise the organic electroluminescent compound of formula 1. The organic layer may further comprise at least one compound selected from the group consisting of an arylamine-based compound and a styrylarylamine-based compound. Also, the organic layer may further comprise at least one metal selected from the group consisting of metals of Group 1, metals of Group 2, transition metals of the 4th period, transition metals of the 5th period, lanthanides, and organic metals of the d-transition elements of the Periodic Table, or at least one complex compound comprising such a metal.

One of the first electrode and the second electrode may be an anode and the other may be a cathode. The organic layer comprises a light-emitting layer, and may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. Also, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. The hole transport layer or the electron blocking layer may be multi-layers, wherein each layer may use a plurality of compounds.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each layer may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as the hole auxiliary layer or the electron blocking layer. The light-emitting auxiliary layer, the hole auxiliary layer, or the electron blocking layer may have an effect of improving the efficiency and/or the lifespan of the organic electroluminescent device.

In the organic electroluminescent device of the present disclosure, preferably, at least one layer (hereinafter, "a surface layer") selected from a chalcogenide layer, a halogenated metal layer, and a metal oxide layer may be placed on an inner surface(s) of one or both electrode(s). Specifically, a chalcogenide (including oxides) layer of silicon and aluminum is preferably placed on an anode surface of an electroluminescent medium layer, and a halogenated metal layer or a metal oxide layer is preferably placed on a cathode surface of an electroluminescent medium layer. The operation stability for the organic electroluminescent device may be obtained by the surface layer. Preferably, the chalcogenide includes $SiO_X$ ($1 \leq X \leq 2$), $AlO_X$ ($1 \leq X \leq 0.5$), SiON, SiAlON, etc.; the halogenated metal includes LiF, $MgF_2$, $CaF_2$, a rare earth metal fluoride, etc.; and the metal oxide includes $Cs_2O$, $Li_2O$, MgO, SrO, BaO, CaO, etc.

In addition, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. Also, a reductive dopant layer may be employed as a charge generating layer to produce an organic electroluminescent device having two or more light-emitting layers and emitting white light.

The organic electroluminescent compound represented by formula 1 may be comprised in the light-emitting layer. When used in the light-emitting layer, the organic electroluminescent compound of formula 1 may be comprised as a host material. Preferably, the light-emitting layer may further comprise at least one dopant. If necessary, another compound besides the organic electroluminescent compound of formula 1 may be further comprised as a second host material. Herein, the weight ratio of the first host material to the second host material is in the range of 1:99 to 99:1. The second host material can use any of the known phosphorescent hosts.

The second host material according to one embodiment is preferably selected from the compound represented by the following formula 11 or 12 in view of luminous efficiency, but is not limited thereto.

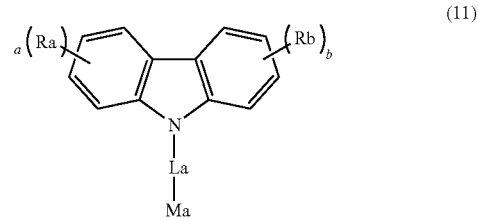

(11)

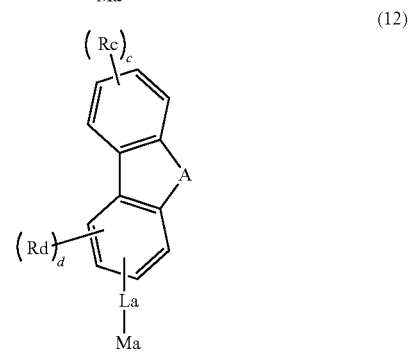

(12)

In formulae 11 and 12,

Ma represents a substituted or unsubstituted (C6-C30) aryl, a substituted or unsubstituted mono- or di-(C6-C30) arylamino, or a substituted or unsubstituted (3- to 30-membered)heteroaryl;

La represents a single bond, a substituted or unsubstituted (C6-C30)arylene, or a substituted or unsubstituted (3- to 30-membered)heteroarylene;

A represents S, O, NR$_7$ or CR$_8$R$_9$;

Ra to Rd each independently represent a hydrogen, deuterium, halogen, cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted (C1-C30)alkyl(C6-C30)arylamino, or a substituted or unsubstituted mono- or di-(C6-C30)arylamino; or may be linked to an adjacent substituent to form a substituted or unsubstituted (C3-C30) mono- or polycyclic, alicyclic or aromatic ring or the combination thereof, whose carbon atom may be replaced with at least one heteroatom selected from nitrogen, oxygen, and sulfur;

R$_7$ to R$_9$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; R$_8$ and R$_9$ may be linked to an adjacent substituent to form a substituted or unsubstituted (C3-C30) mono- or polycyclic, alicyclic or aromatic ring or the combination thereof, whose carbon atom may be replaced with at least one heteroatom selected from nitrogen, oxygen, and sulfur;

a to c each independently represent an integer of 1 to 4, d represents an integer of 1 to 3;

the heteroaryl(ene) contains at least one heteroatom selected from B, N, O, S, Si, and P.

One embodiment, the second host material of formula 11, may be the second host, represented by the following formula 3.

stituted or unsubstituted quinolinyl, a substituted or unsubstituted quinazolinyl, a substituted or unsubstituted [1]Benzothieno[3,2-d]pyrimidine or a substituted or unsubstituted [1]Benzofuro[2,3-d]pyrimidine;

L$_{21}$ represents a single bond, a substituted or unsubstituted (C6-C30)arylene or a substituted or unsubstituted (5- to 30-membered)heteroarylene; preferably, may be a single bond, a substituted or unsubstituted (C6-C25)arylene or a substituted or unsubstituted (5- to 25 membered)heteroarylene; more preferably, may be a single bond, a substituted or unsubstituted (C6-C18)arylene or a substituted or unsubstituted (5- to 18-membered)heteroarylene, for example, a single bond, a substituted or unsubstituted phenylene, a substituted or unsubstituted naphthylene, a substituted or unsubstituted pyridylene, or a substituted or unsubstituted pyrimidylene;

R$_{21}$ to R$_{24}$ each independently represent hydrogen, deuterium, halogen, cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C6-C30)ar(C1-C30)alkyl, a substituted or unsubstituted (C3-C30)cycloalkyl, a substituted or unsubstituted (C1-C30)alkoxy, a substituted or unsubstituted (C1-C30)alkylsilyl, a substituted or unsubstituted (C6-C30)arylsilyl, a substituted or unsubstituted (C6-C30)ar(C1-C30)alkylsilyl, a substituted or unsubstituted (C1-C30)alkylamino, a substituted or unsubstituted (C6-C30)arylamino, or a substituted or unsubstituted (C1-C30)alkyl(C6-C30)arylamino; or may be linked to an adjacent substituent to form a substituted or unsubstituted (C3-C30) mono- or polycyclic, alicyclic or aromatic ring; preferably, R$_{21}$ to R$_{24}$ each independently may be a substituted or unsubstituted (C6-C25)aryl or may be linked to an adjacent substituent to form a substituted or unsubstituted (C3-C25) mono- or polycyclic, alicyclic or aromatic ring; more preferably, may be a substituted or unsubstituted (C6-C18)aryl; or may be linked to an adjacent substituent to form a (C3-C18) mono- or polycyclic, alicyclic or aromatic ring, e.g., a substituted or unsubstituted phenyl, or a substituted or unsubstituted naphthyl;

aa and cc each independently represent an integer of 1 to 4, and bb represents an integer of 1 or 2.

Specifically, the preferred examples of the second host material represented by formulae 11 and 12 are as follows, but are not limited thereto:

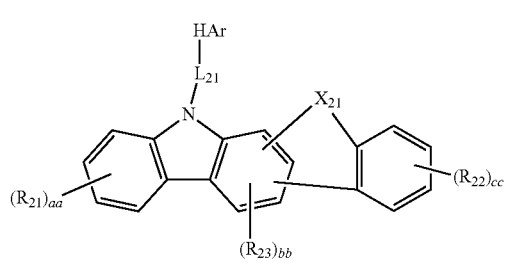

(3)

In formula 3,

X$_{21}$ represents O, S, or NR$_{24}$;

HAr represents a substituted or unsubstituted (5- to 30-membered)heteroaryl; preferably, may be a substituted or unsubstituted (5- to 25-membered)heteroaryl; more preferably, may be a substituted or unsubstituted (5- to 18-membered)heteroaryl; and the heteroaryl may contain at least one N; for example, HAr may be a substituted or unsubstituted pyrimidinyl, a substituted or unsubstituted triazinyl, a sub-

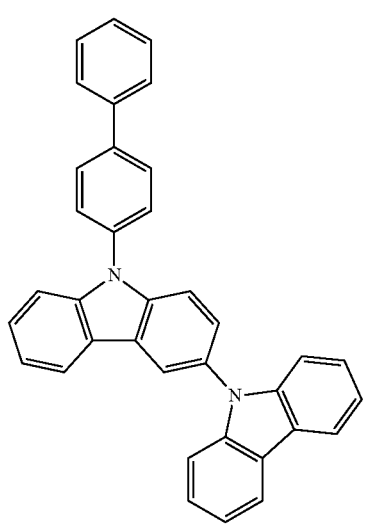

H-1

H-2
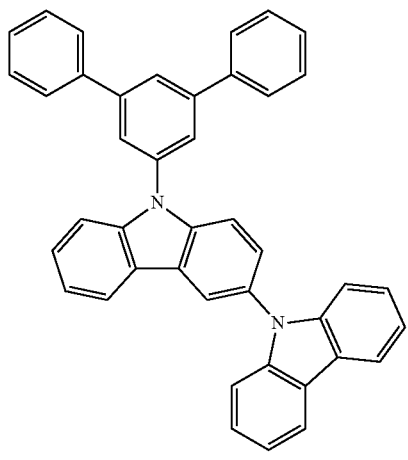
H-3
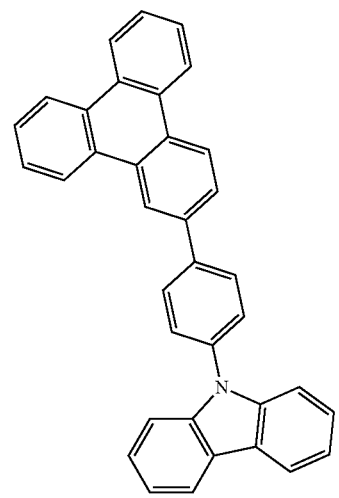
H-4
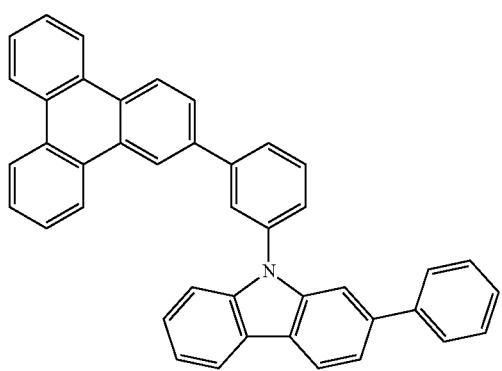
H-5
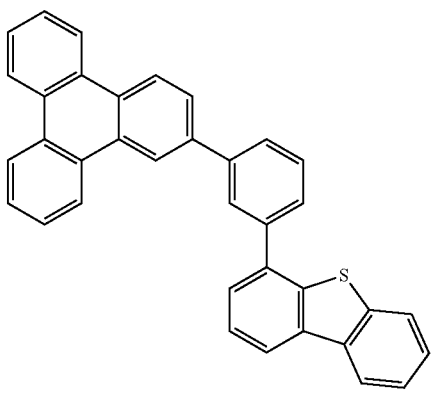
H-6
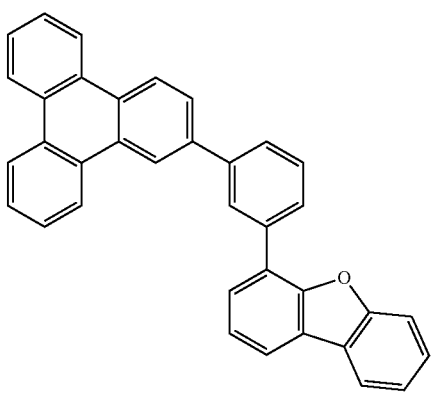
H-7
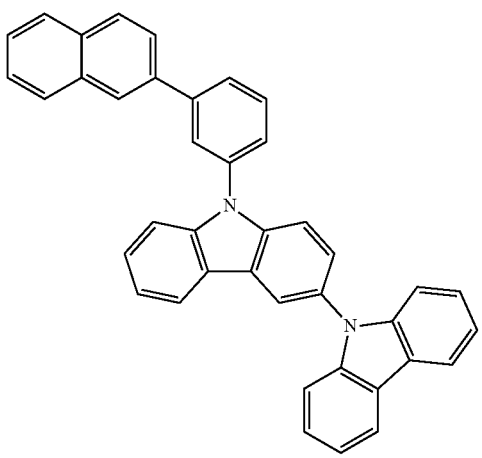

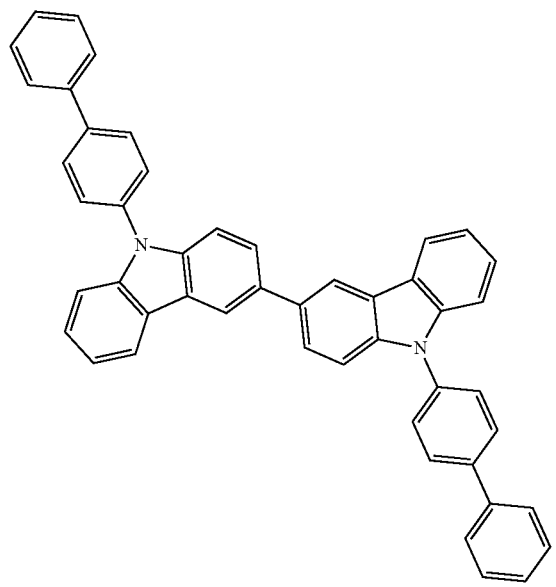
H-8
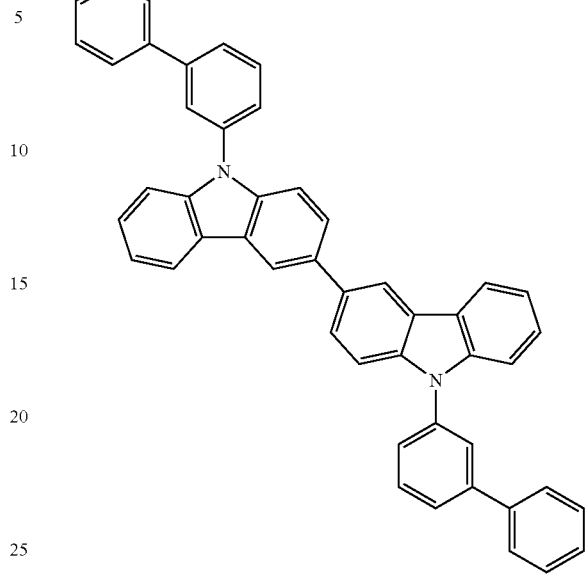
H-10
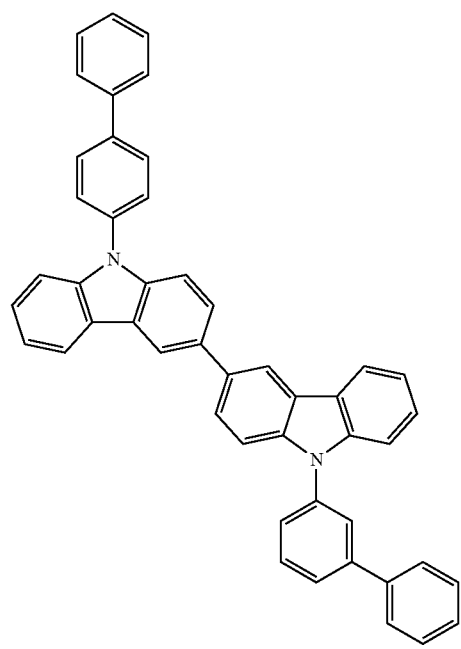
H-9
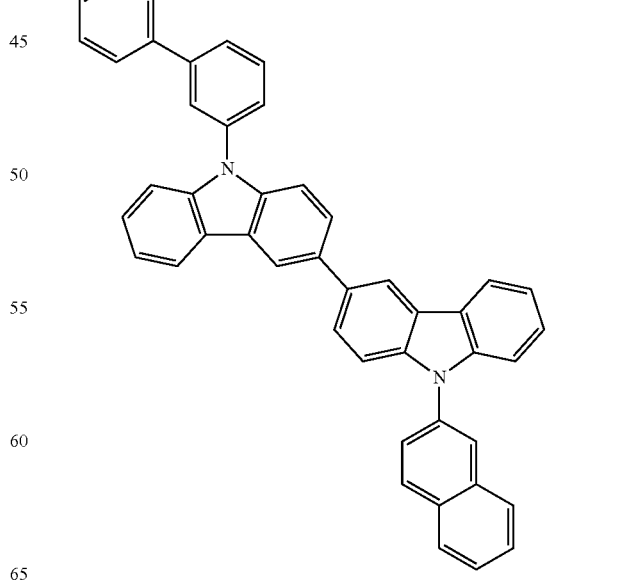
H-11

-continued
H-12
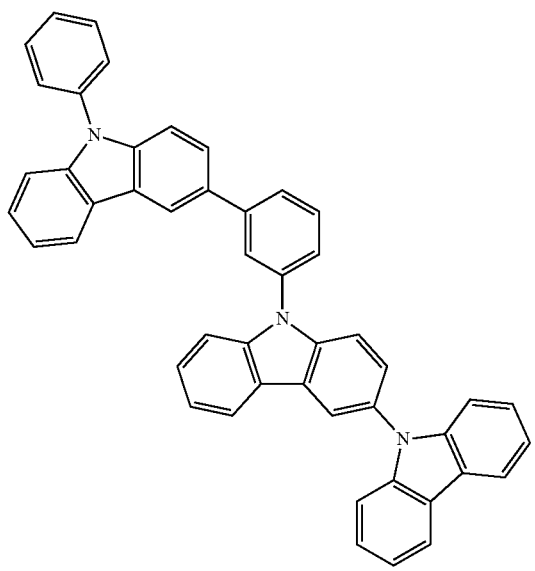
H-13
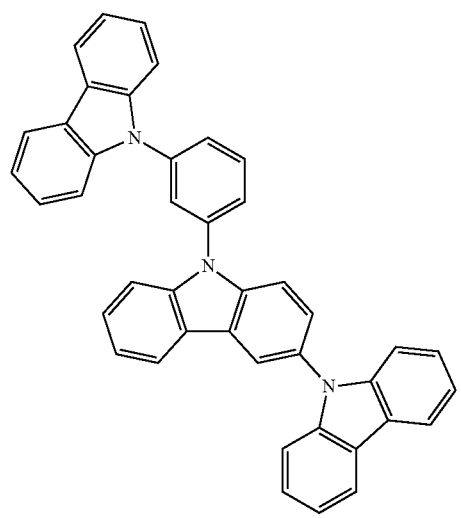
H-14
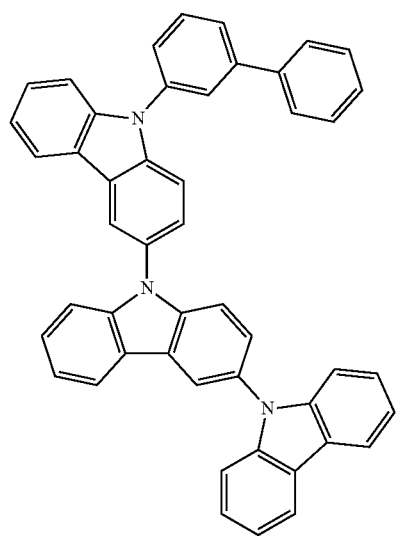
H-15
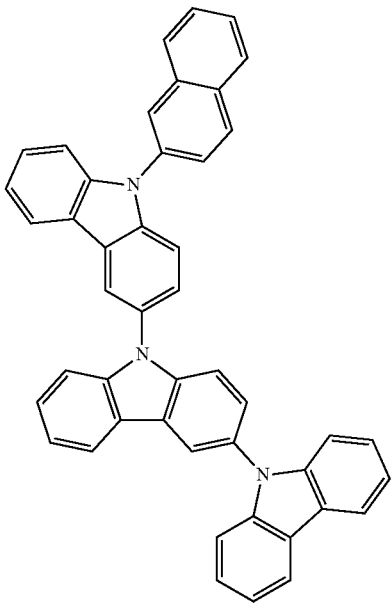
H-16
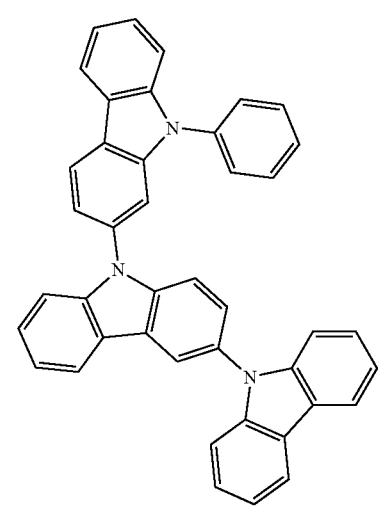
H-17
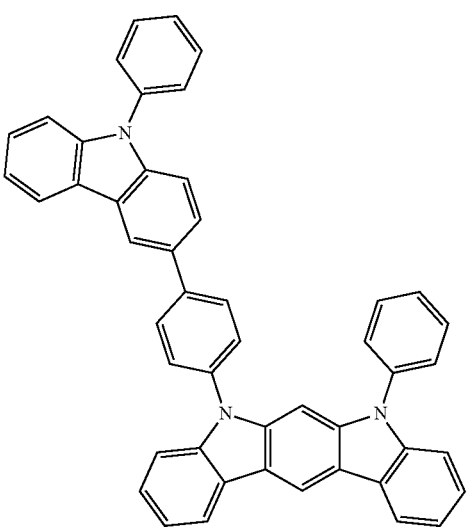

-continued
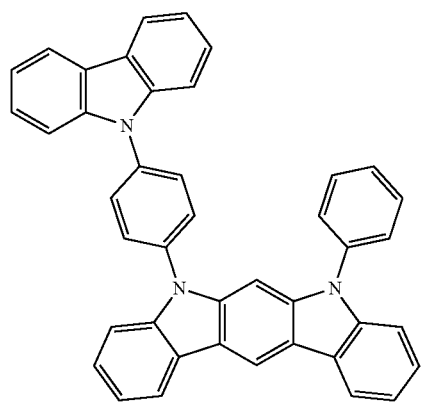
H-18
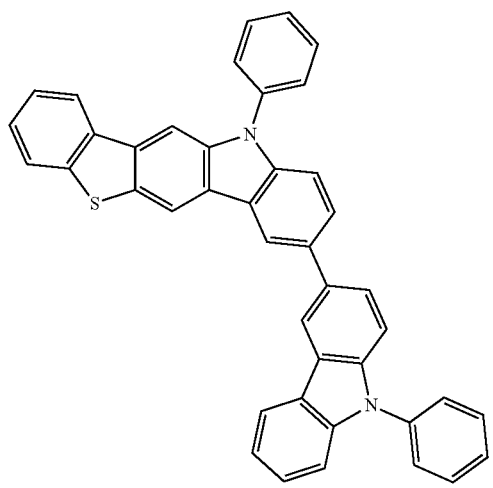
H-19
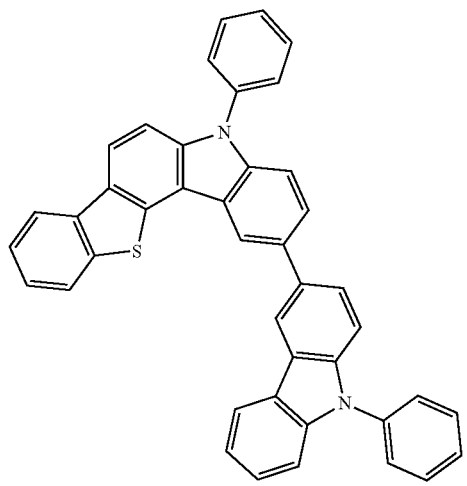
H-20
-continued
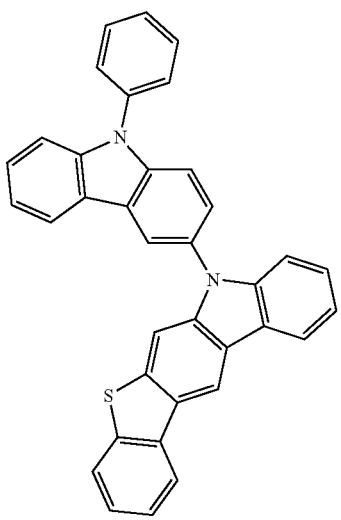
H-21
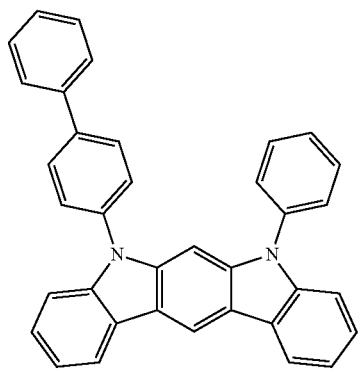
H-22
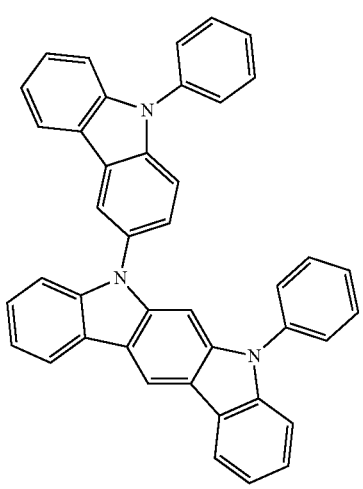
H-23

H-24
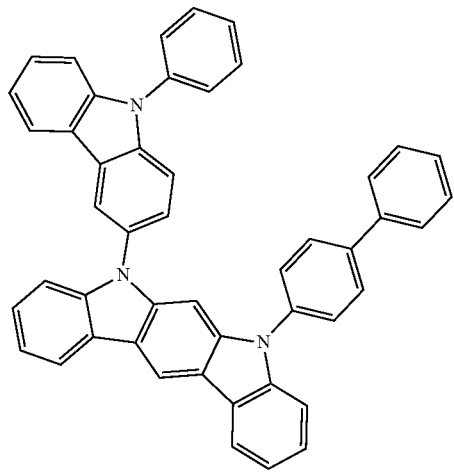
H-25
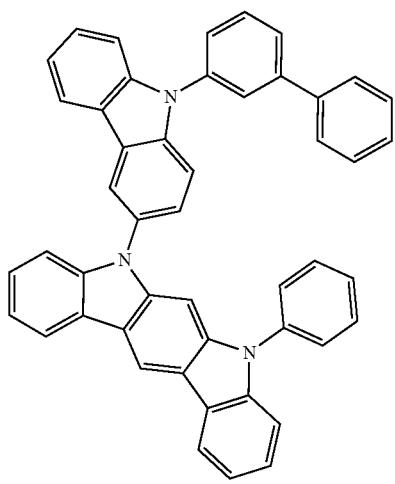
H-26
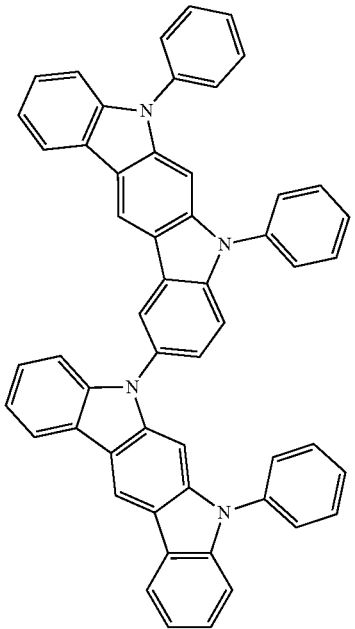
H-27
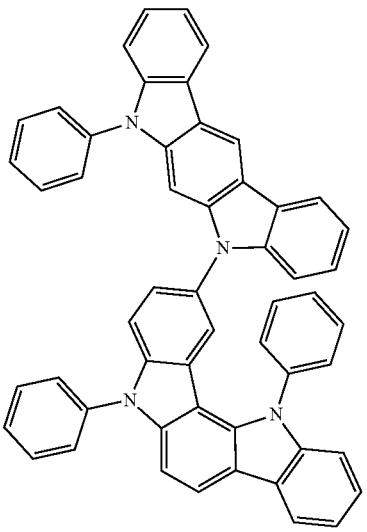
H-28
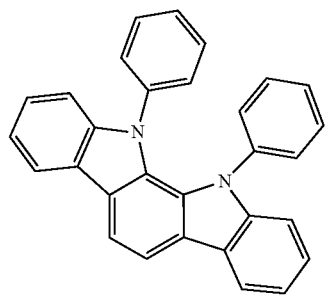
H-29
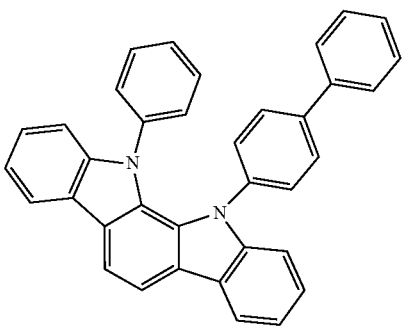
H-30
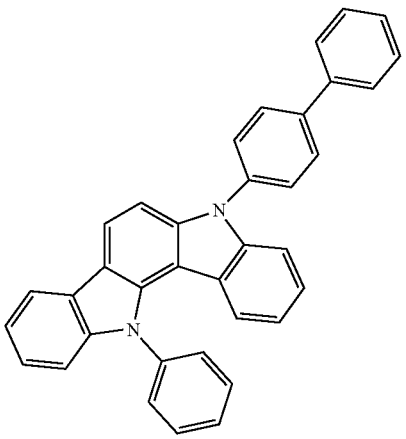

-continued
H-31
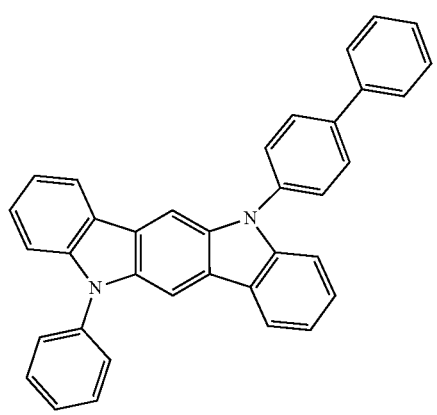
H-32
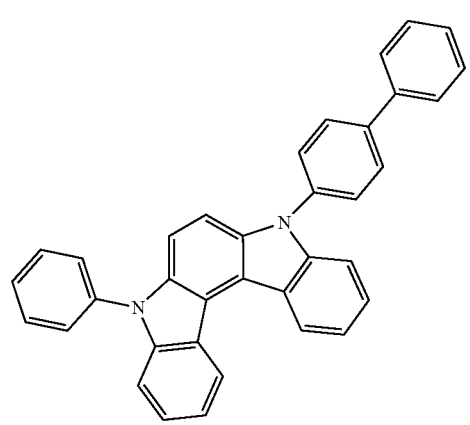
H-33
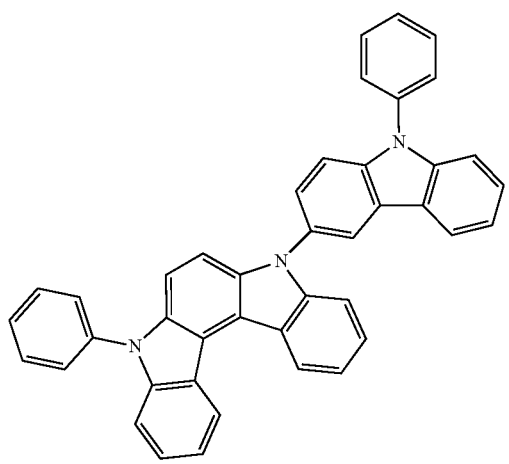
-continued
H-34
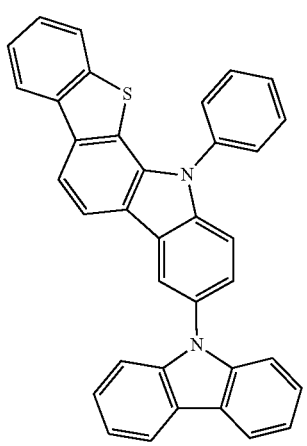
H-35
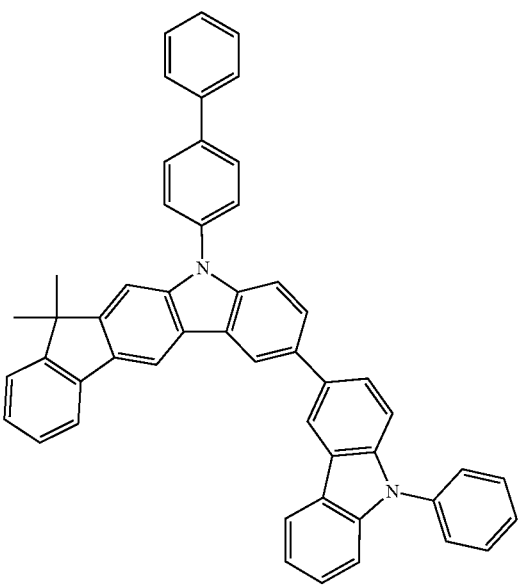
H-36
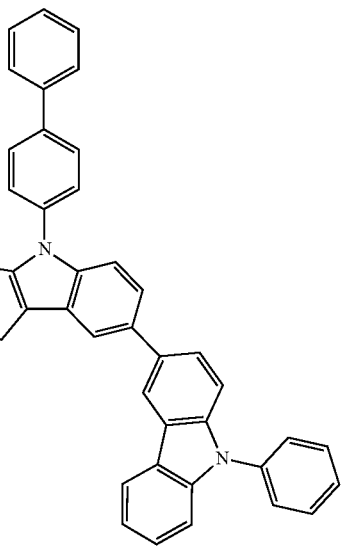

H-37
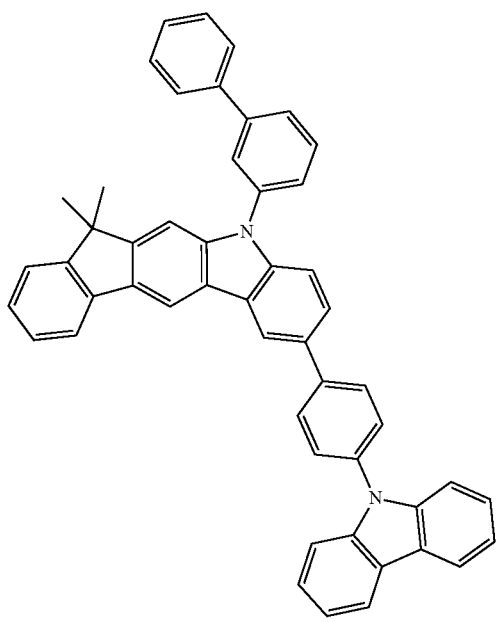
H-38
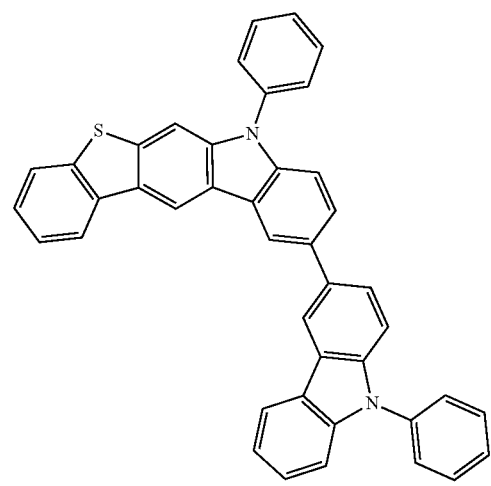
H-39
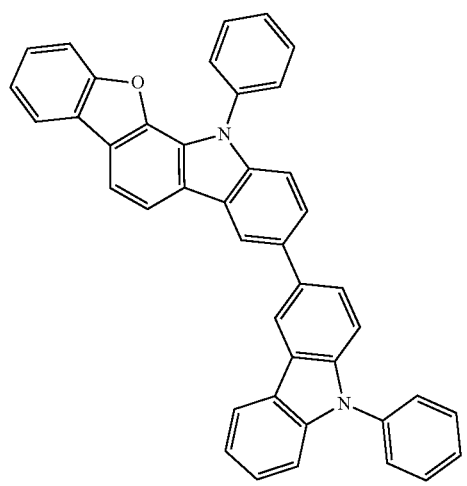
H-40
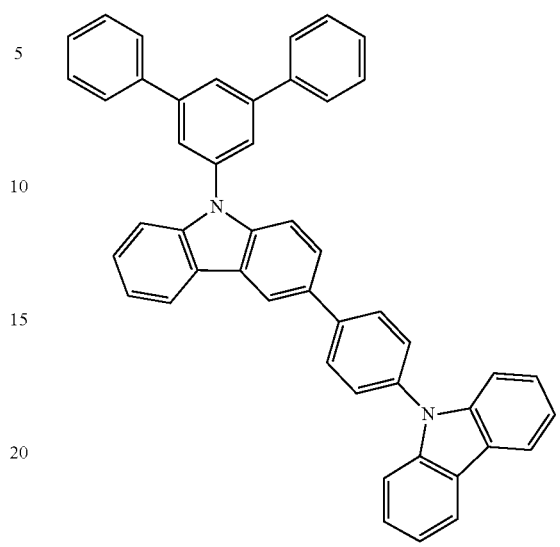
H-41
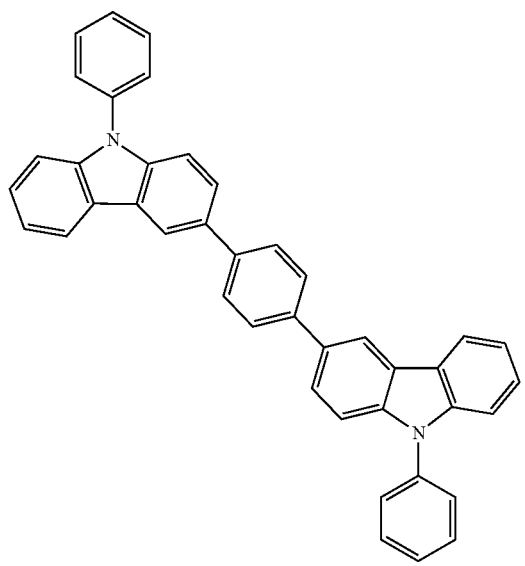

-continued
H-42
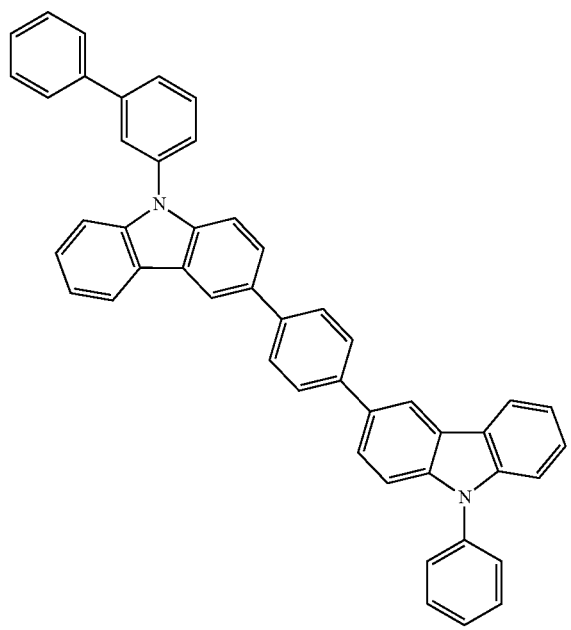
H-43
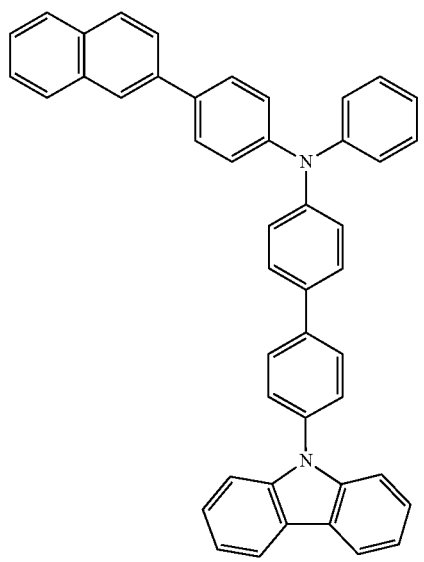
H-44
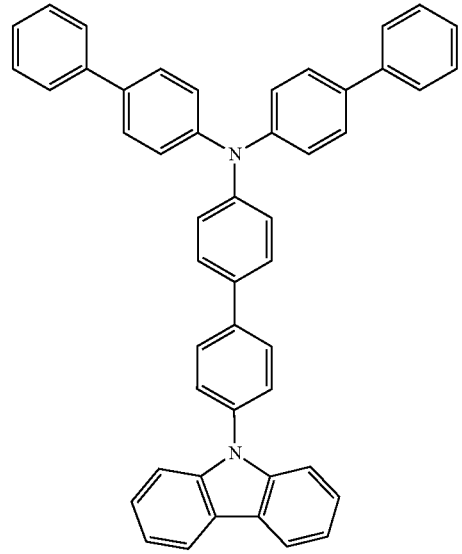
H-45
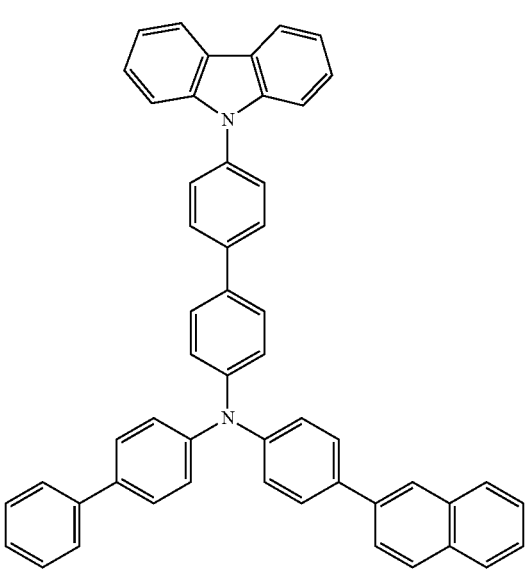
H-46
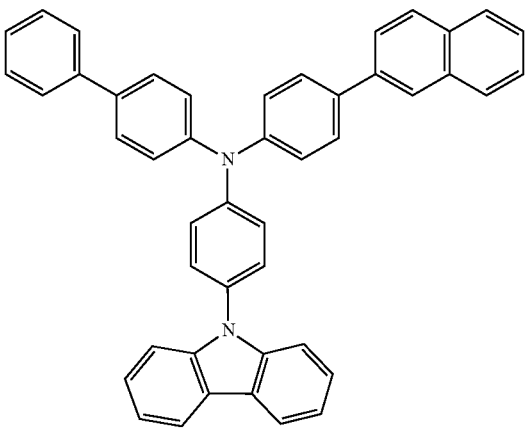

H-47
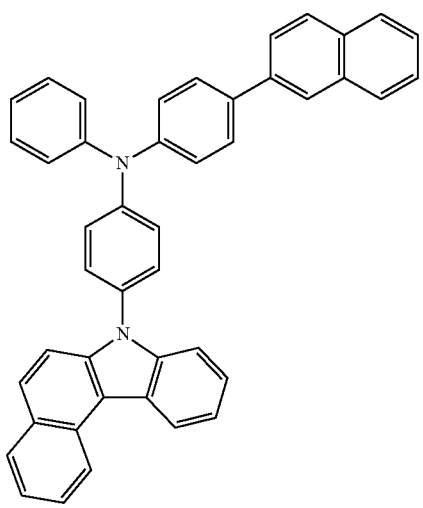
H-48
H-49
H-50
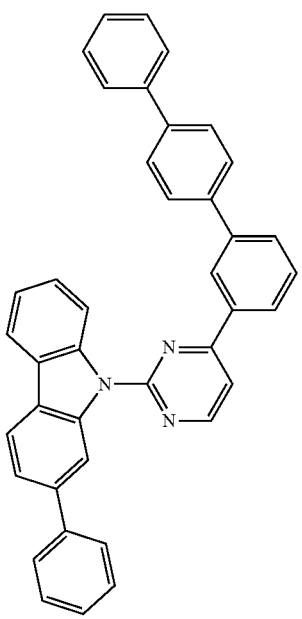
H-51
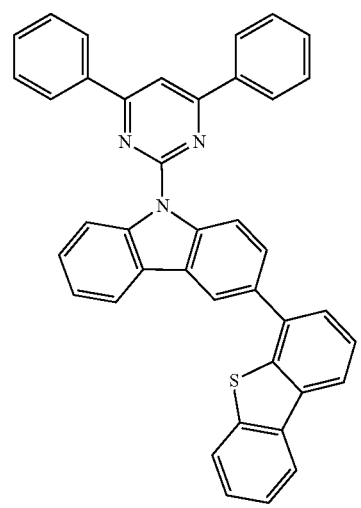
H-52
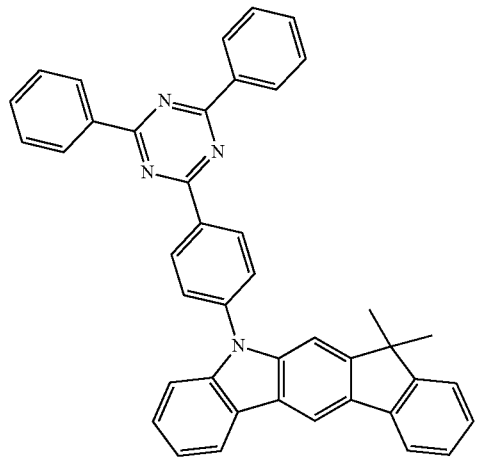

-continued
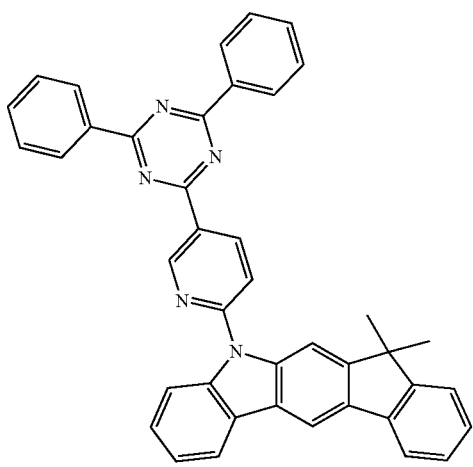
H-53
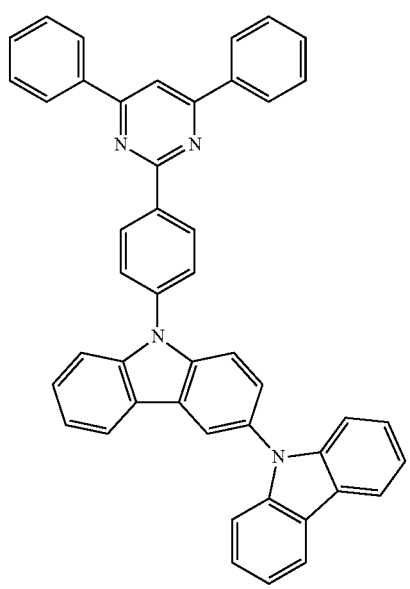
H-54
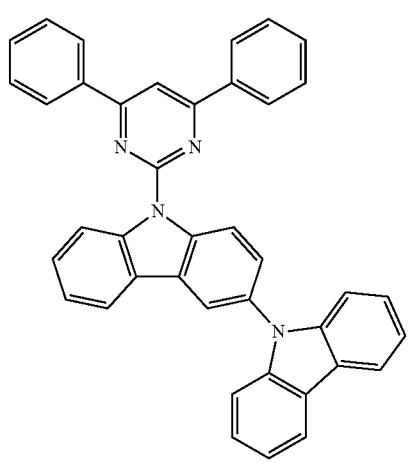
H-55
-continued
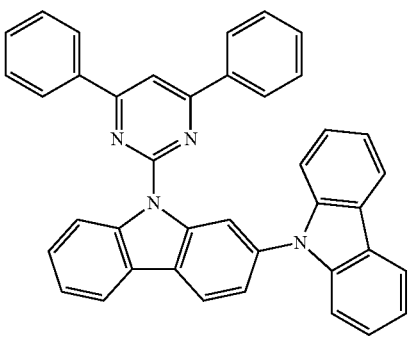
H-56
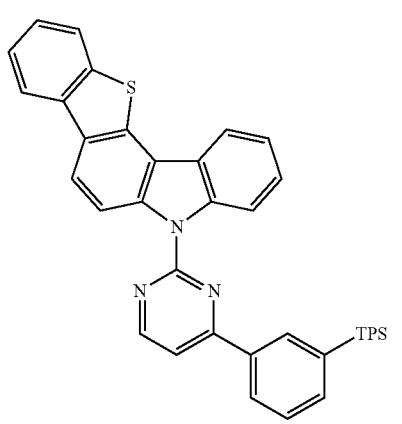
H-57
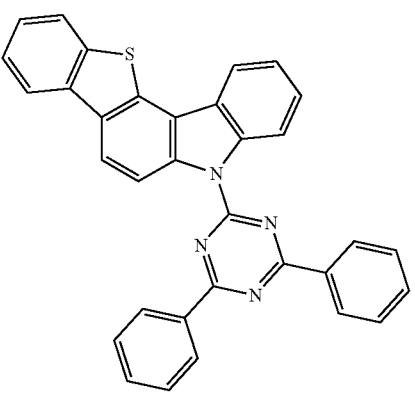
H-58
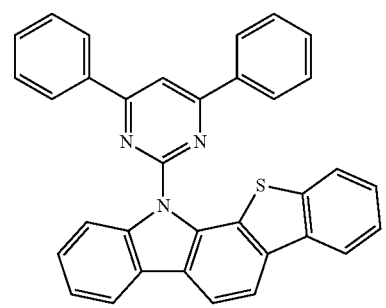
H-59

H-60
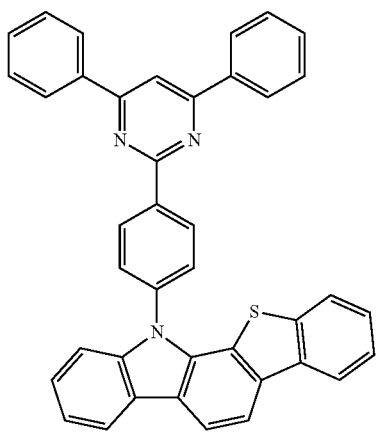
H-61
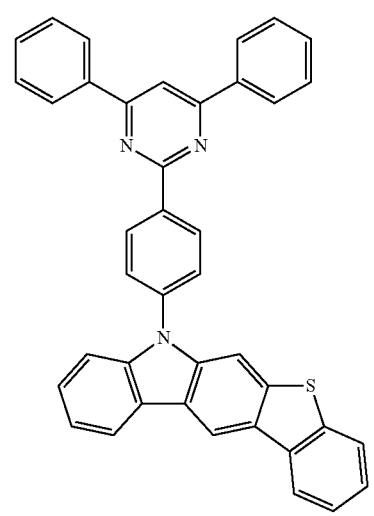
H-62
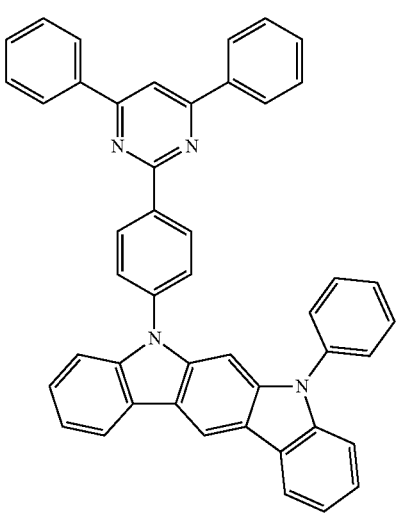
H-63
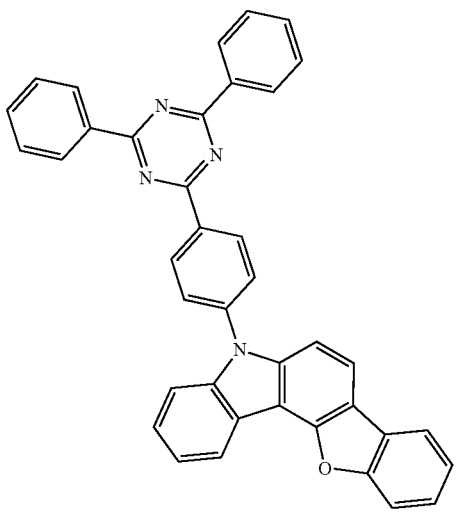
H-64
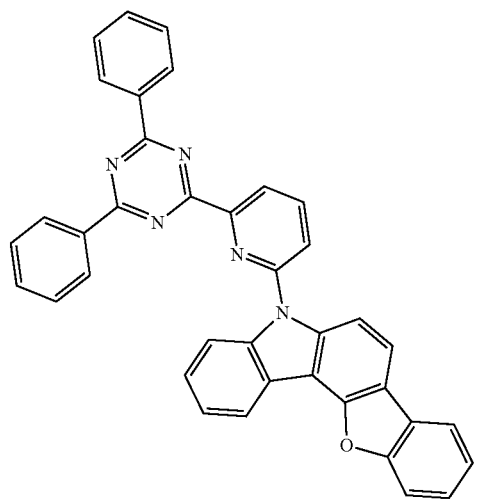
H-65
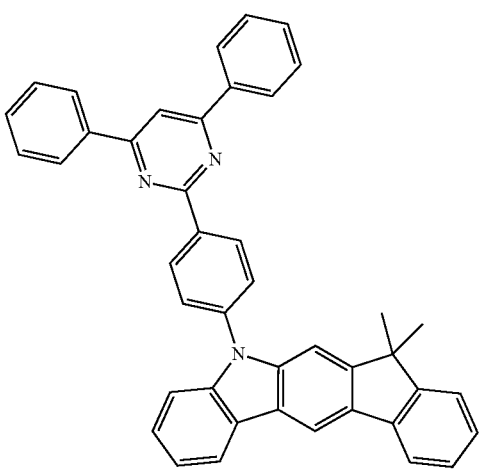

H-66
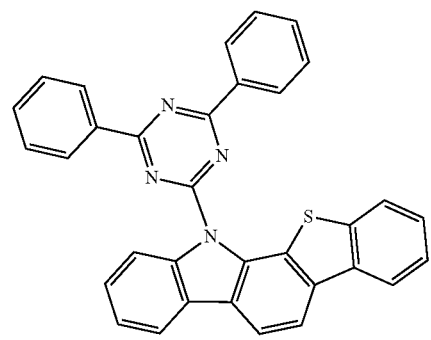
H-67
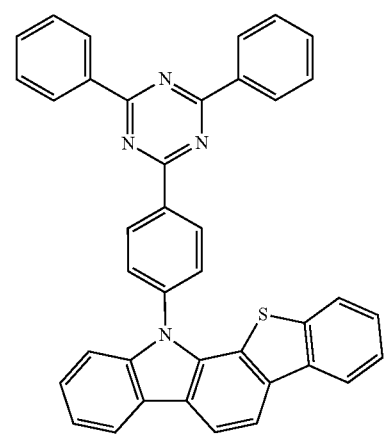
H-68
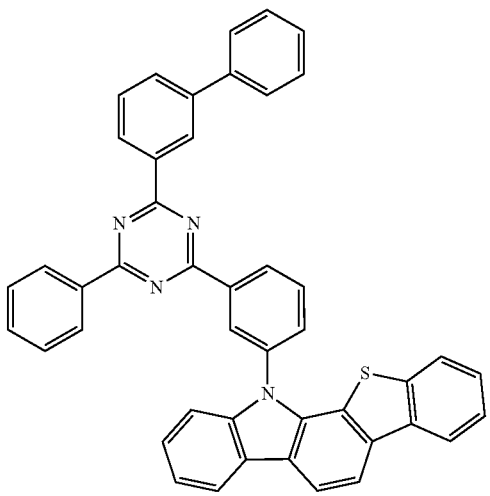
H-69
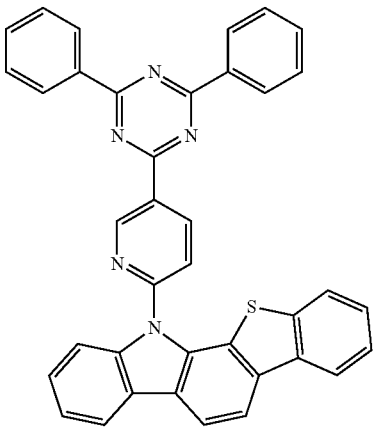
H-70
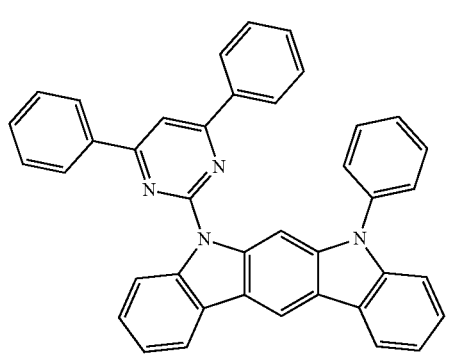
H-71
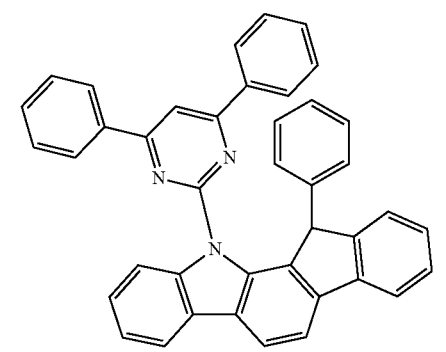
H-72
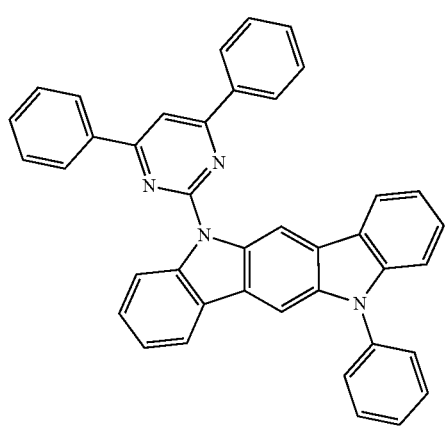

H-73
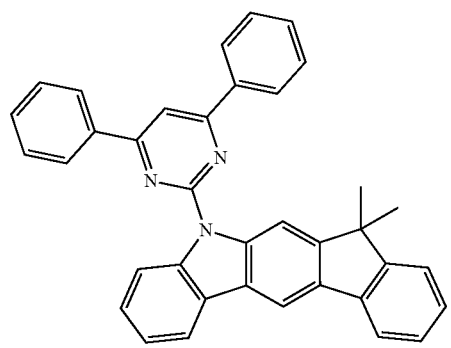
H-74
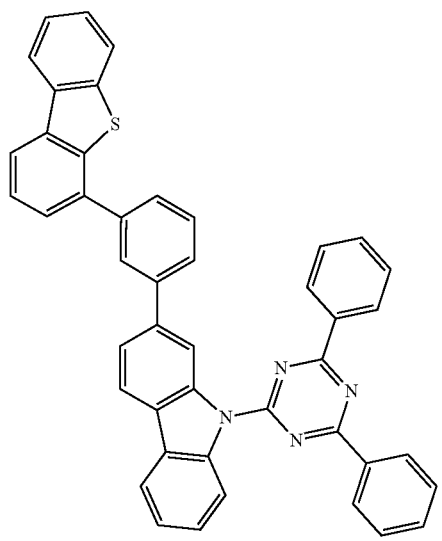
H-75
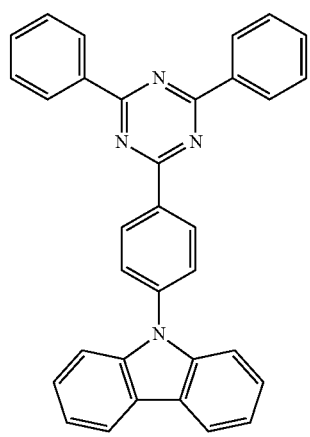
H-76
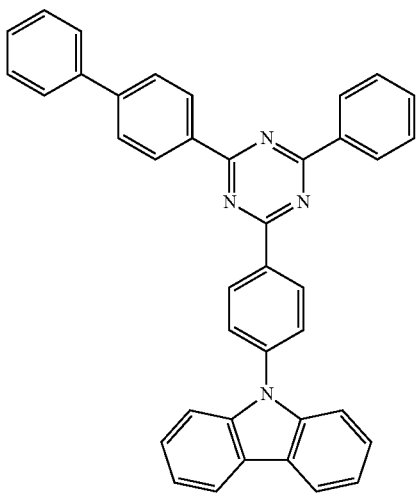
H-77
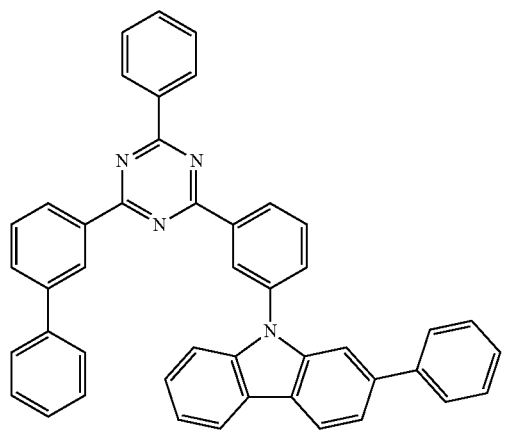
H-78
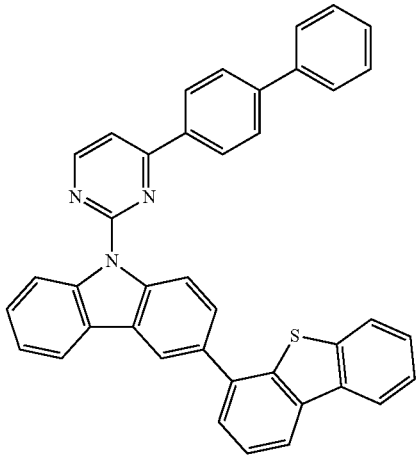

-continued
H-79
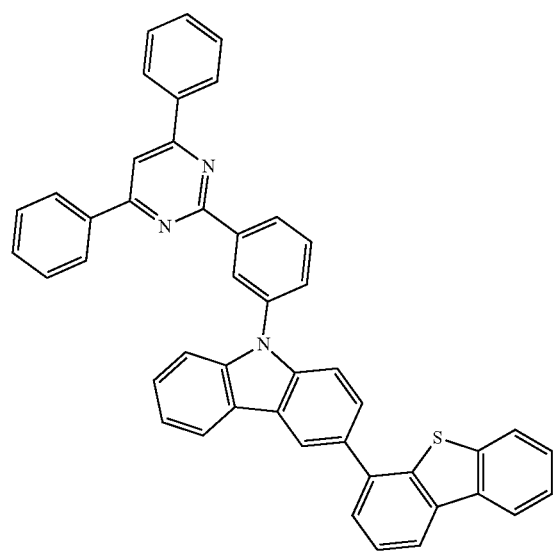
H-80
H-82
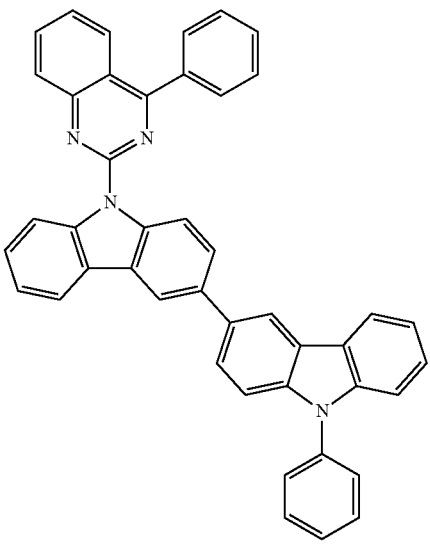
H-83
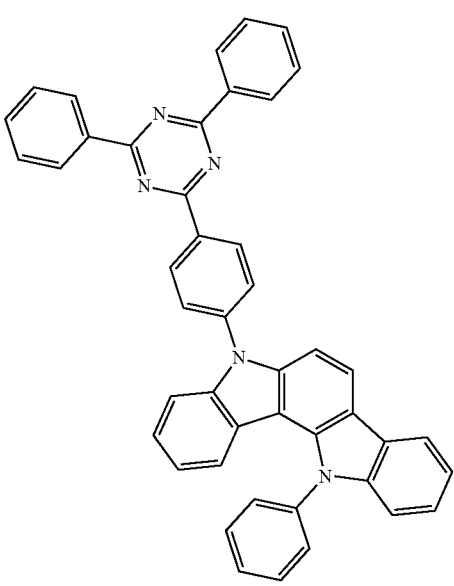
H-81
H-84
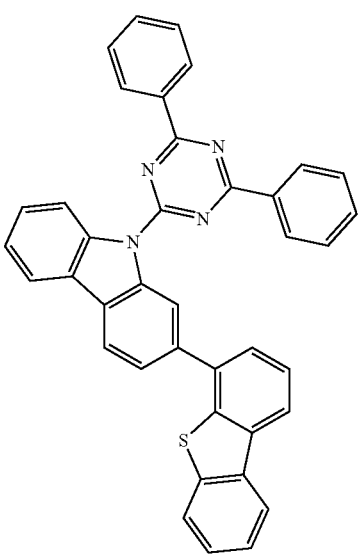

H-85
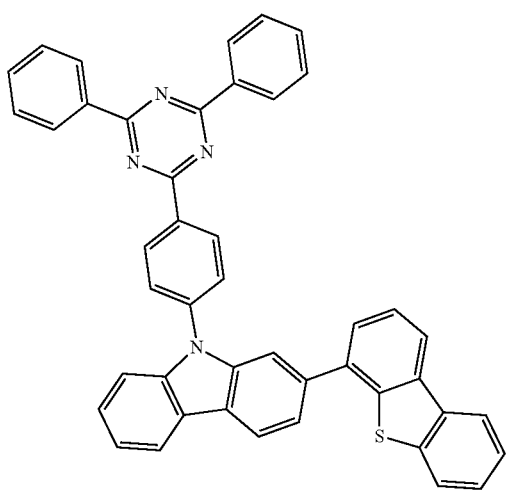
H-86
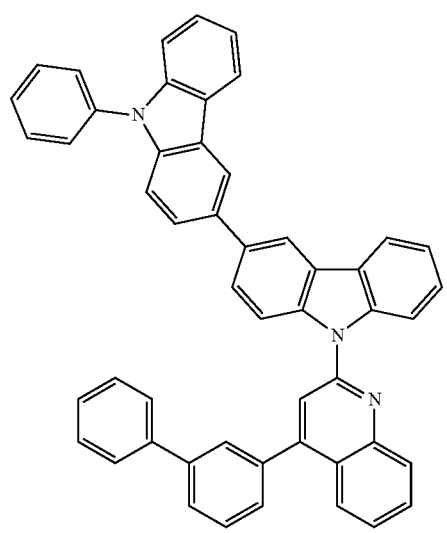
H-87
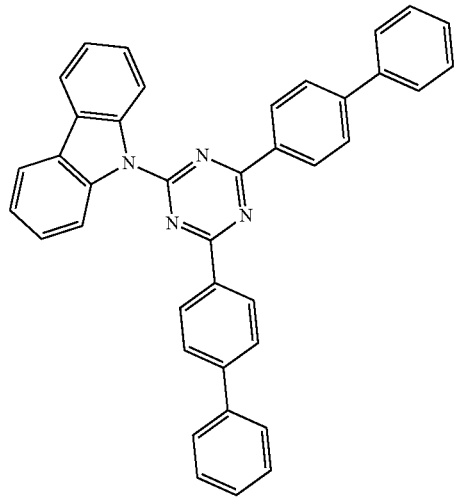
H-88
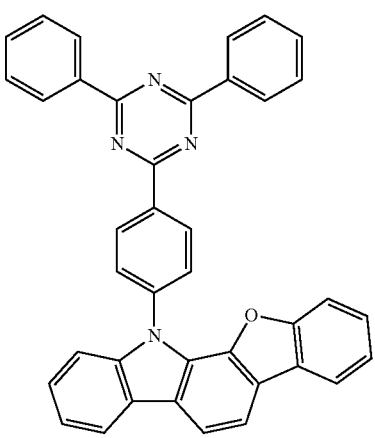
H-89
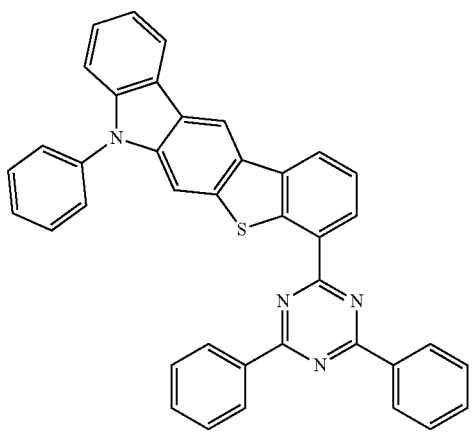
H-90
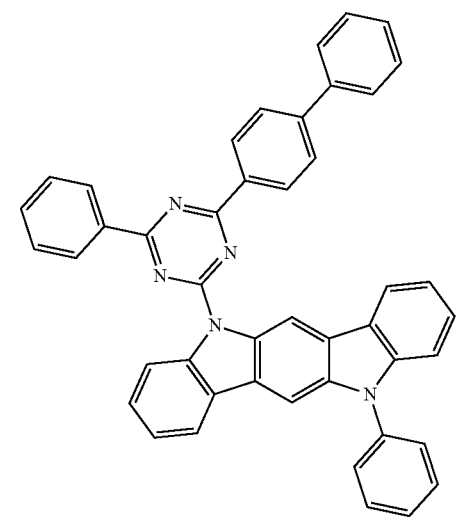

-continued
H-91
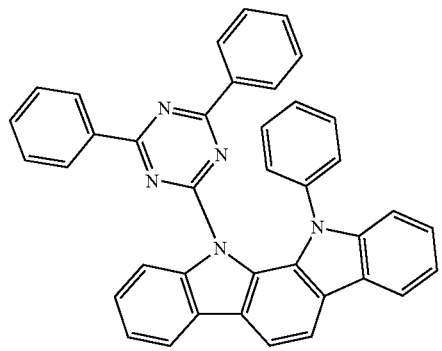
H-92
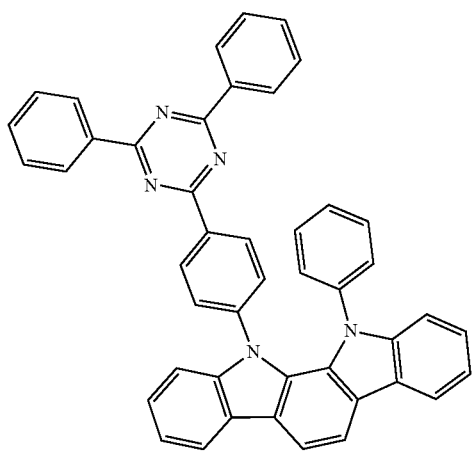
H-93
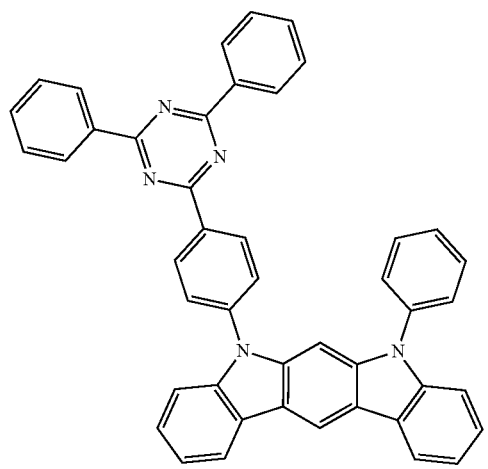
-continued
H-94
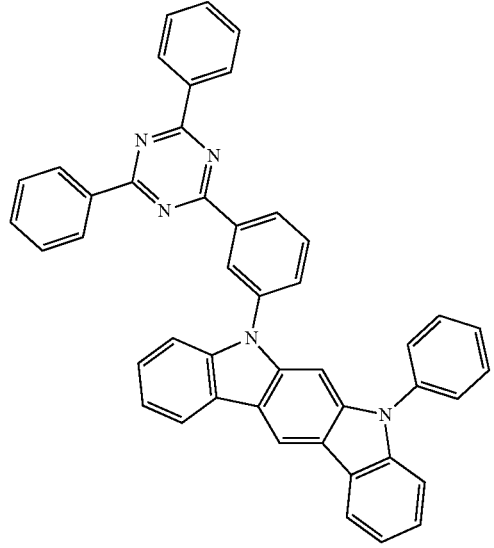
H-95
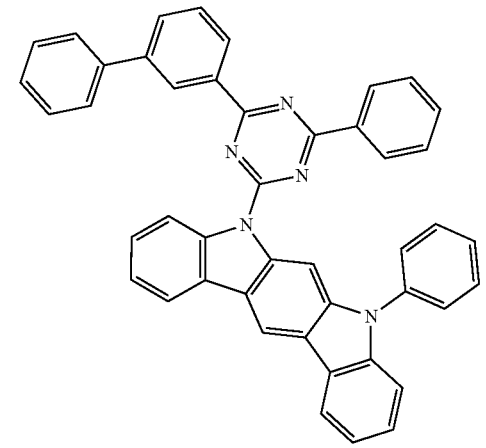
H-96
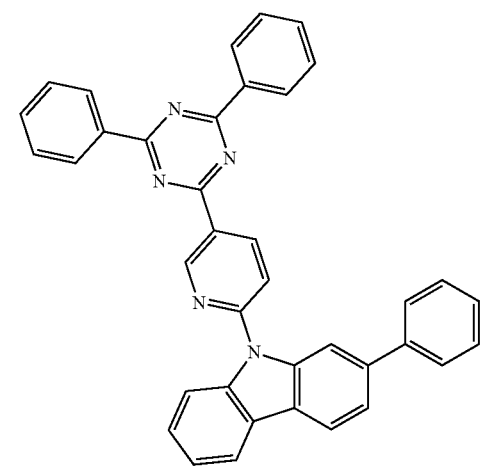

H-97
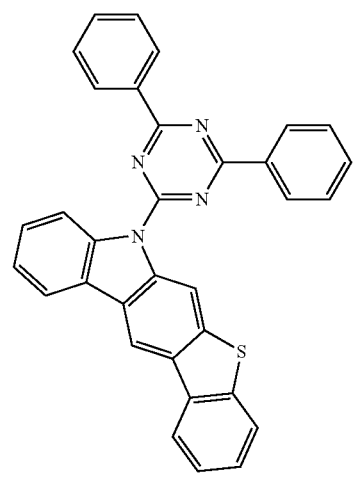
H-98
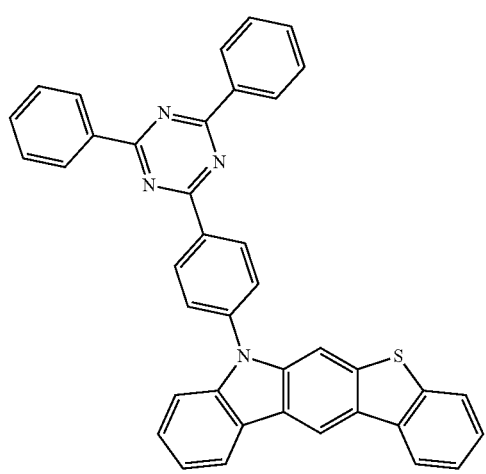
H-99
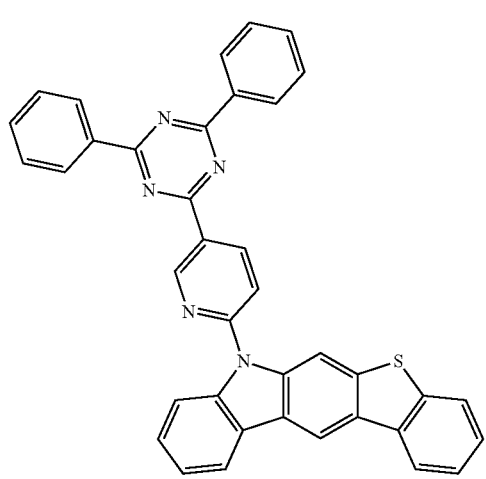
H-100
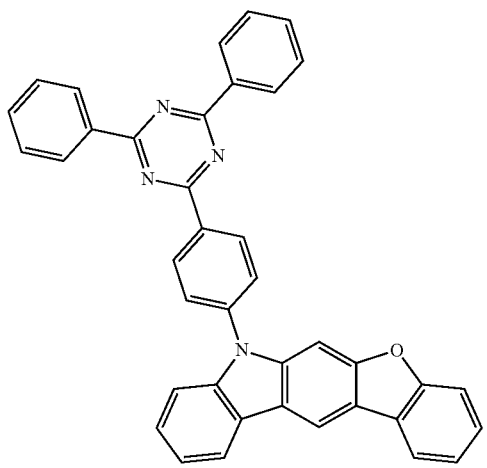
H-101
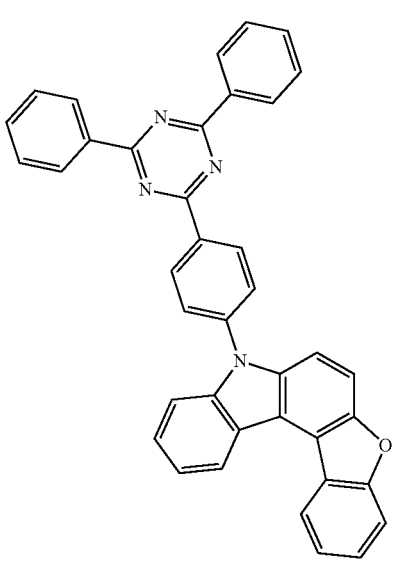
H-102
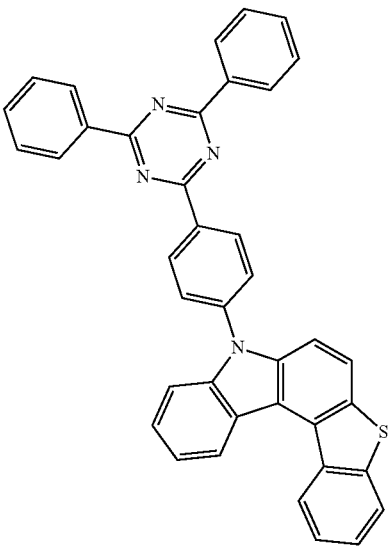

H-103
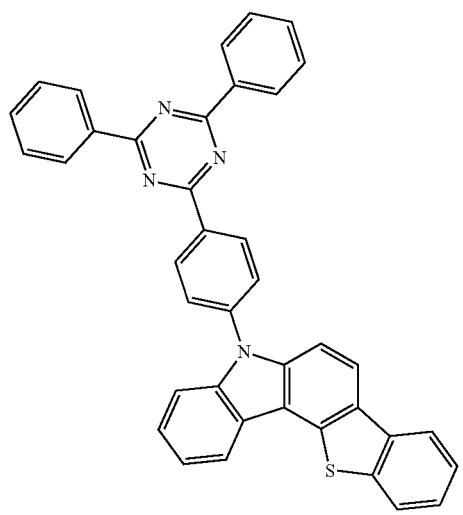
H-104
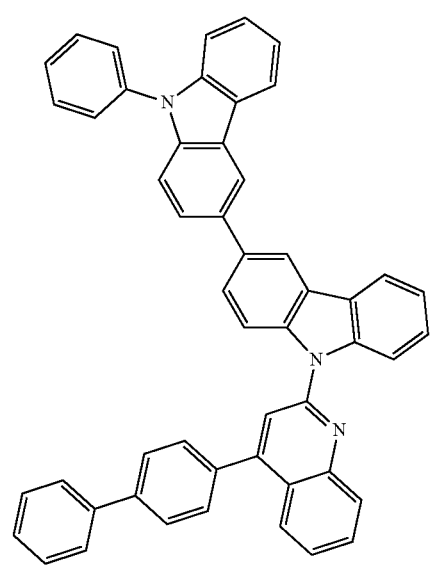
H-105
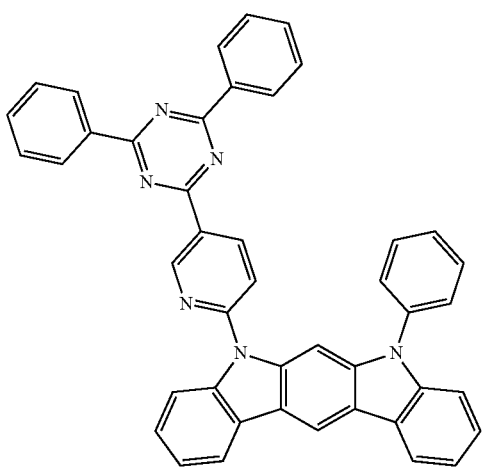
H-106
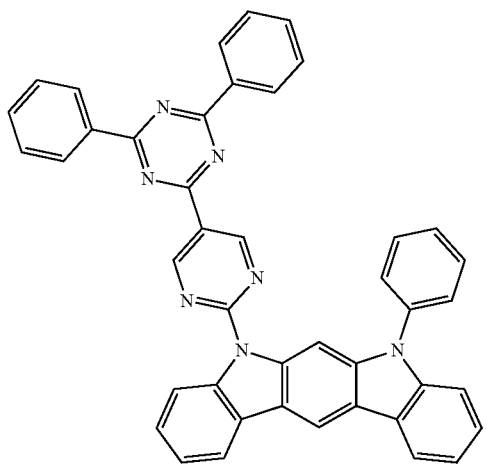
H-107
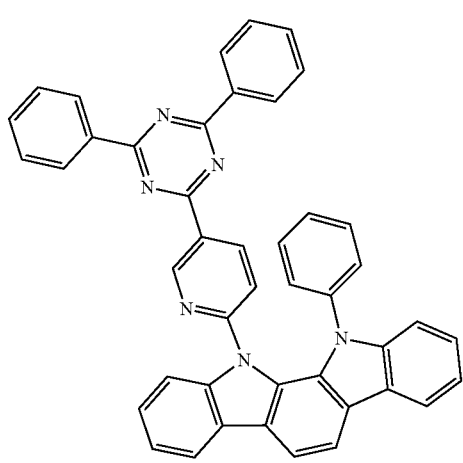
H-108
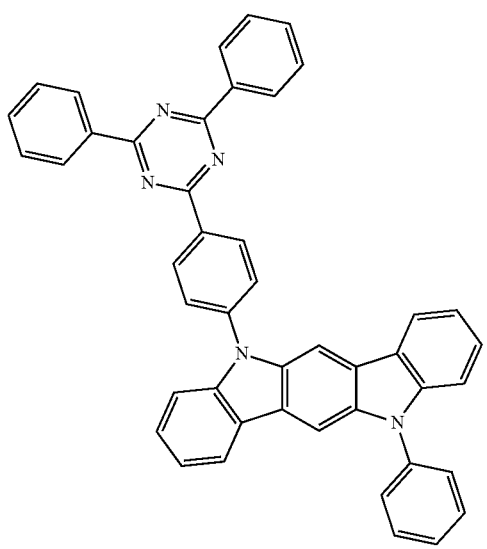

H-109
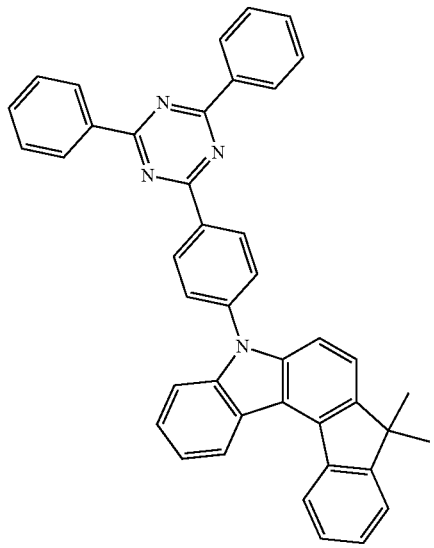
H-110
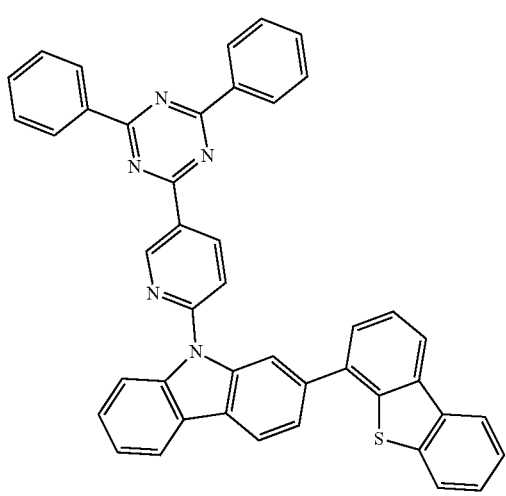
H-111
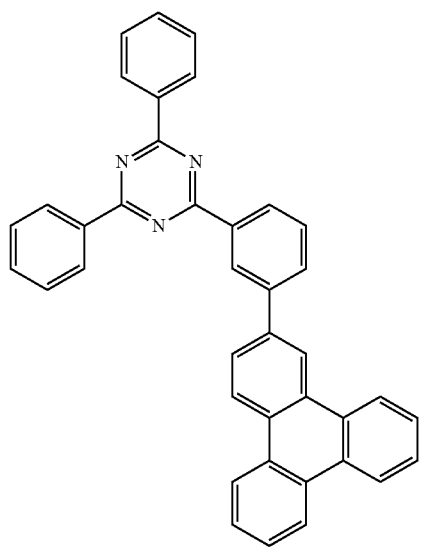
H-112
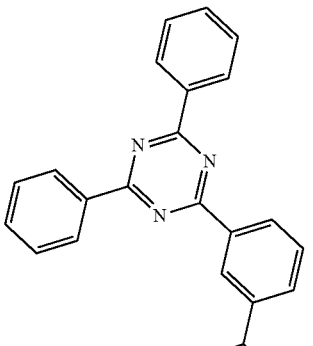
H-113
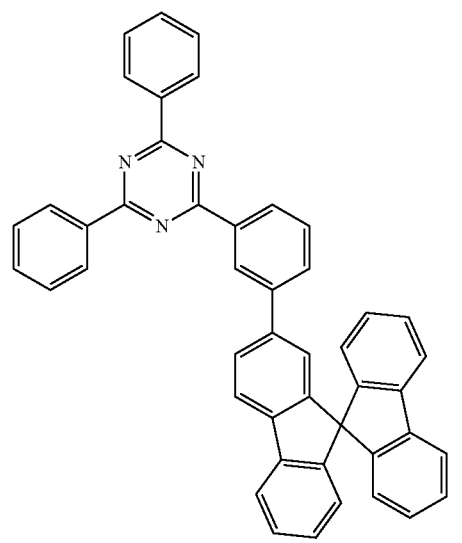
H-114
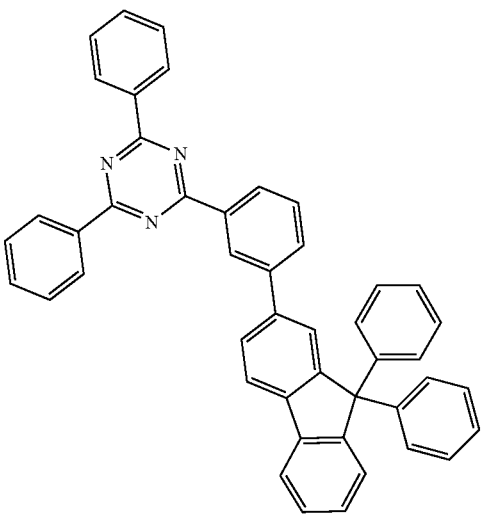

H-115
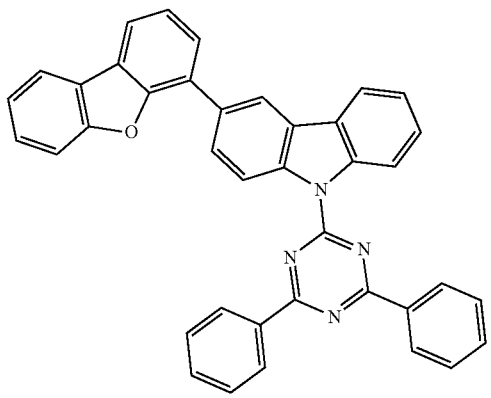
H-116
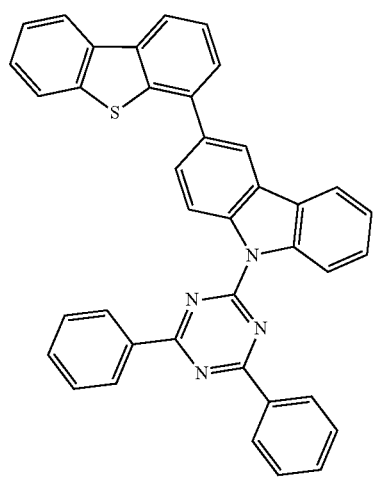
H-117
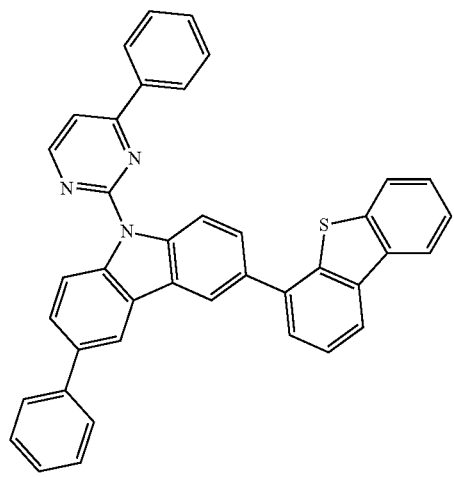
H-118
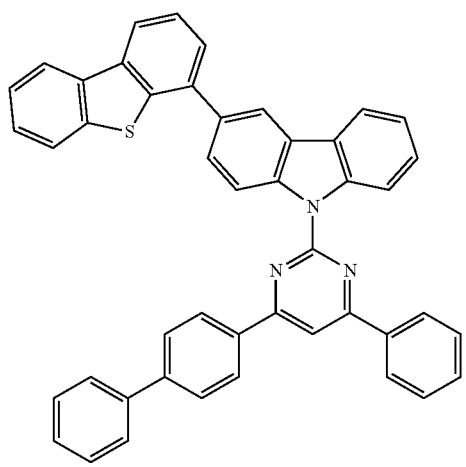
H-119
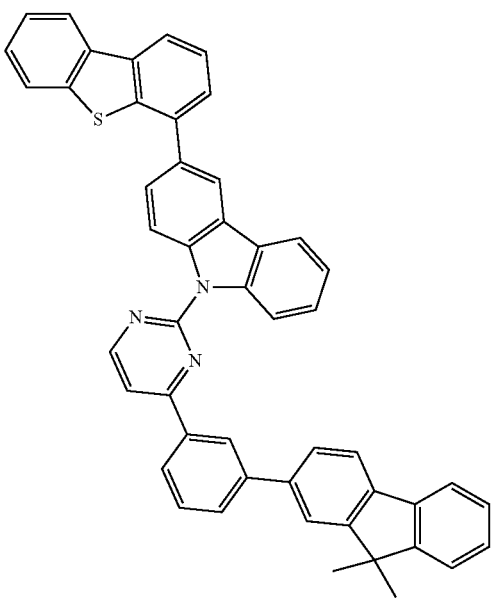
H-120
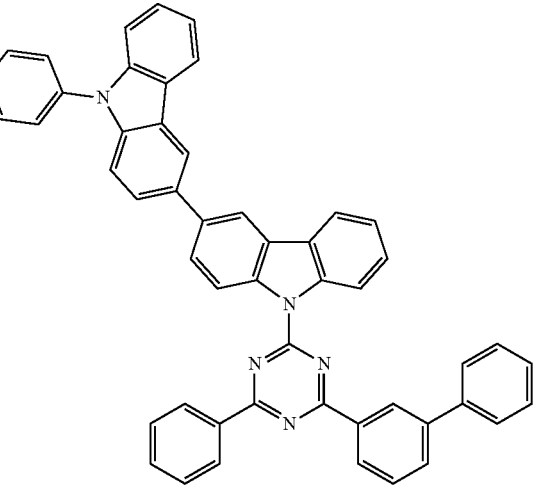

H-121
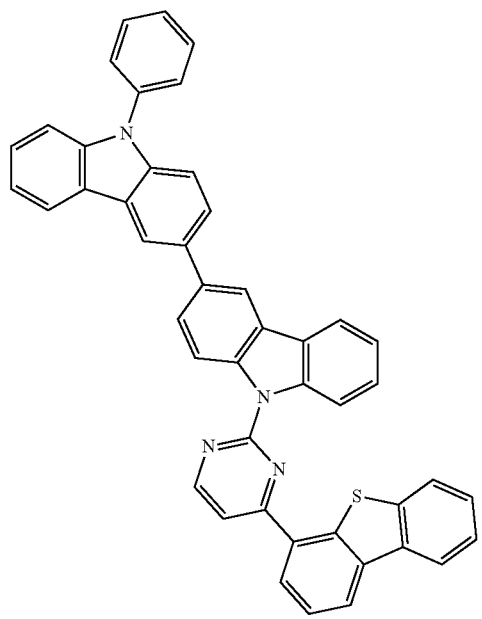
H-123
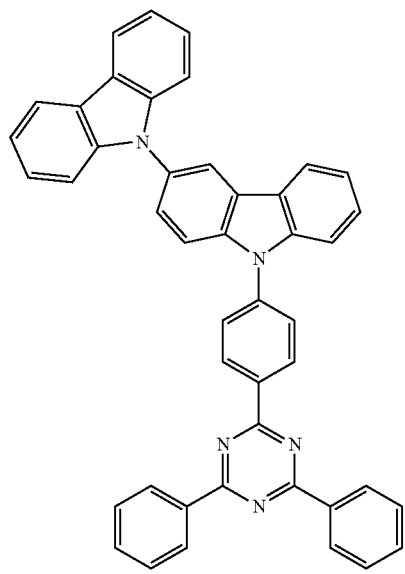
H-122
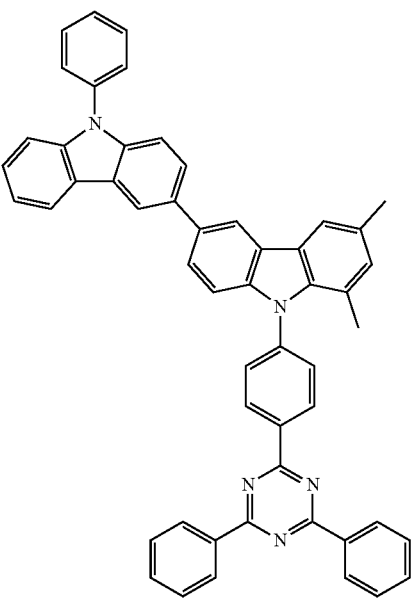
H-124

H-125
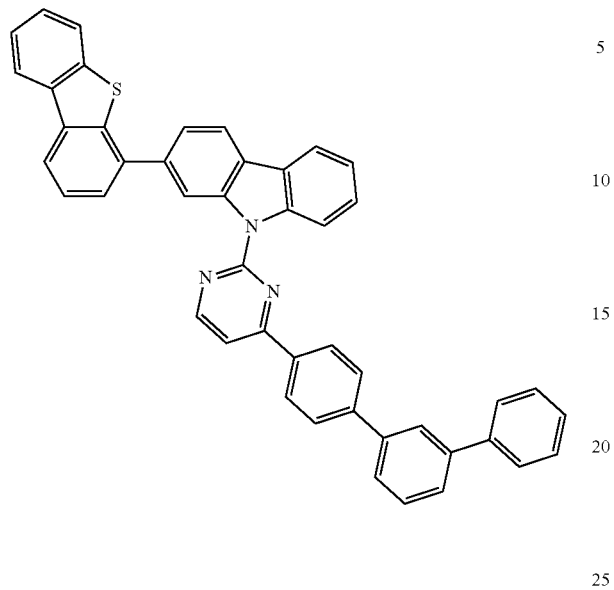
H-127
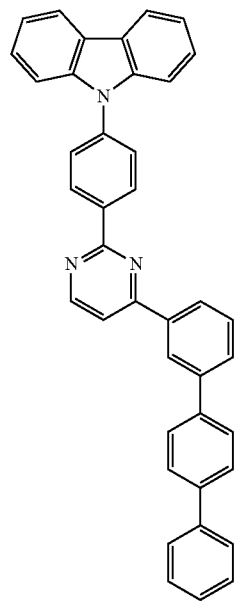
H-126
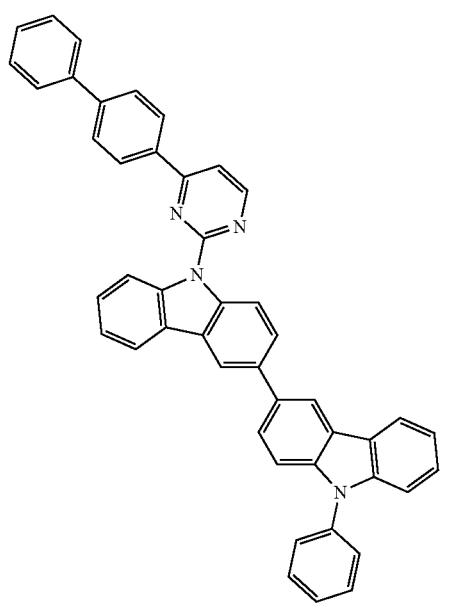
H-128
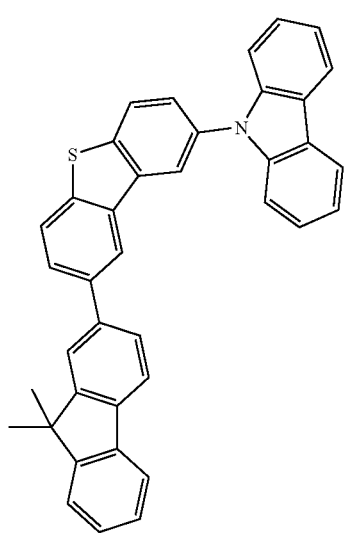

H-129
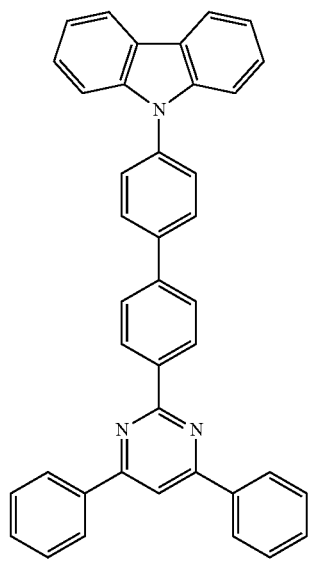
H-130
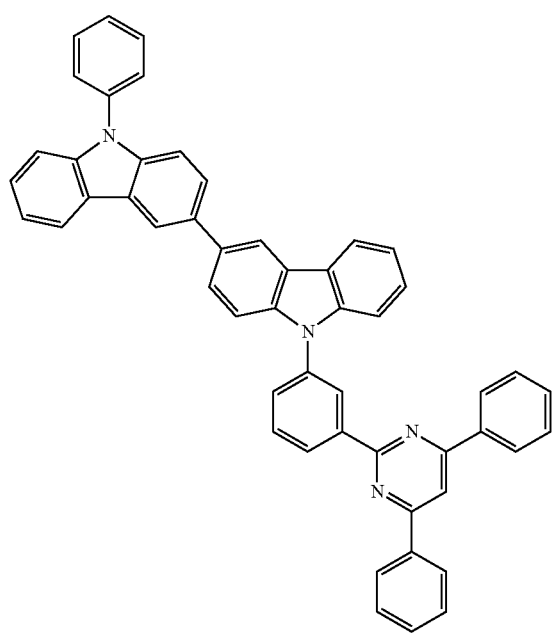
H-131
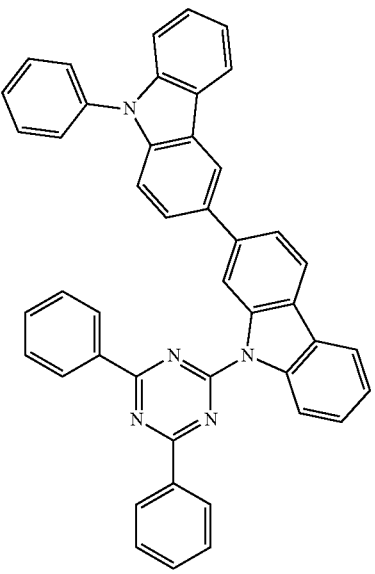
H-132
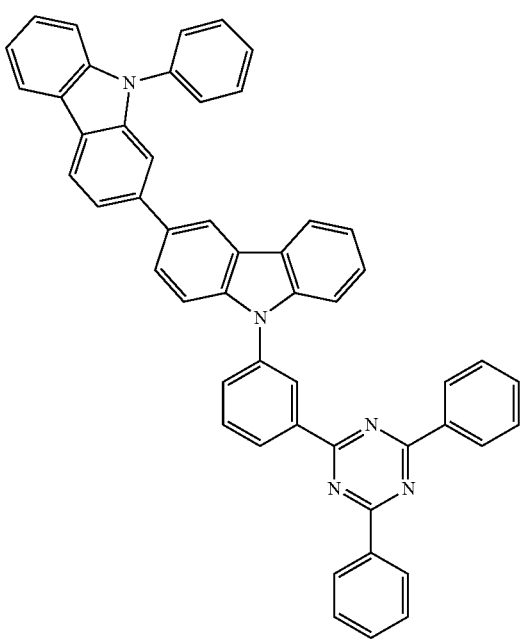

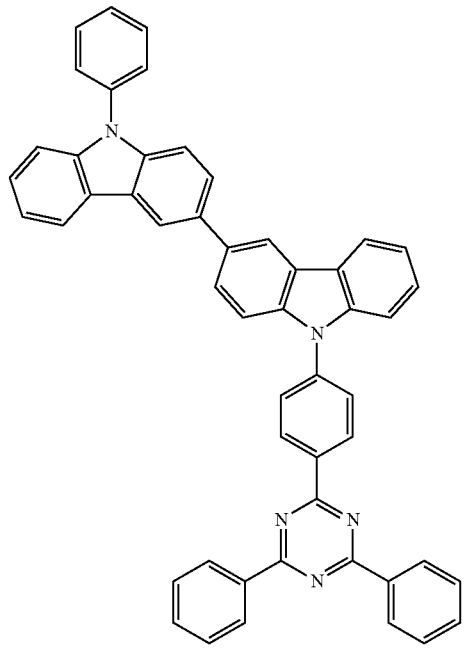
H-133
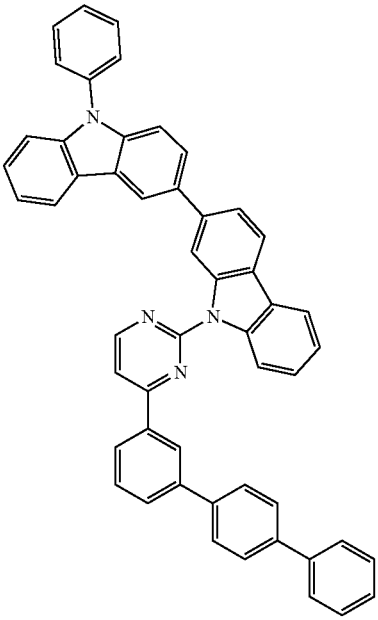
H-135
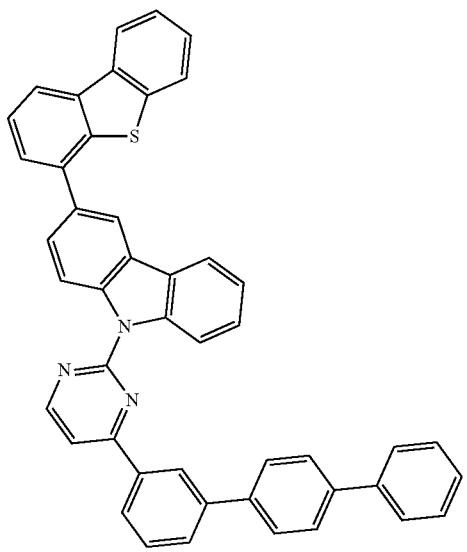
H-134
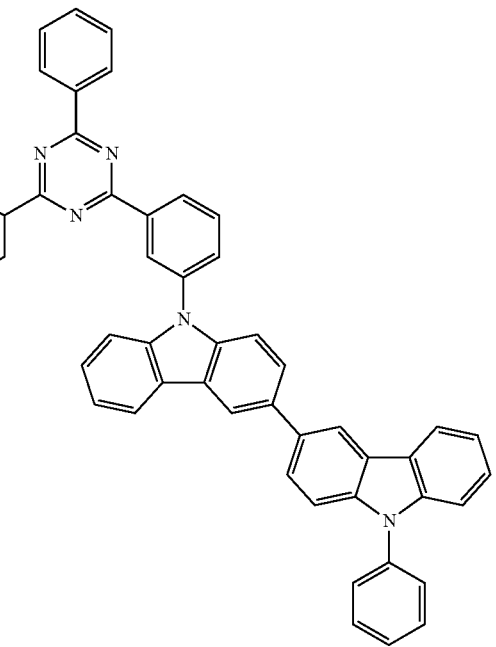
H-136

H-137
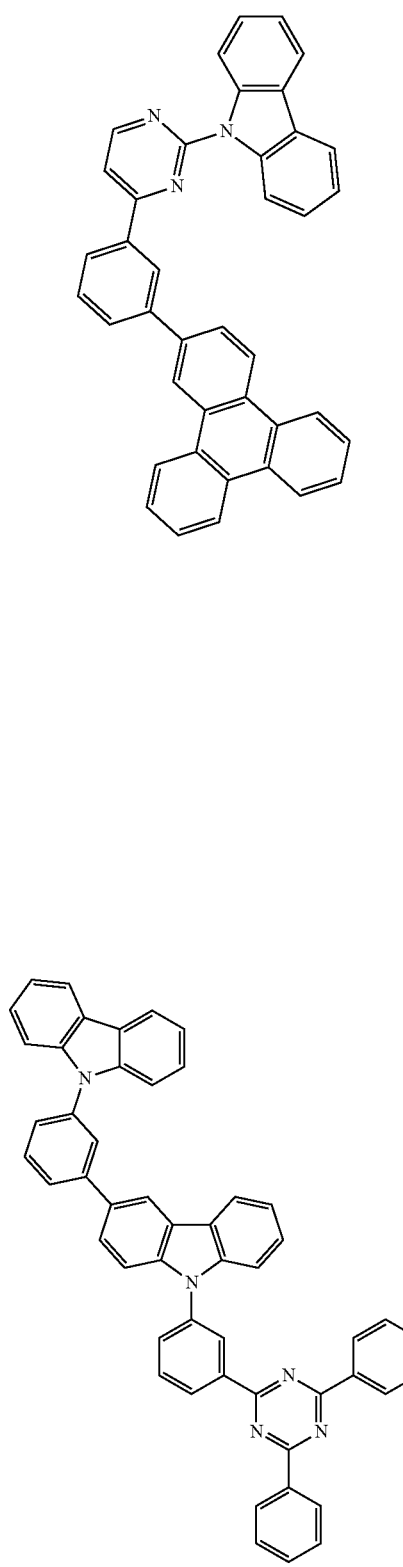
H-138
H-139
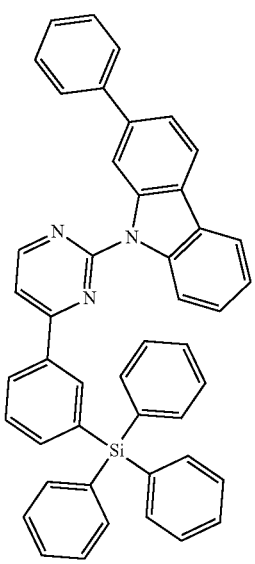
H-140
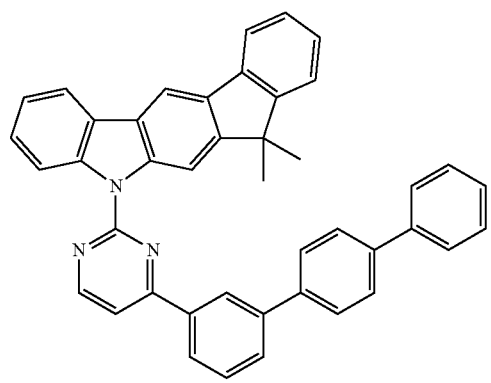
H-141
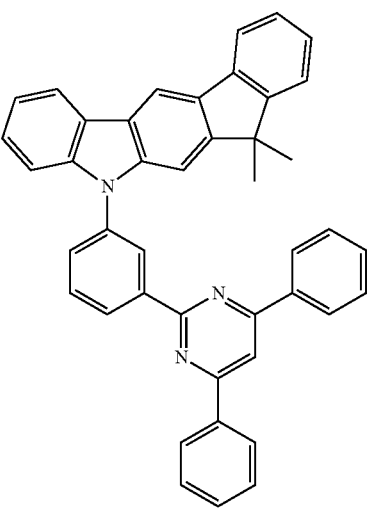

H-142
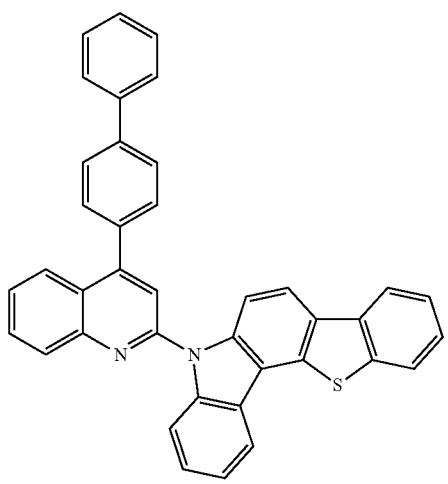
H-143
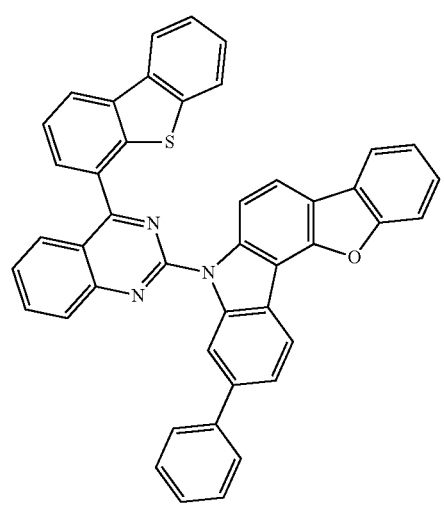
H-144
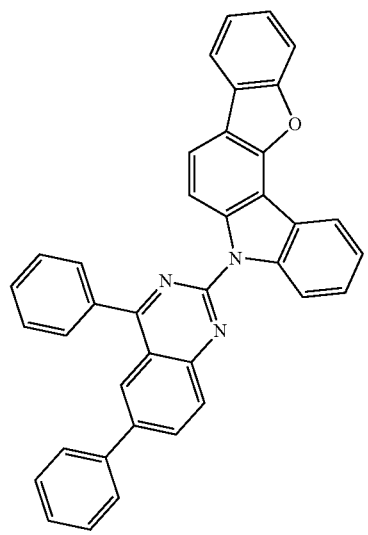
H-145
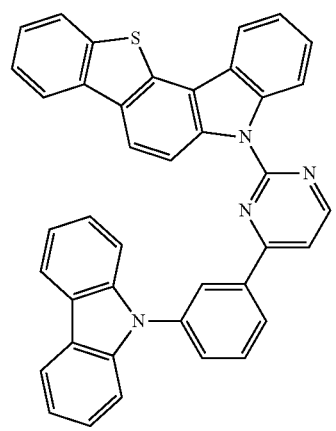
H-146
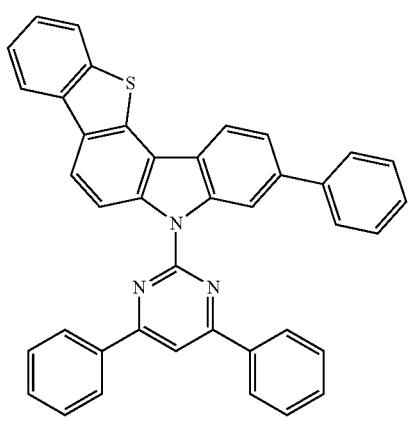
H-147
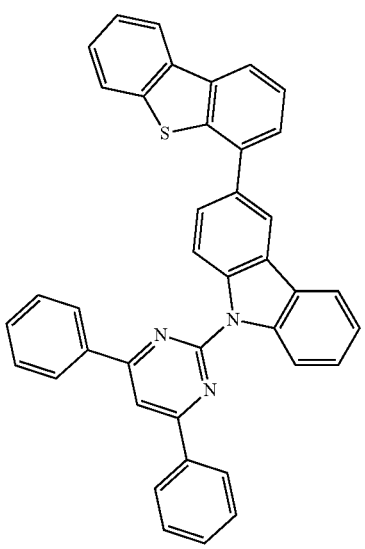

H-148
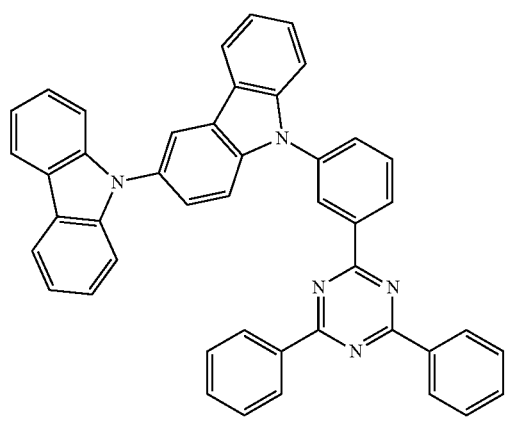
H-149
H-150
H-151
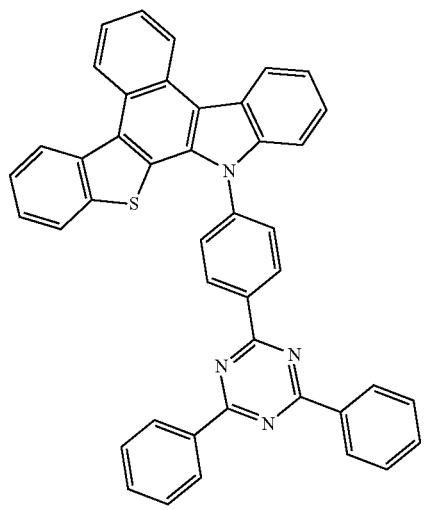
H-152
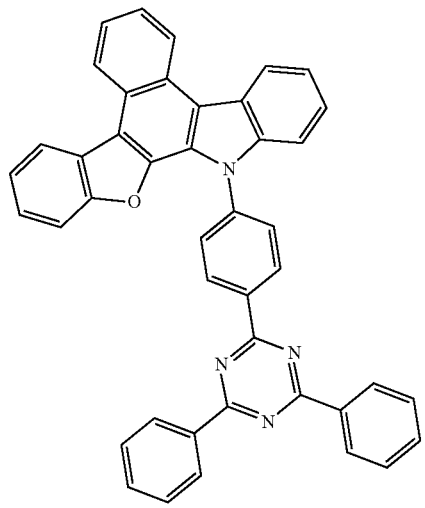
H-153
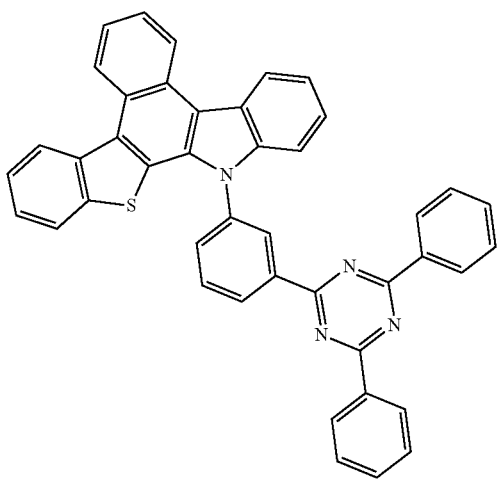

-continued
H-154
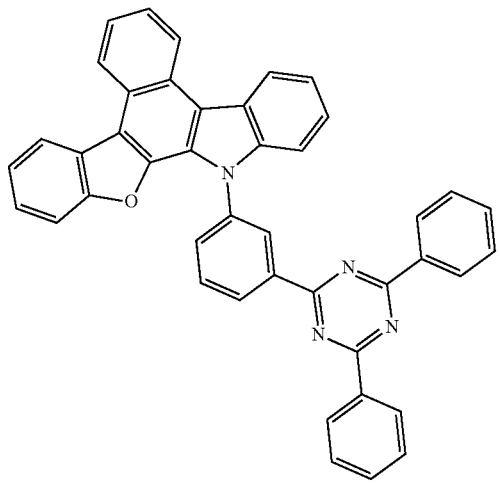
H-155
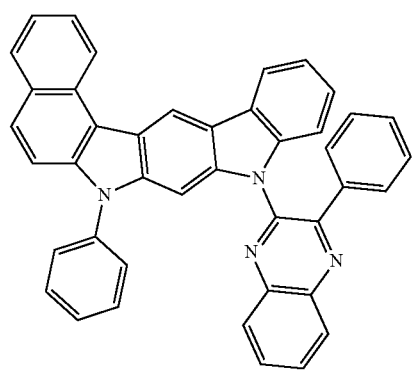
H-156
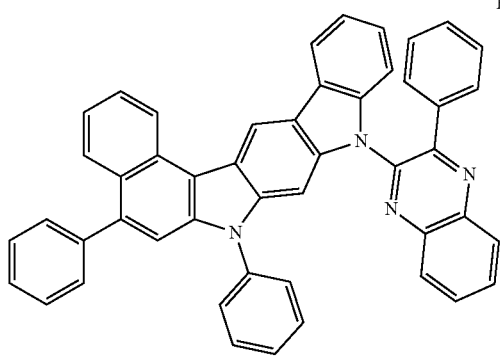
H-157
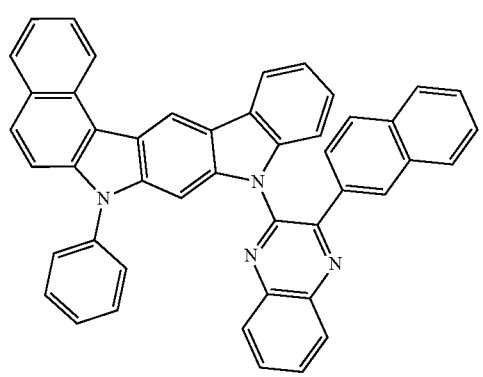
-continued
H-158
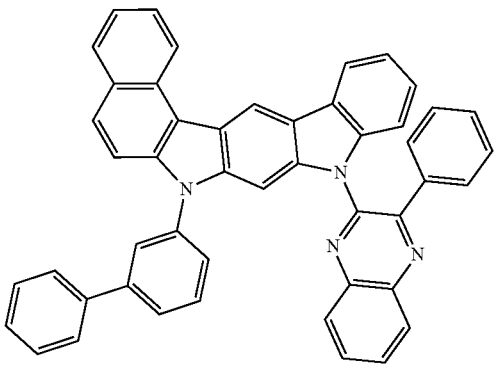
H-159
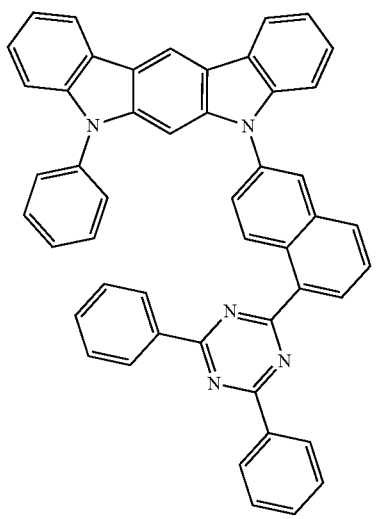
H-160
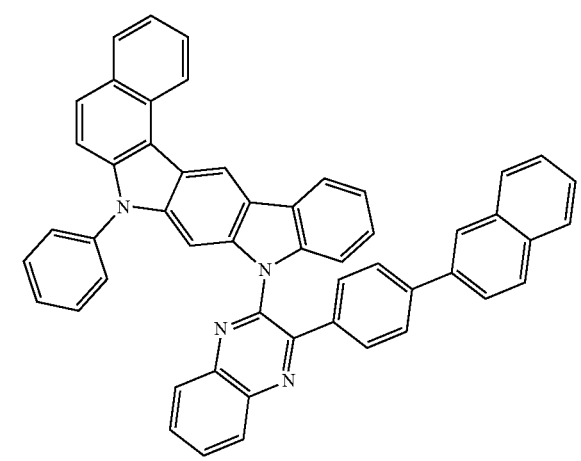

H-161
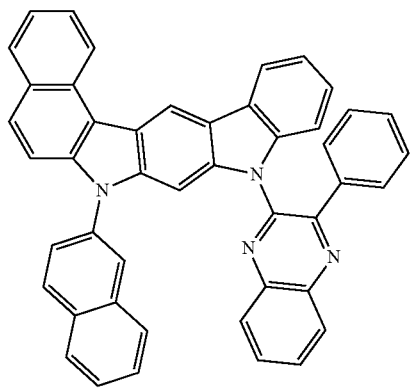
H-162
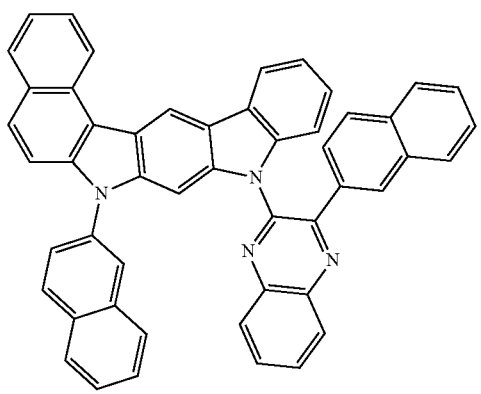
H-163
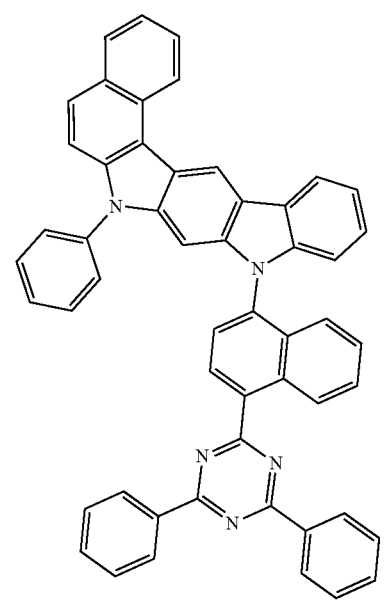
H-164
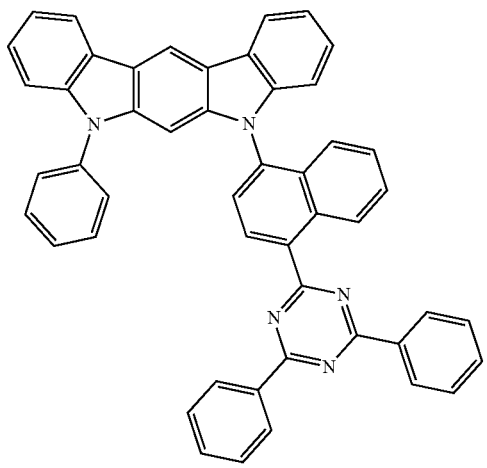
H-165
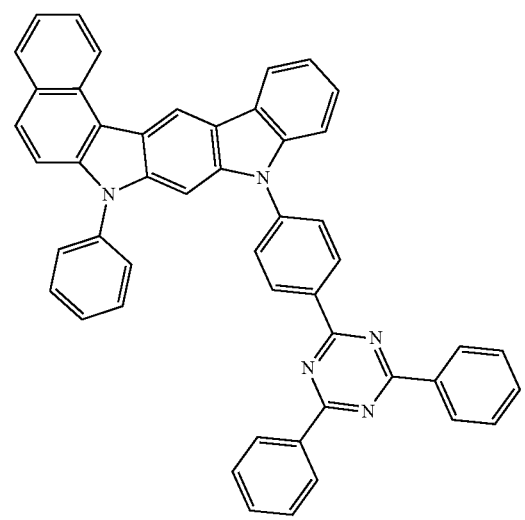
H-166
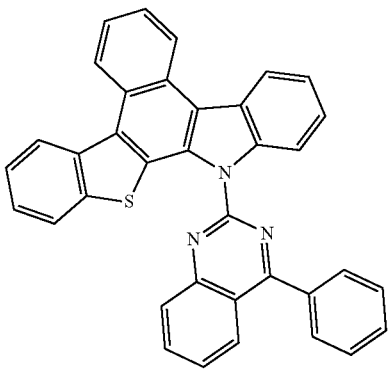

H-167
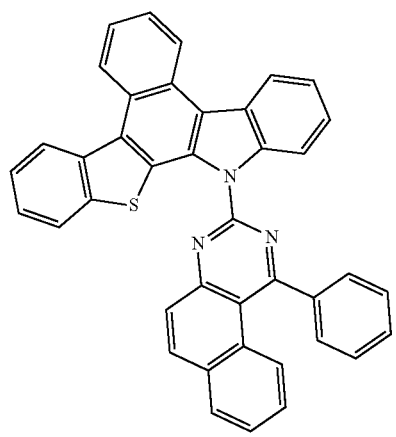
H-168
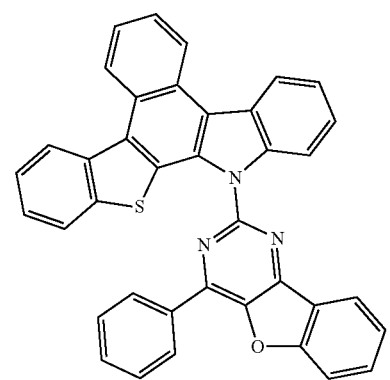
H-169
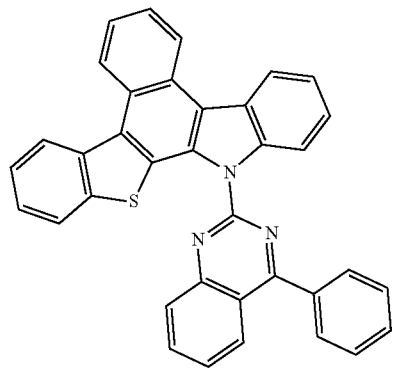
H-170
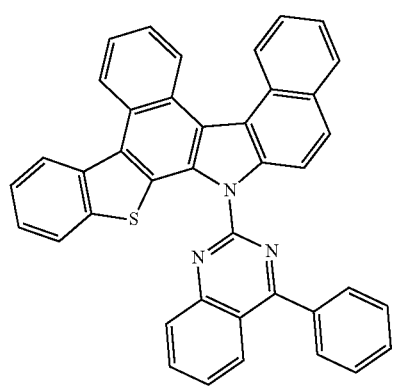
H-171
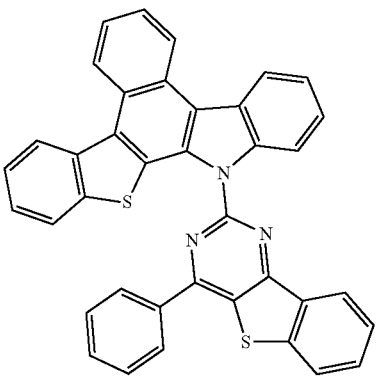
H-172
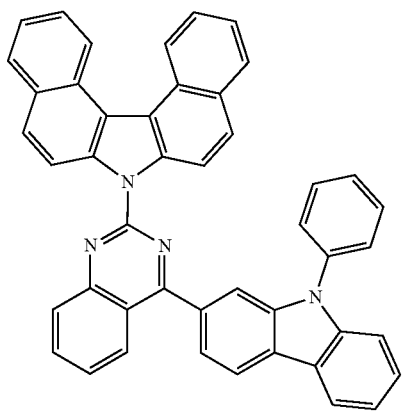
H-173
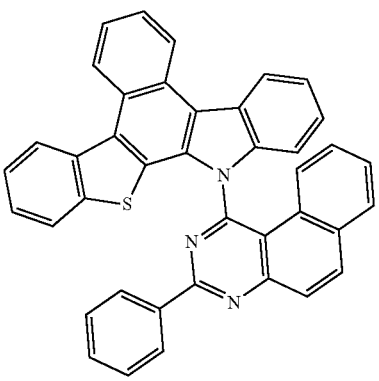
H-174
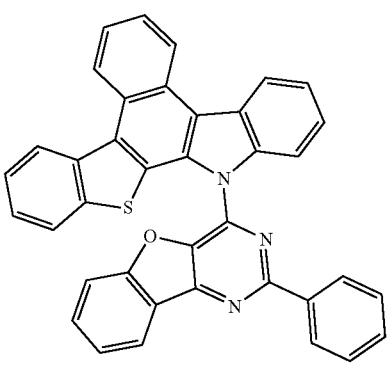

H-175
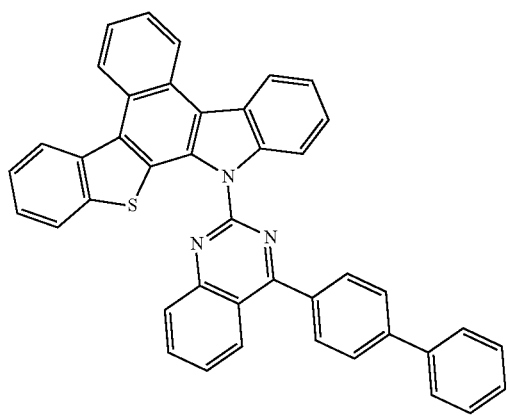
H-176
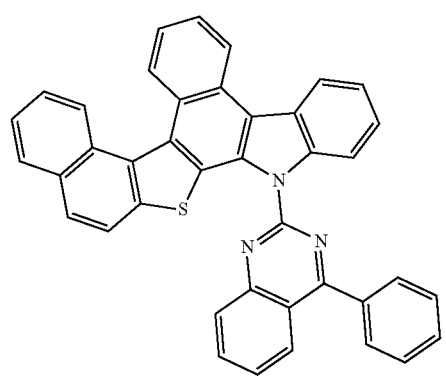
H-177
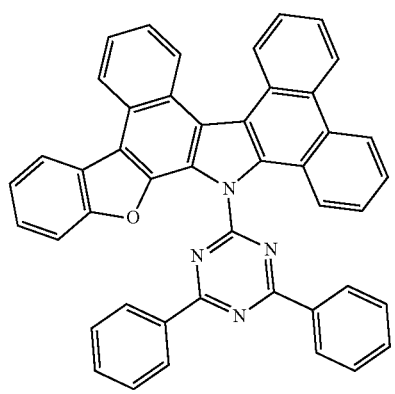
H-178
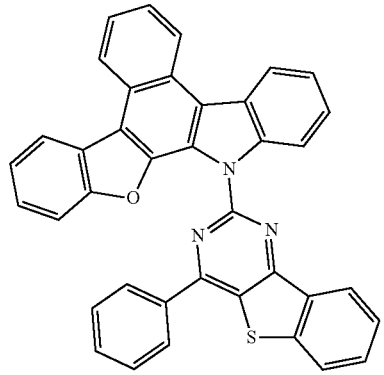
H-179
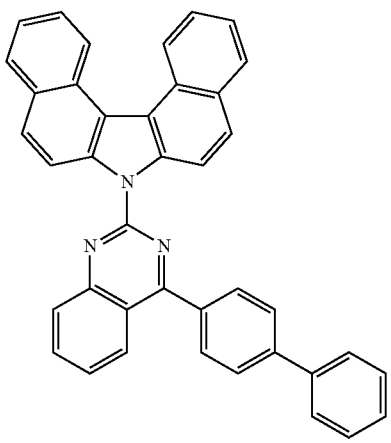
H-180
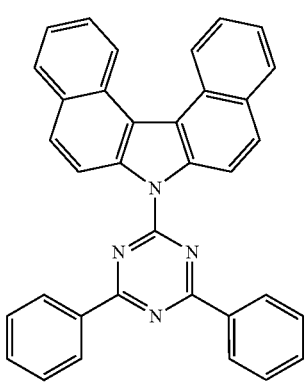
H-181
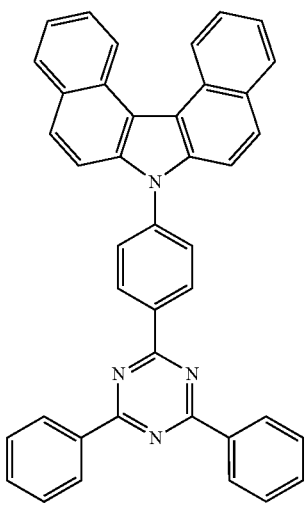

H-182
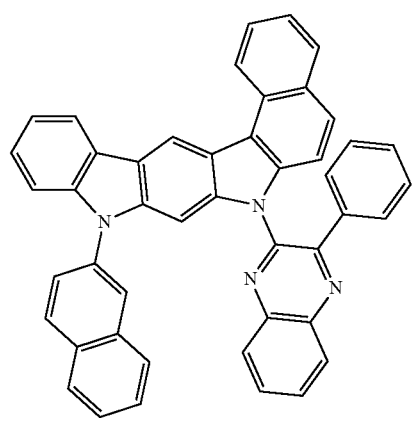
H-183
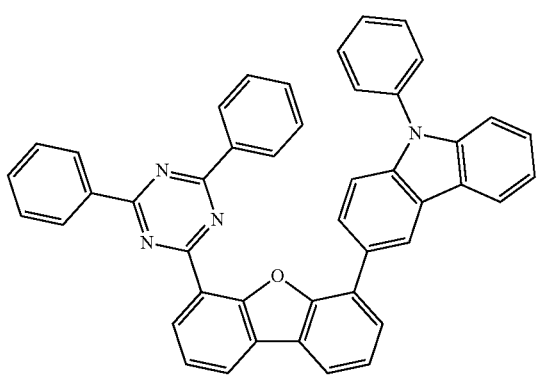
H-184
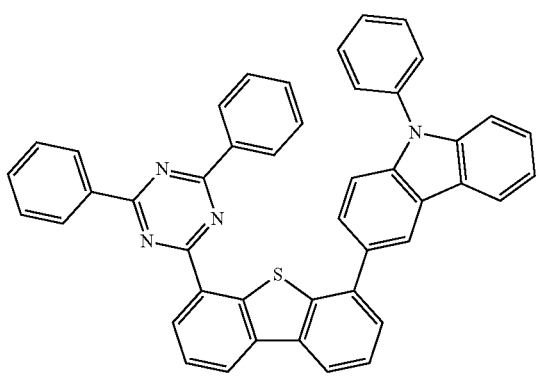
H-185
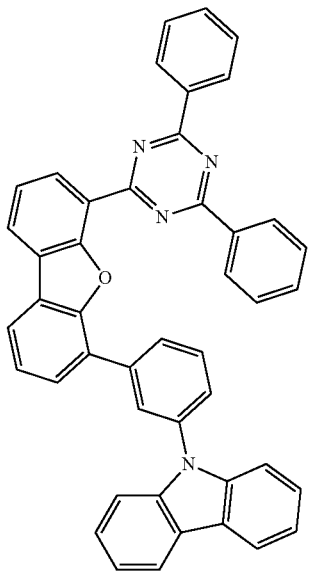
H-186
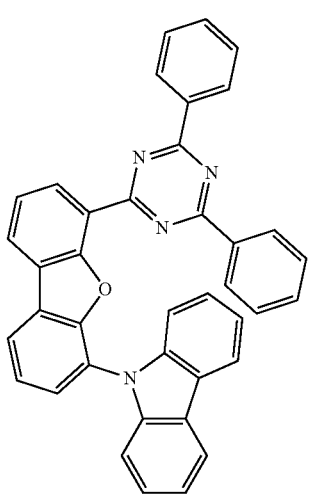

H-187
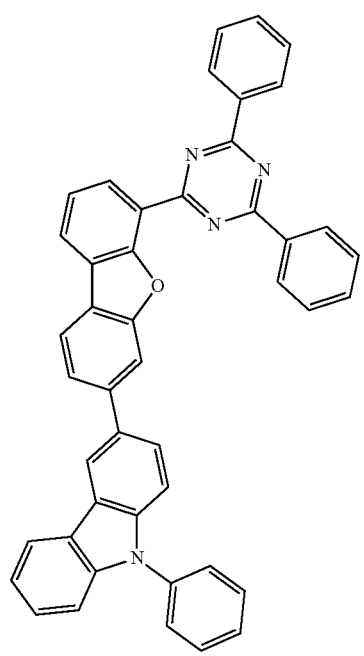
H-189
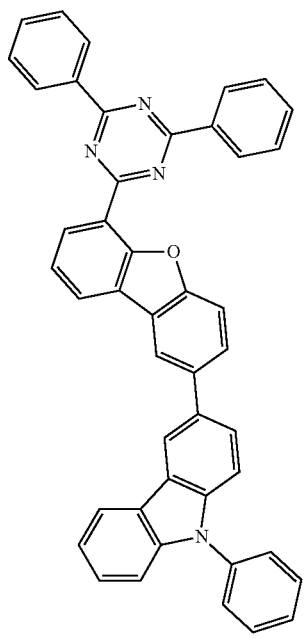
H-188
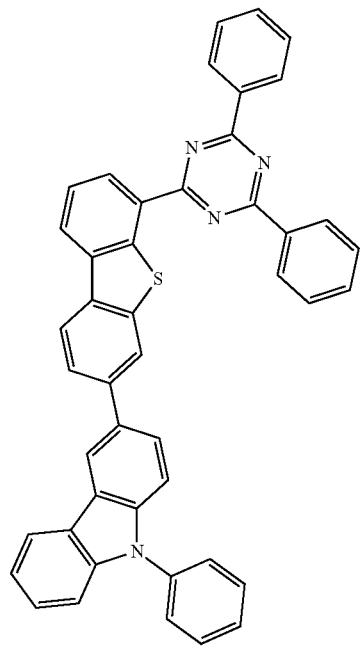
H-190
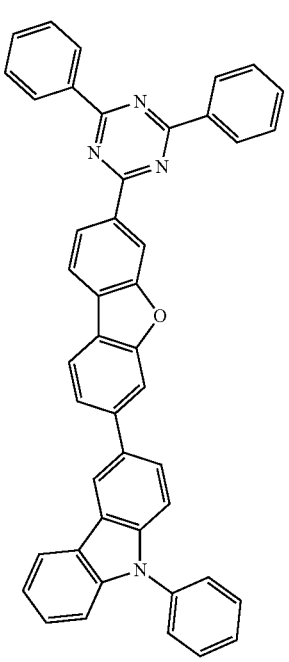

H-191
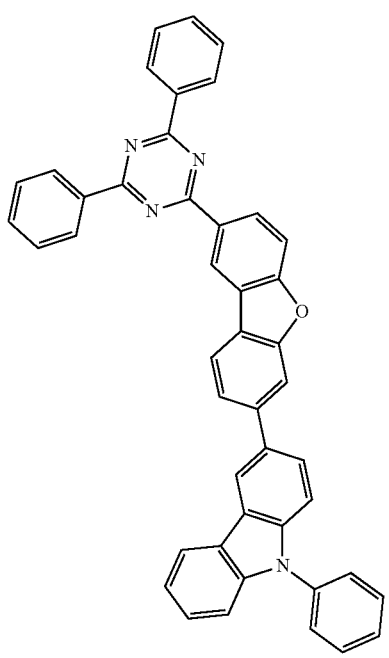
H-192
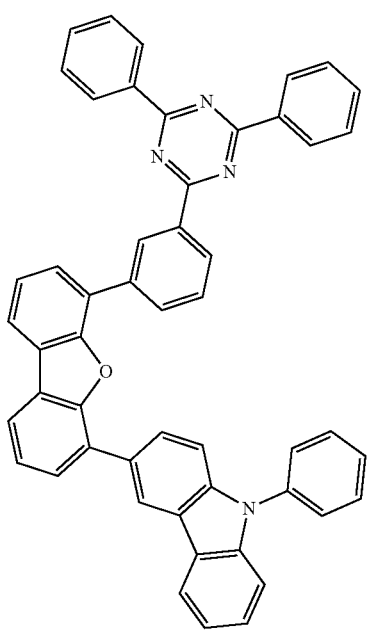
H-193
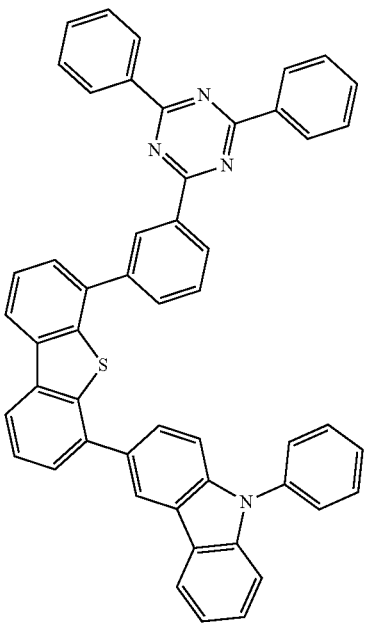
H-194
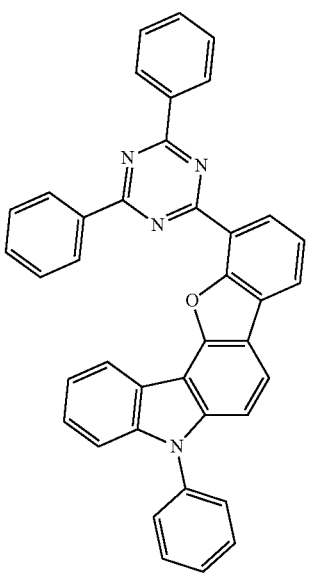

H-195
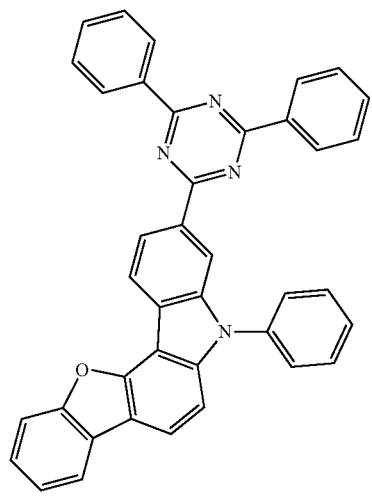
H-197
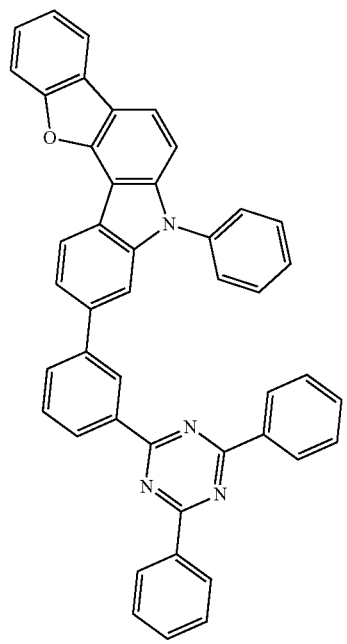
H-196
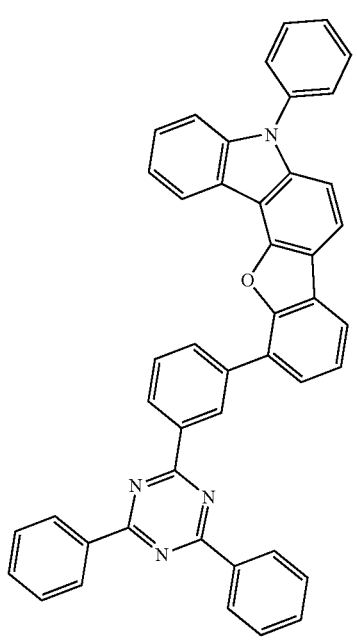
H-198
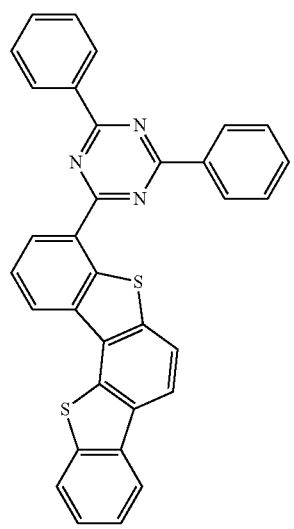

H-199
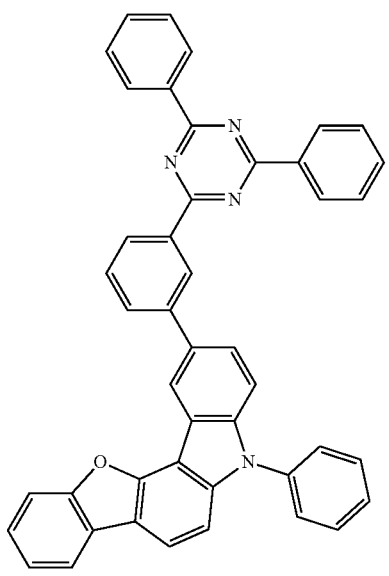
H-200
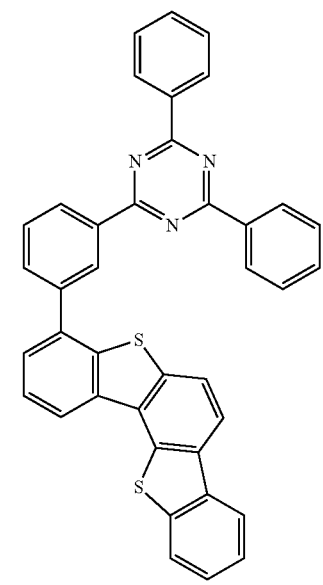
H-201
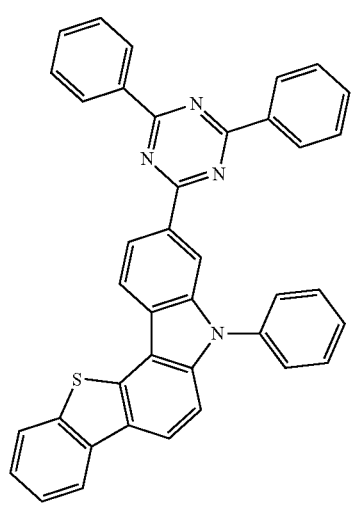
H-202
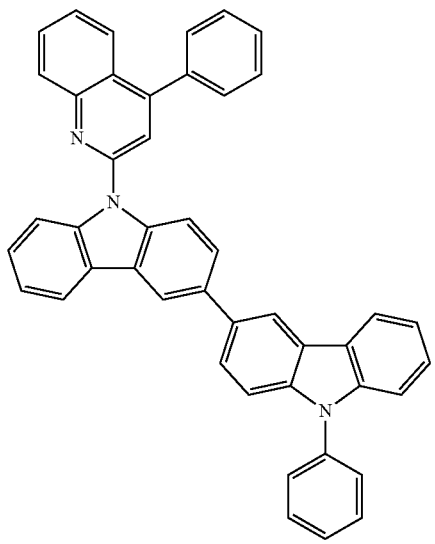
H-203
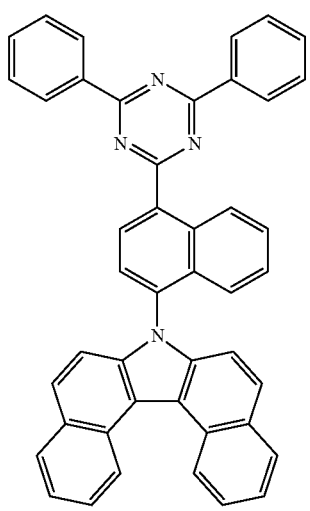
H-204
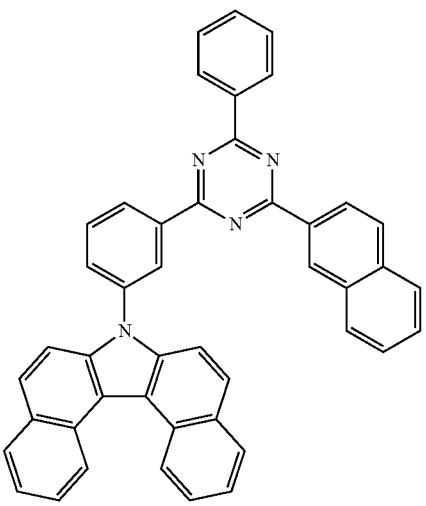

-continued
H-205
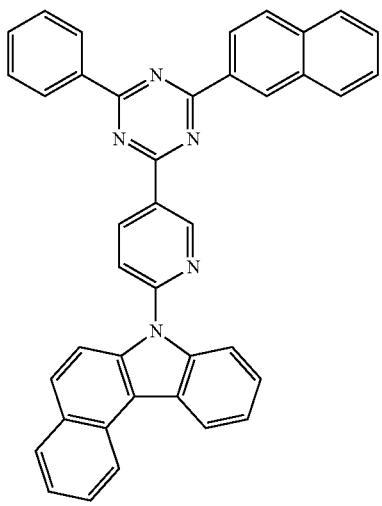
H-208
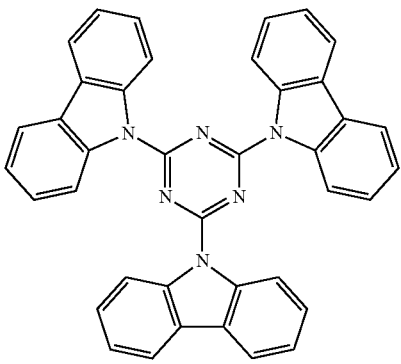
H-206
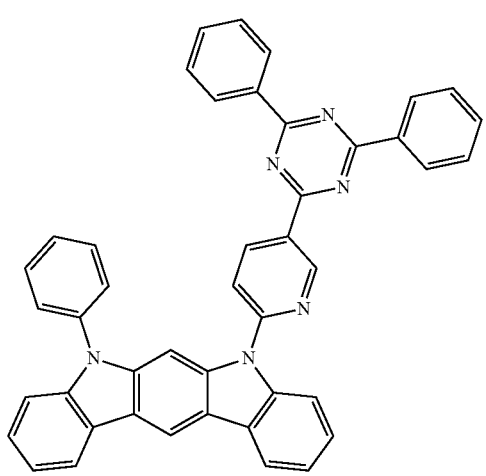
H-209
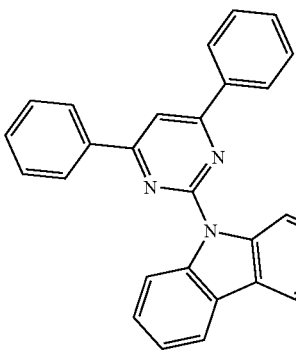
H-207
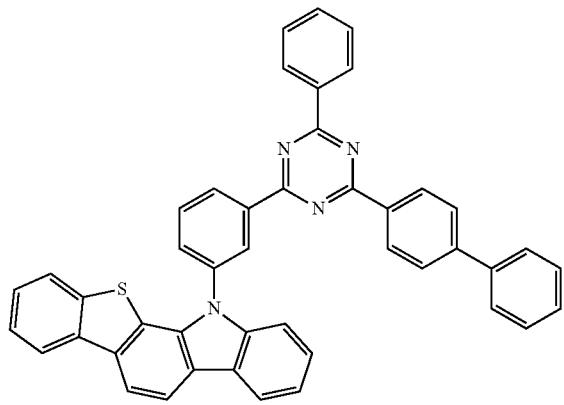
H-210
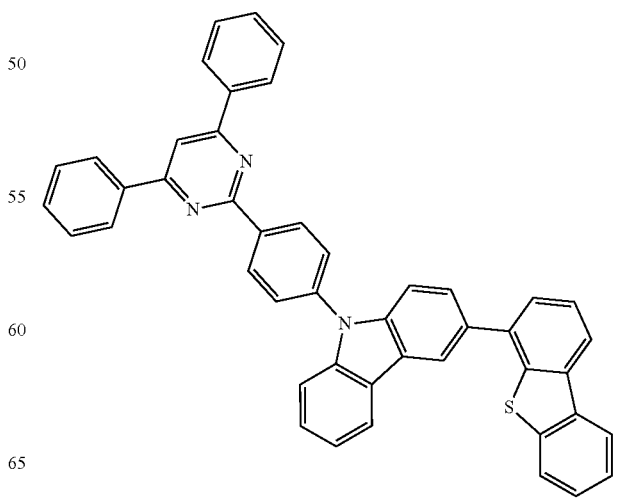

H-211

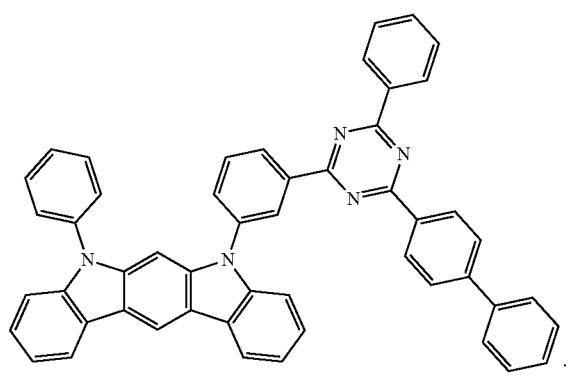

[Wherein, TPS represents a triphenylsilyl group.]

The dopant comprised in the organic electroluminescent device of the present disclosure may be at least one phosphorescent or fluorescence dopant, preferably, phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may use at least one of the compounds represented by the following formula 101, but is not limited thereto:

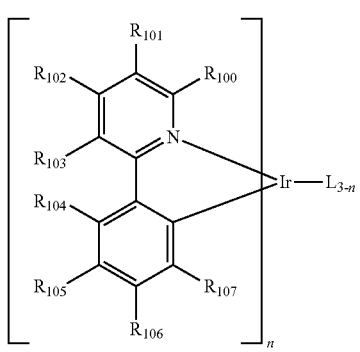

(101)

wherein, L is selected from the following structure 1 or 2:

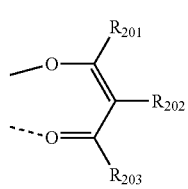

structure (1)

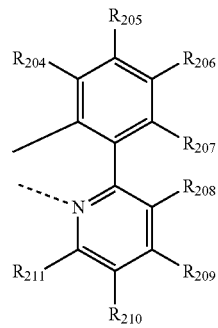

structure (2)

$R_{100}$ to $R_{103}$ each independently represent hydrogen, deuterium, halogen, a halogen-substituted or unsubstituted (C1-C30)alkyl, a substituted or unsubstituted (C3-C30)cycloalkyl, a substituted or unsubstituted (C6-C30)aryl, cyano, a substituted or unsubstituted (3- to 30-membered)heteroaryl, or a substituted or unsubstituted (C1-C30)alkoxy; or $R_{100}$ to $R_{103}$ may be linked to adjacent substituents to form a substituted or unsubstituted fused ring, e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline;

$R_{104}$ to $R_{107}$ each independently represent hydrogen, deuterium, halogen, a halogen-substituted or unsubstituted (C1-C30)alkyl, a substituted or unsubstituted (C3-C30)cycloalkyl, a substituted or unsubstituted (C6-C30)aryl, a substituted or unsubstituted (3- to 30-membered)heteroaryl, cyano, or a substituted or unsubstituted (C1-C30)alkoxy; or $R_{104}$ to $R_{107}$ may be linked to adjacent substituents to form a substituted or unsubstituted fused ring, e.g., a substituted or unsubstituted naphthyl, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine;

$R_{201}$ to $R_{211}$ each independently represent hydrogen, deuterium, halogen, a halogen-substituted or unsubstituted (C1-C30)alkyl, a substituted or unsubstituted (C3-C30)cycloalkyl, or a substituted or unsubstituted (C6-C30)aryl; or $R_{201}$ to $R_{211}$ may be linked to adjacent substituents to form a substituted or unsubstituted fused ring;

n represents an integer of 1 to 3.

The specific examples of the dopant material include the following, but is not limited thereto:

D-1

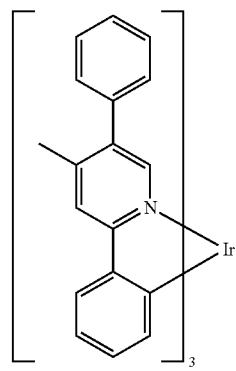

D-2
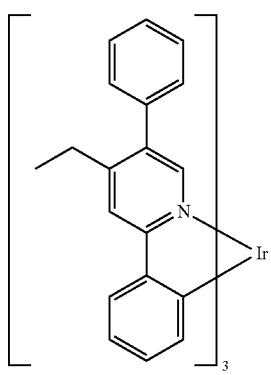
D-6
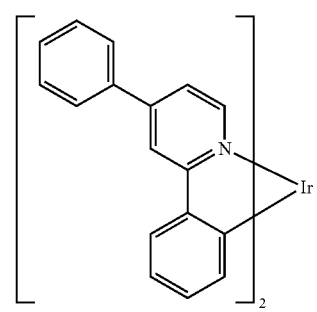
D-3
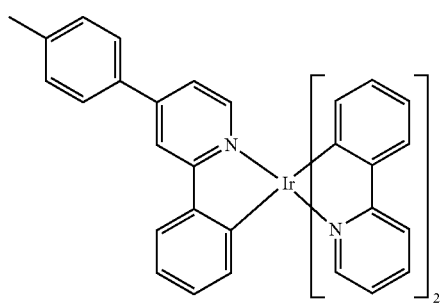
D-7
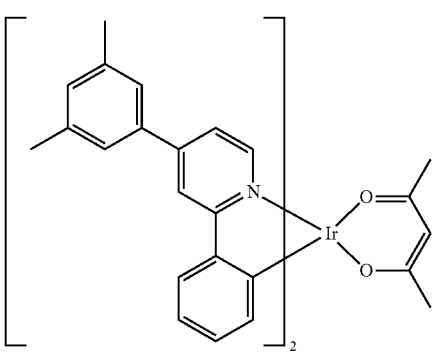
D-4
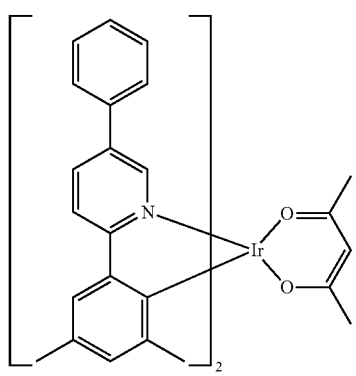
D-8
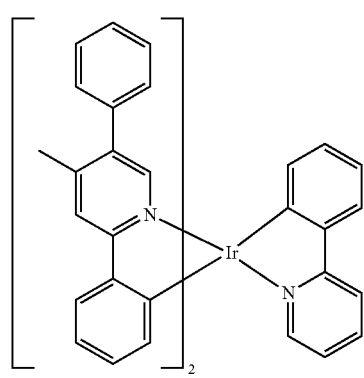
D-5
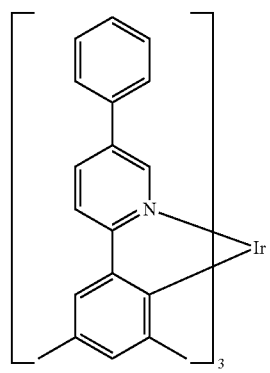
D-9

-continued
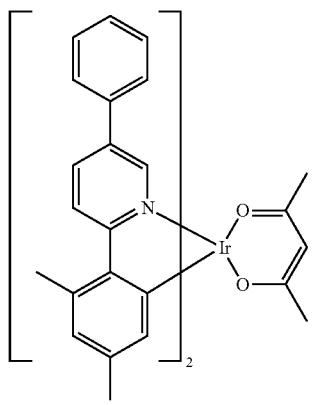
D-10
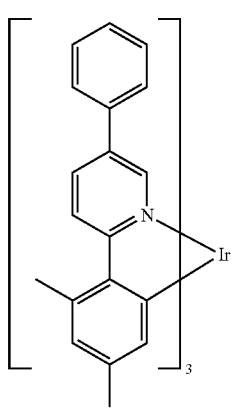
D-11
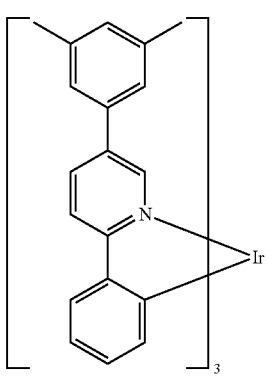
D-12
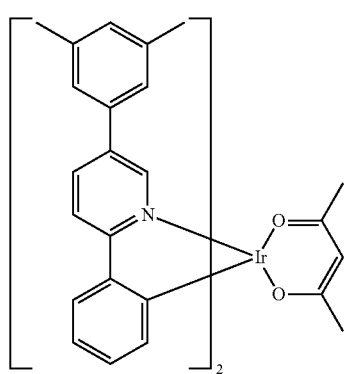
D-13
-continued
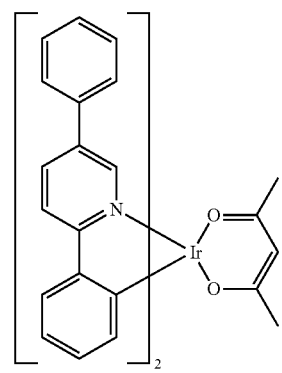
D-14
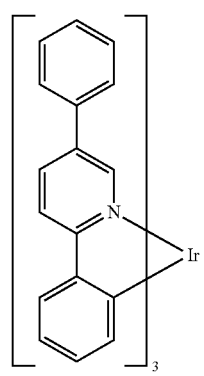
D-15
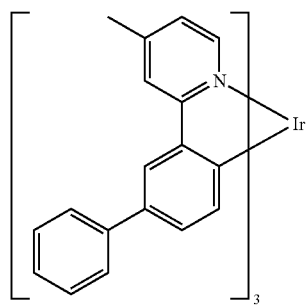
D-16
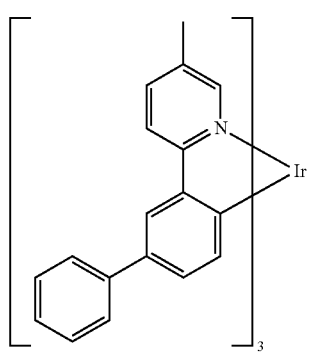
D-17

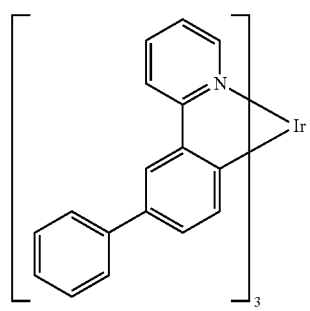
D-18
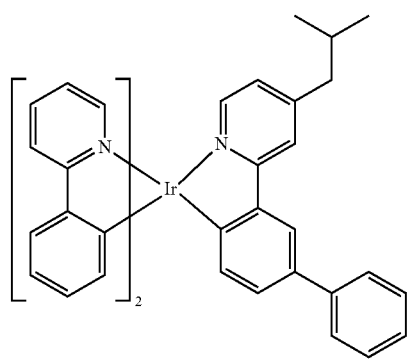
D-22
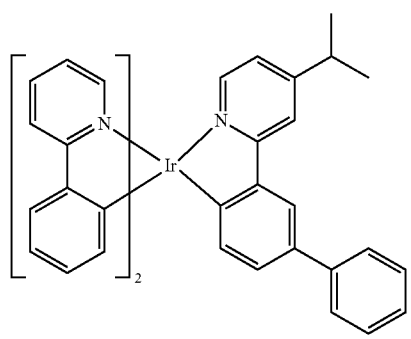
D-19
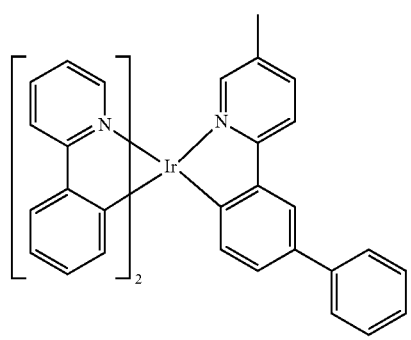
D-23
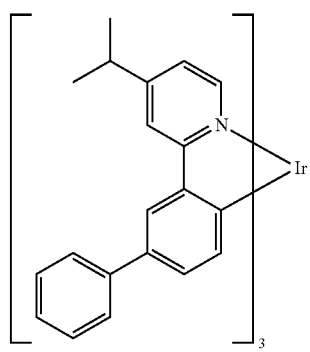
D-20
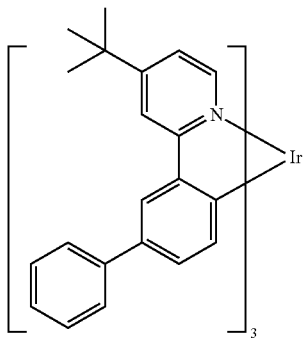
D-24
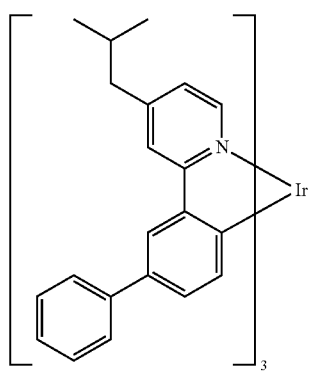
D-21
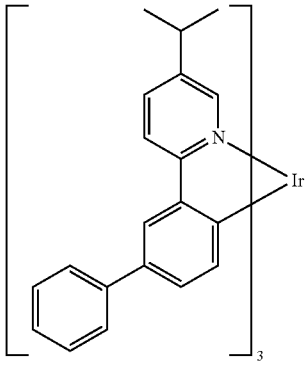
D-25

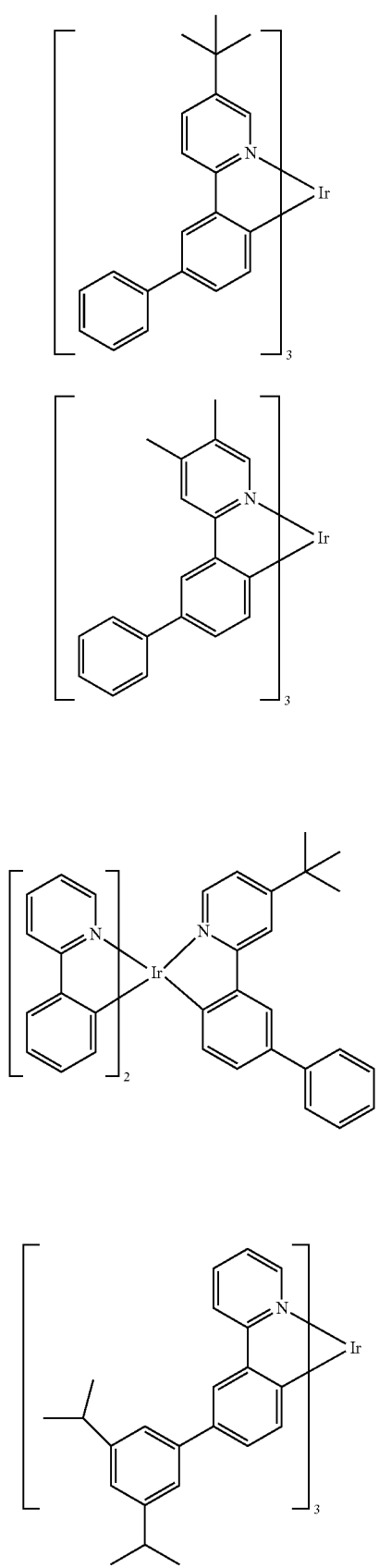
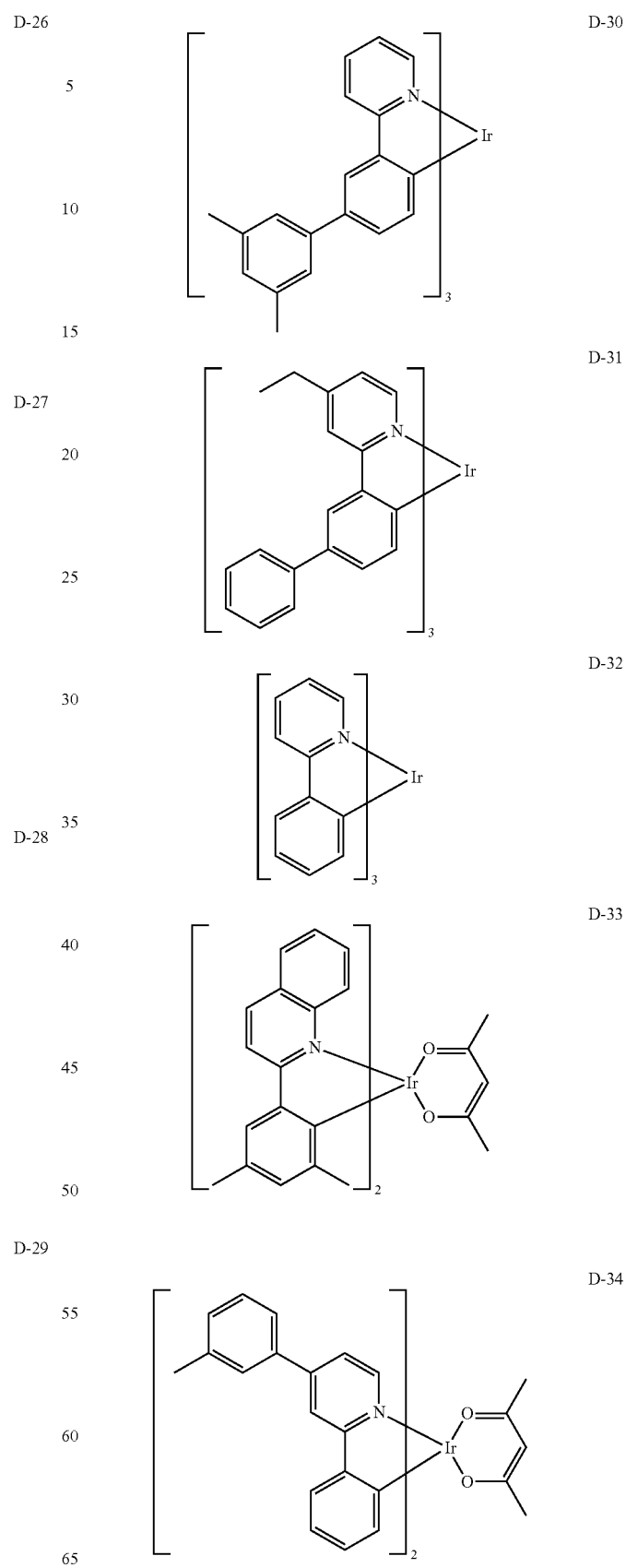

D-35
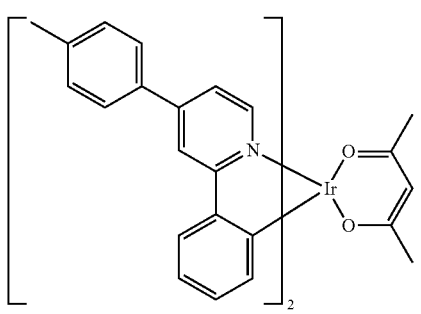
D-39
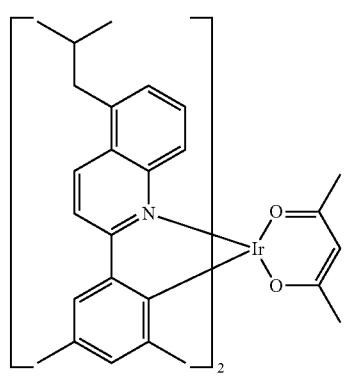
D-36
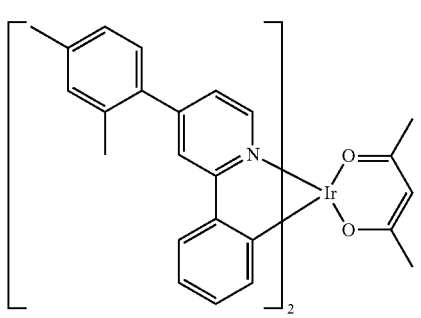
D-40
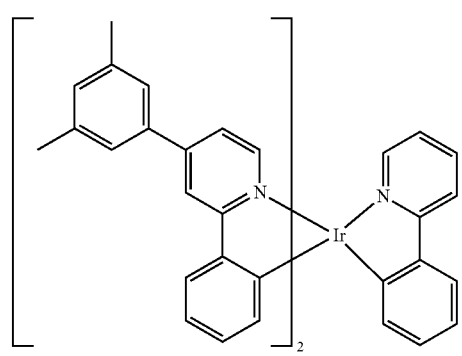
D-37
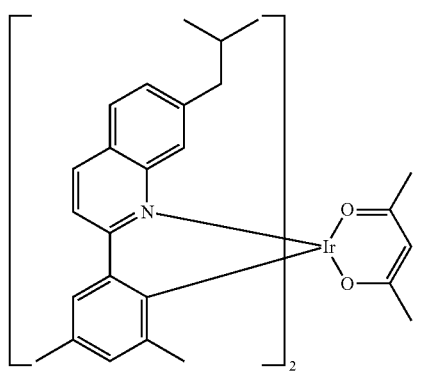
D-41
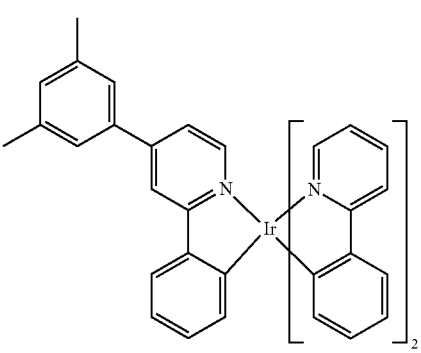
D-38
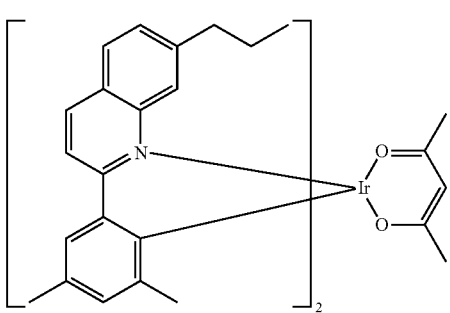
D-42
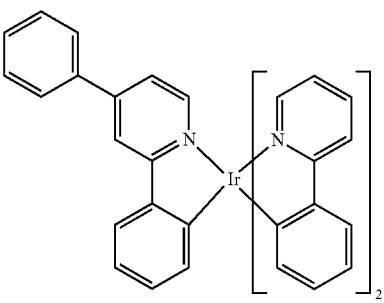

-continued
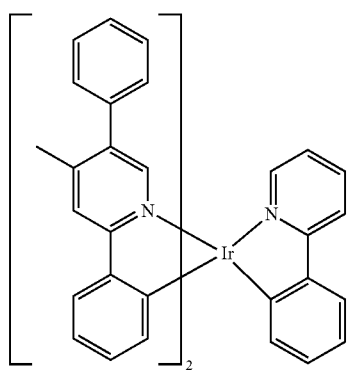
D-43
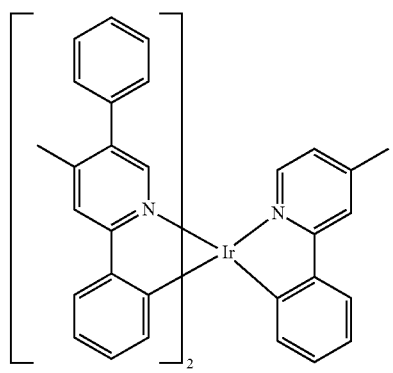
D-44
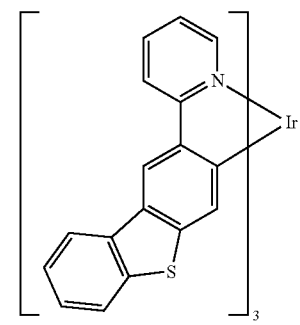
D-45
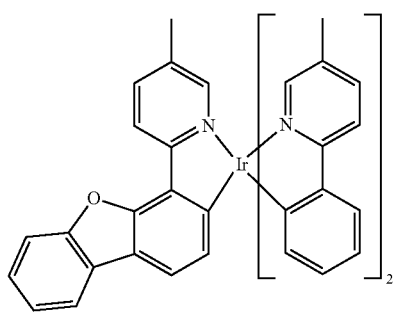
D-46
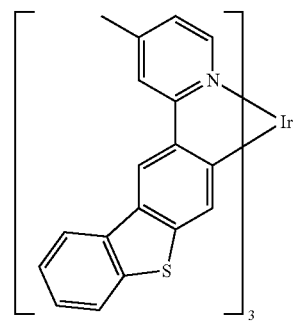
D-47
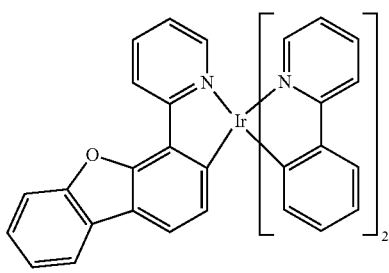
D-48
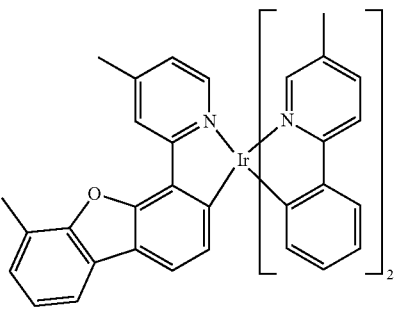
D-49
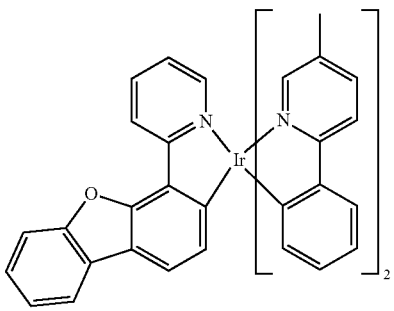
D-50
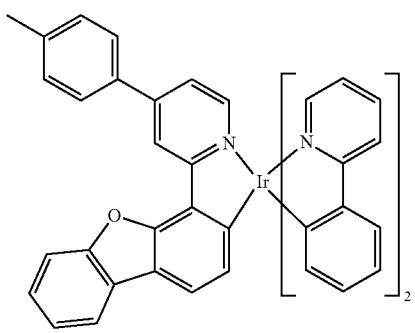
D-51

D-52
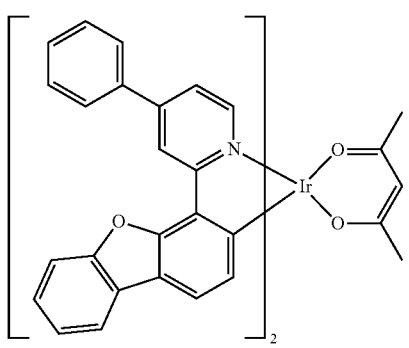
D-53
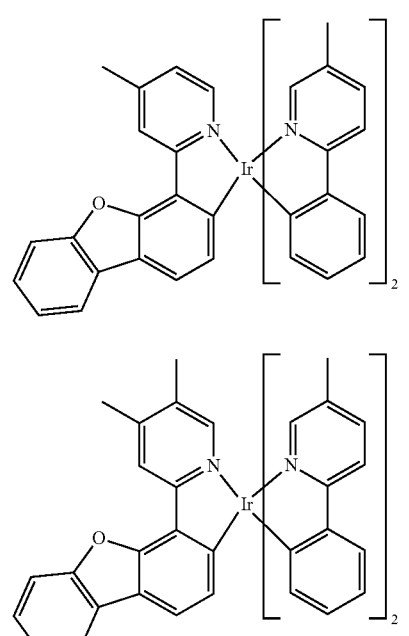
D-54
D-55
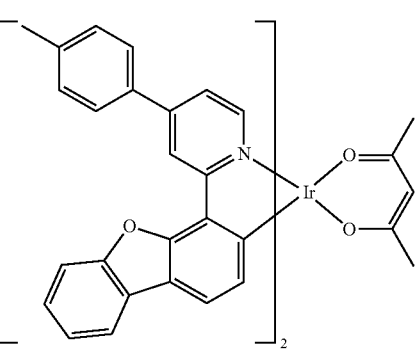
D-56
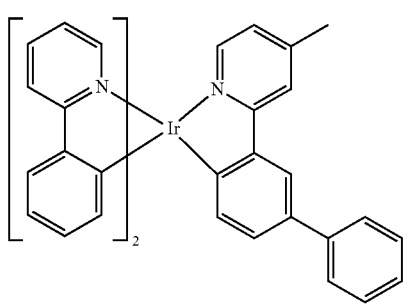
D-57
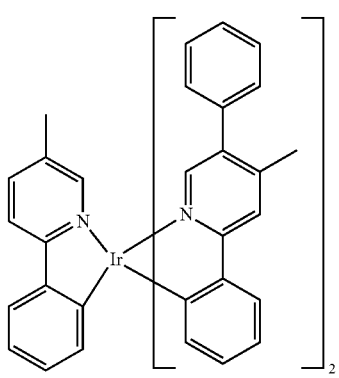
D-58
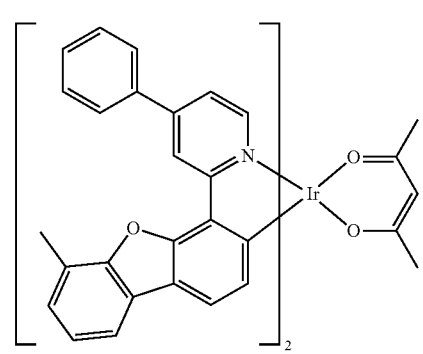
D-59
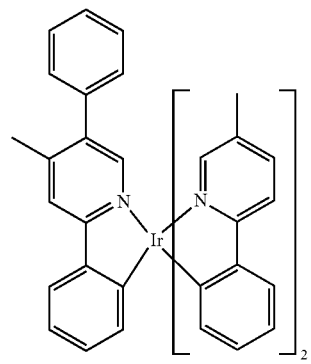
D-60
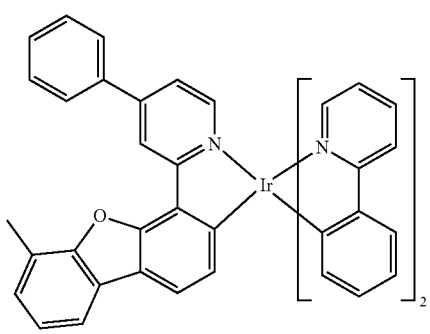

D-61
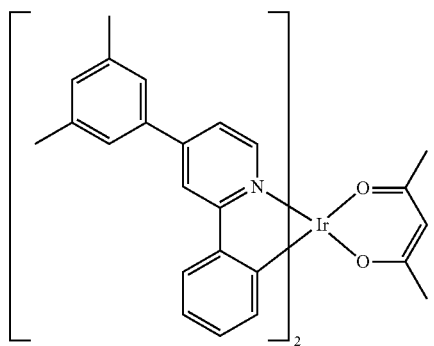
D-62
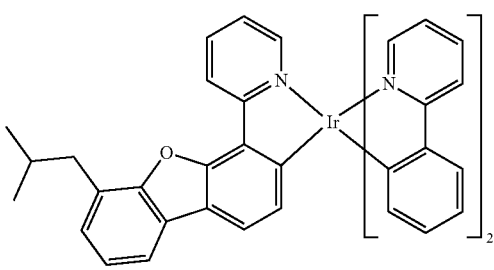
D-63
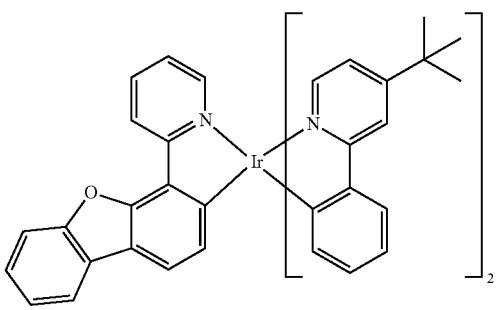
D-64
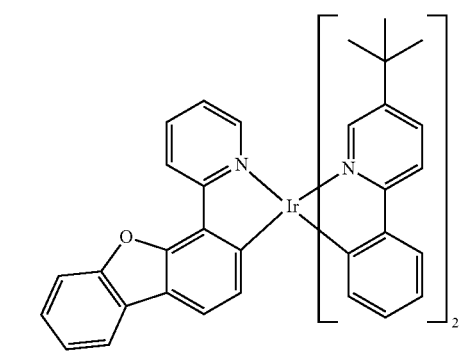
D-65
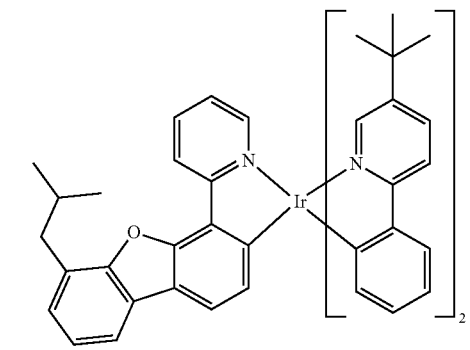
D-66
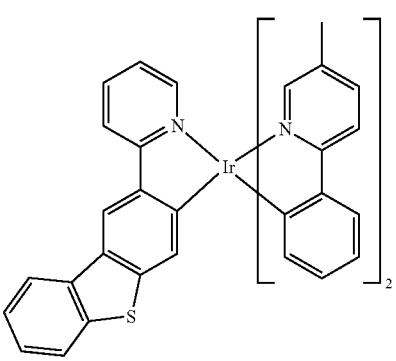
D-67
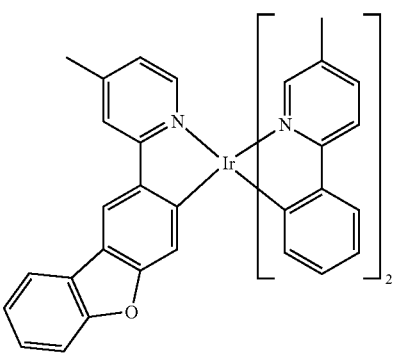
D-68
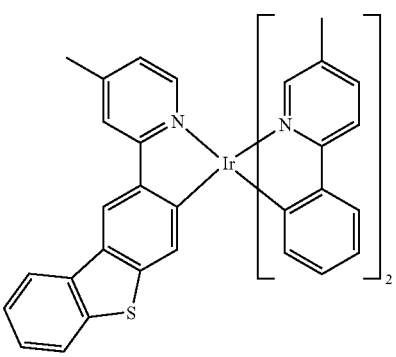
D-69
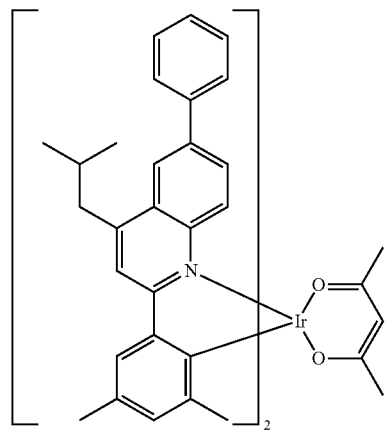

D-70
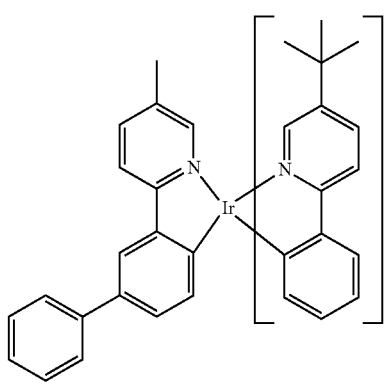
D-71
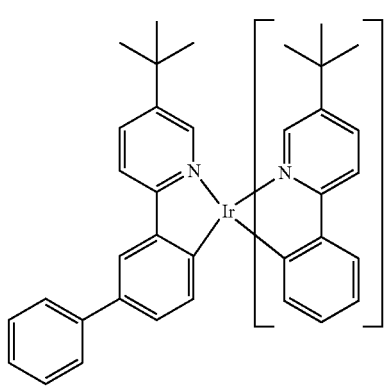
D-72
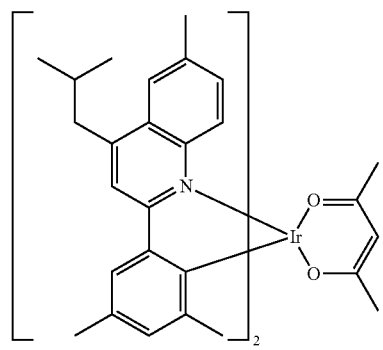
D-73
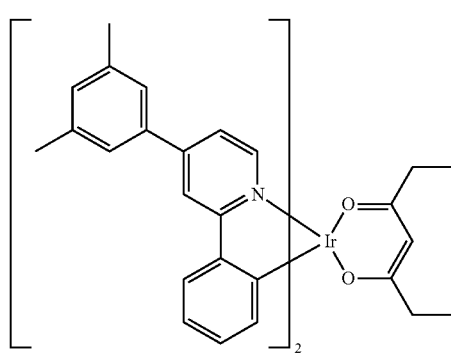
D-74
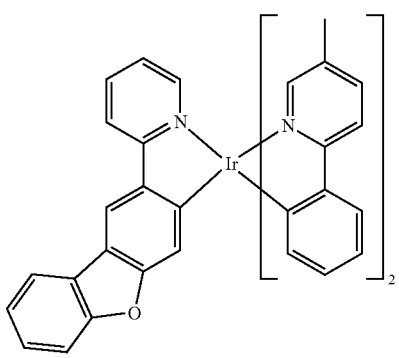
D-75
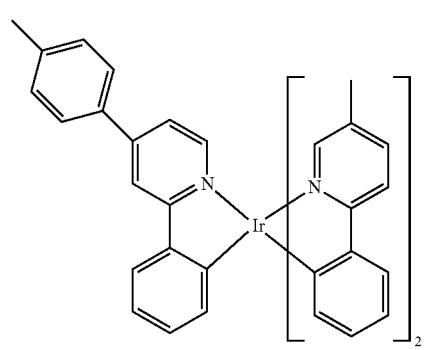
D-76
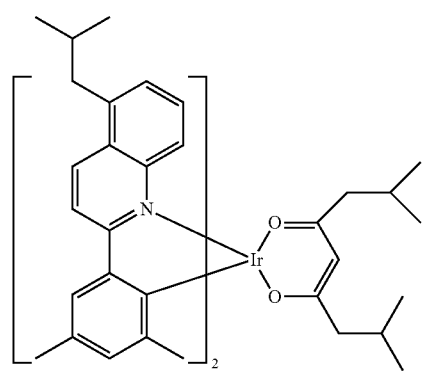
D-77
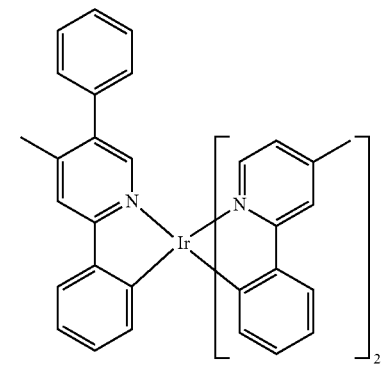

-continued
D-78
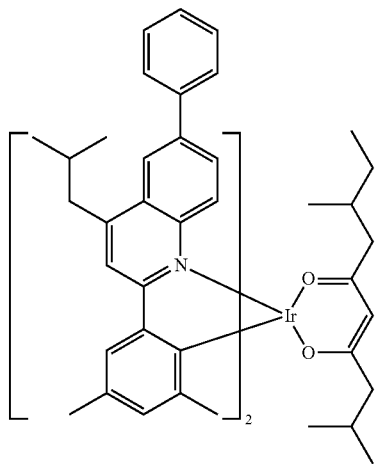
D-79
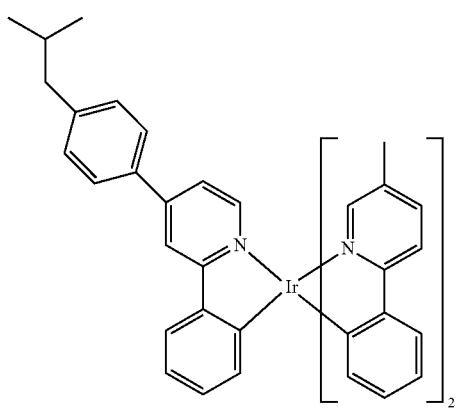
D-80
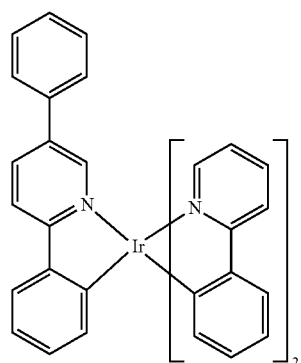
-continued
D-81
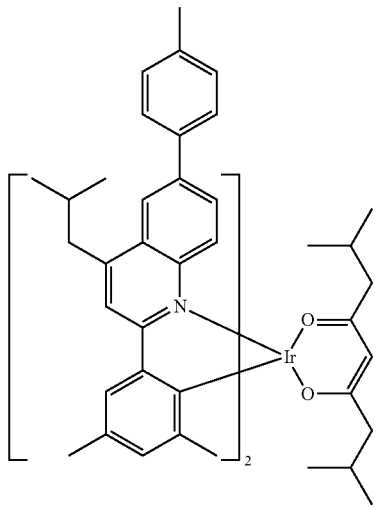
D-82
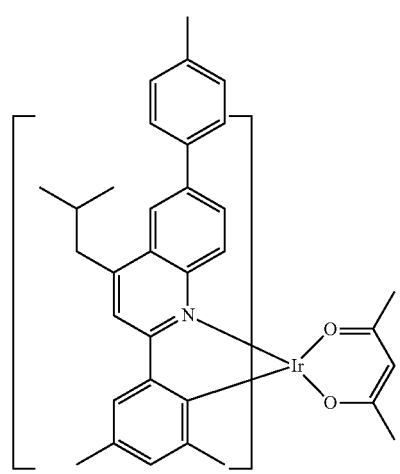
D-83
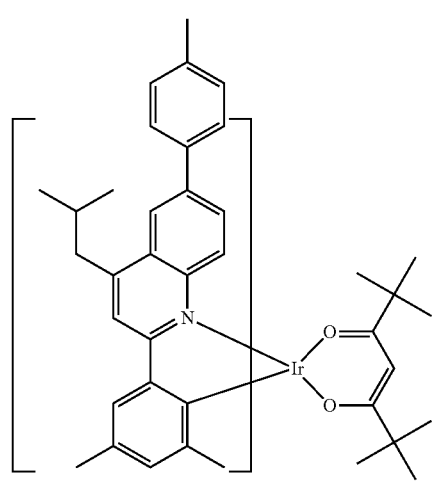

D-84
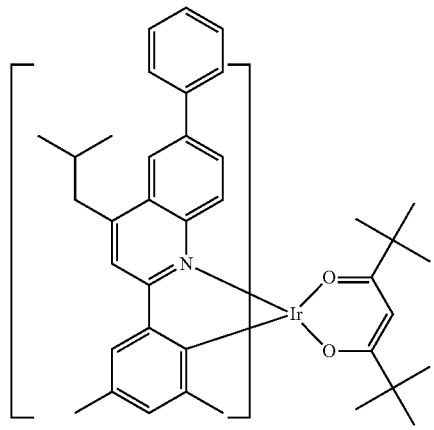
D-85
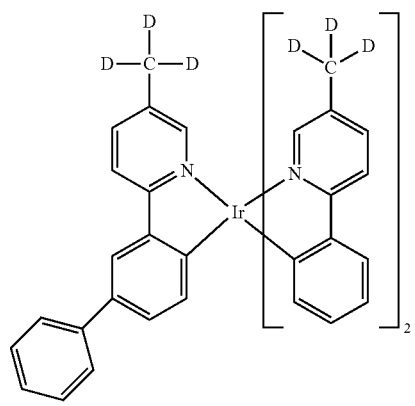
D-86
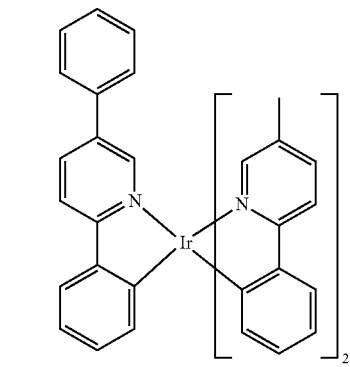
D-87
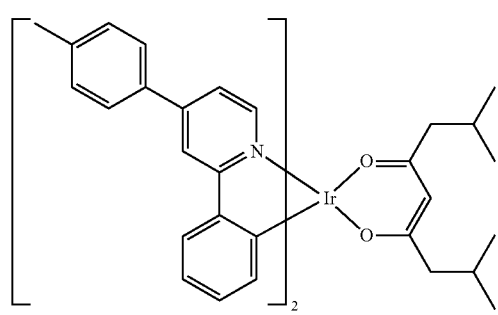
D-88
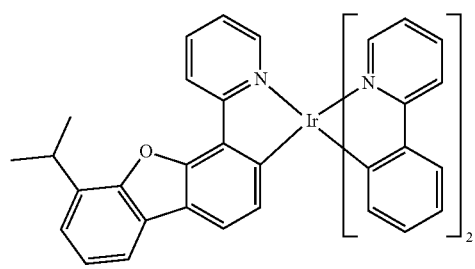
D-89
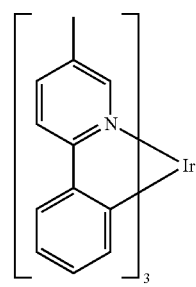
D-90
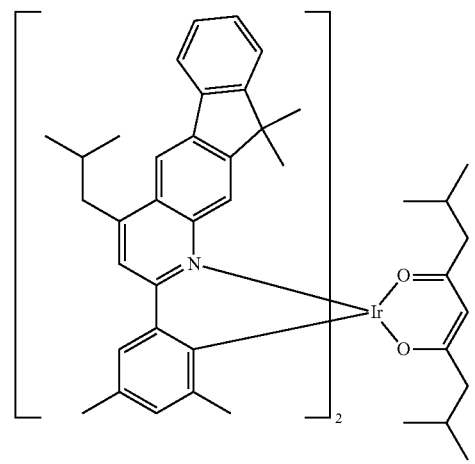
D-91
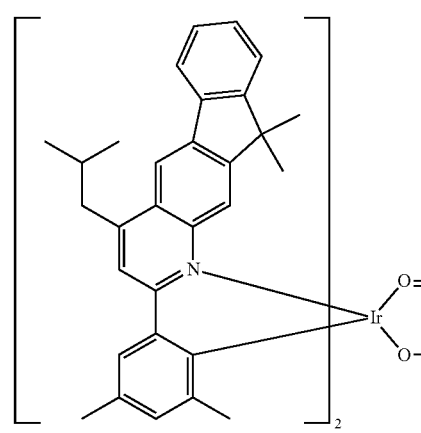

D-92
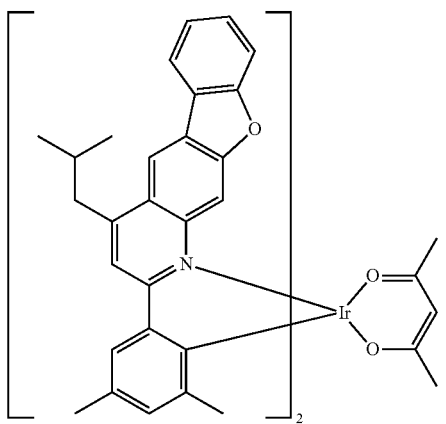
D-95
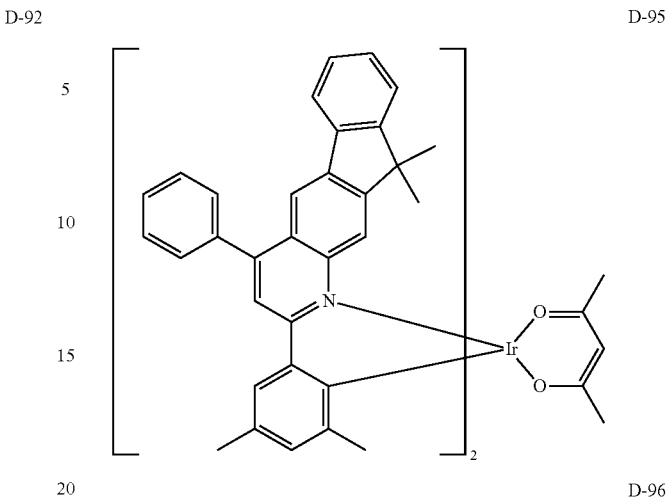
D-93
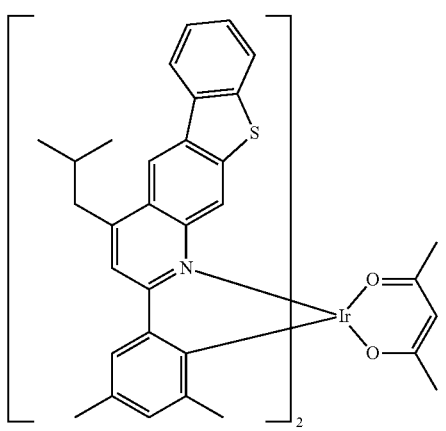
D-96
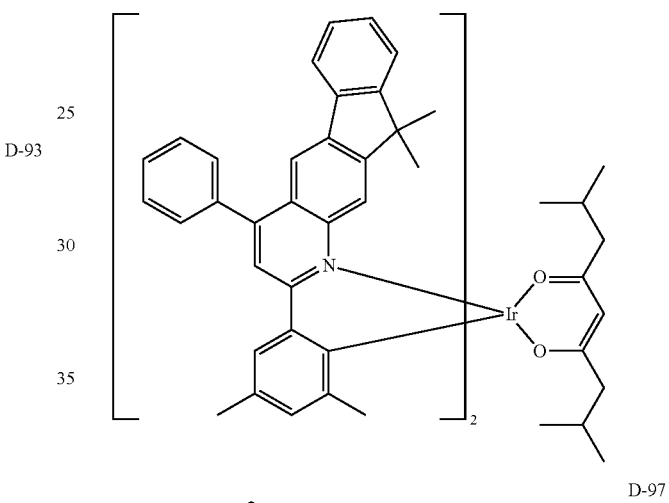
D-94
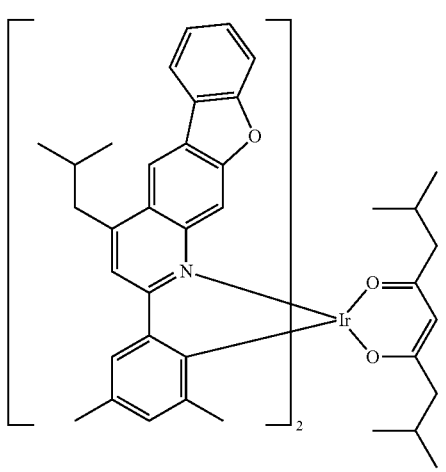
D-97
D-98
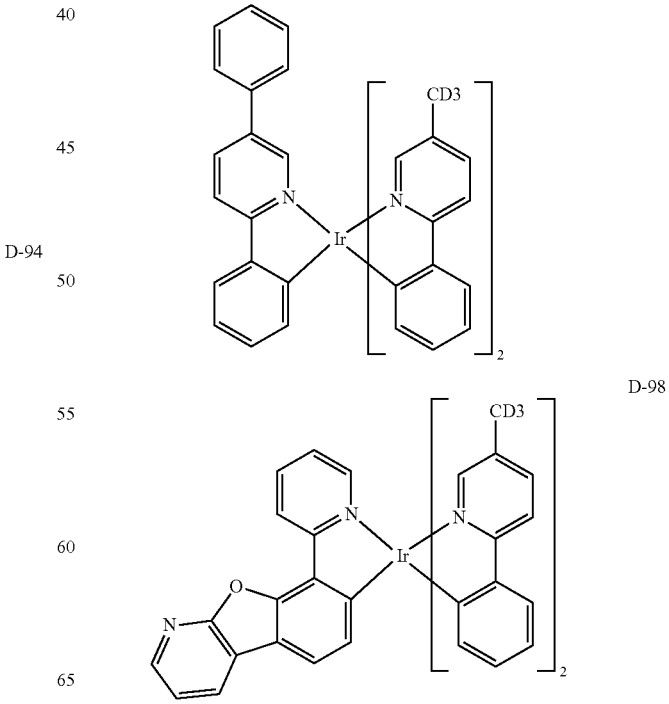

D-99
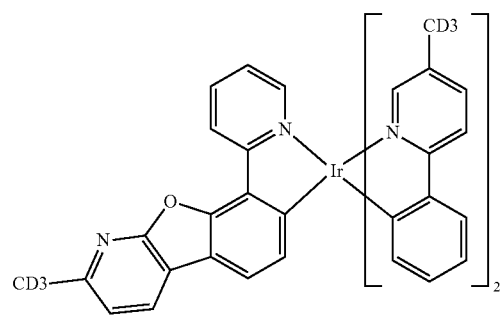
D-100
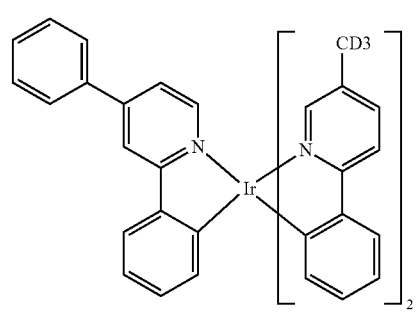
D-101
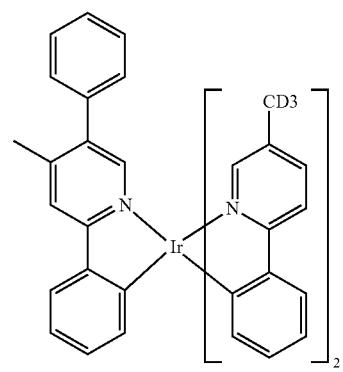
D-102
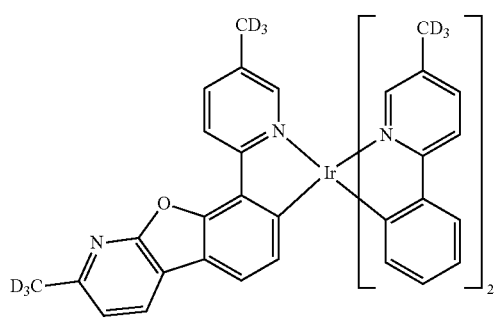
D-103
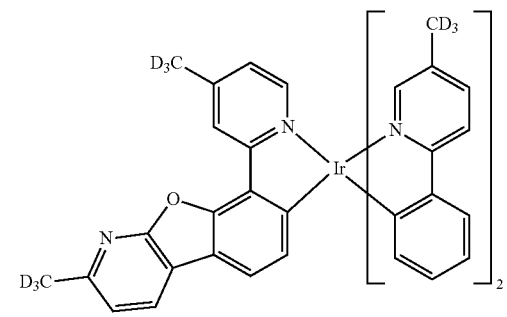
D-104
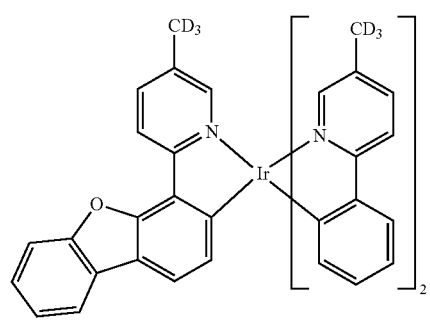
D-105
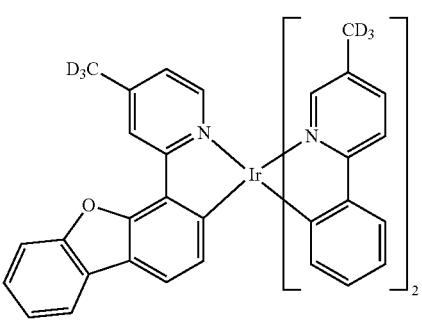
D-106
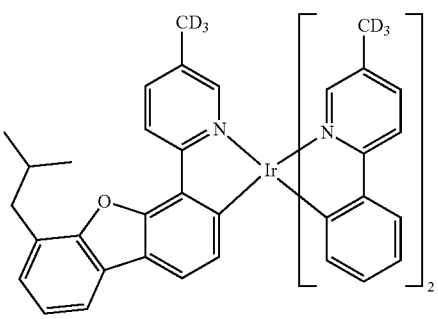
D-107
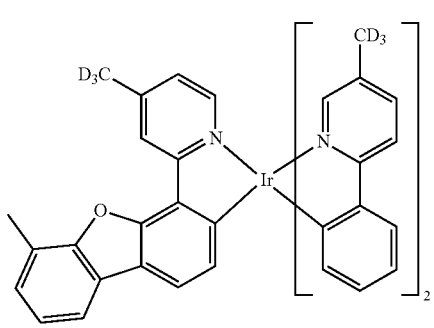

-continued
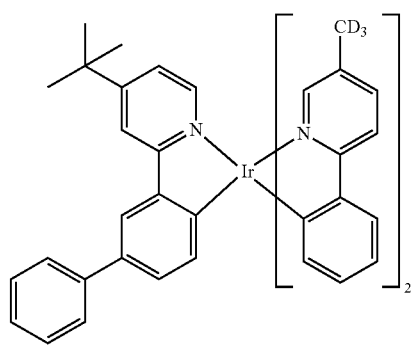
D-108
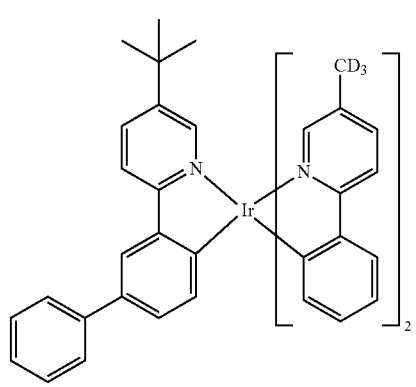
D-109
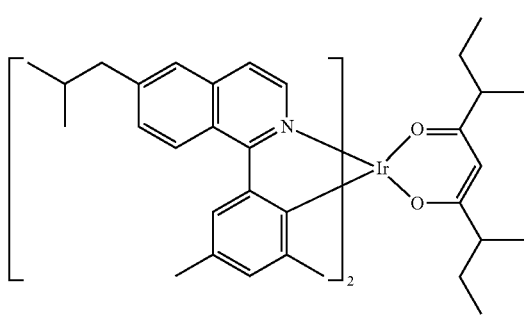
D-110
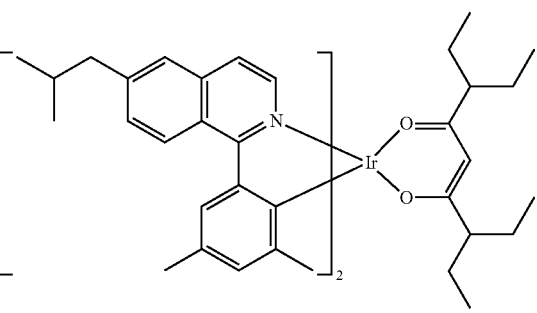
D-111
-continued
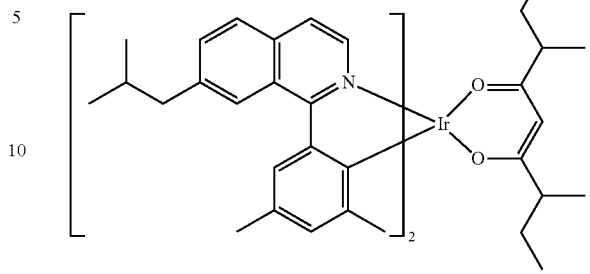
D-112
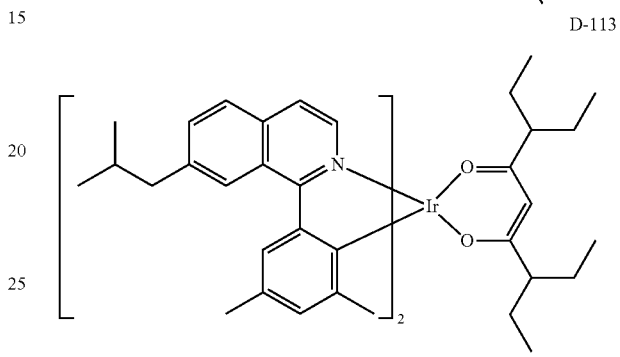
D-113
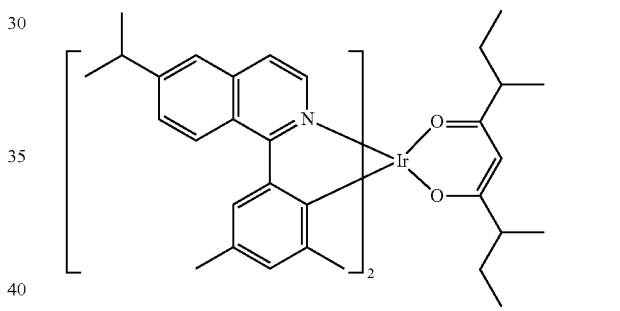
D-114
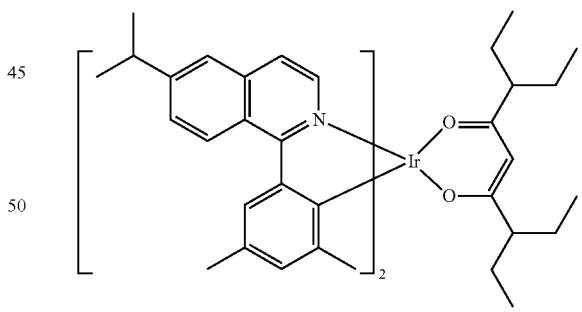
D-115
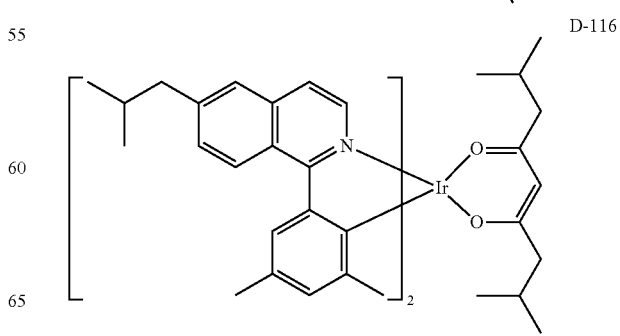
D-116

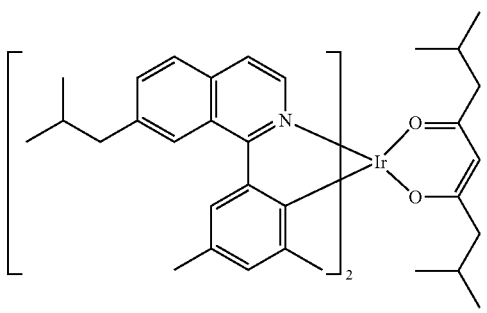

D-117

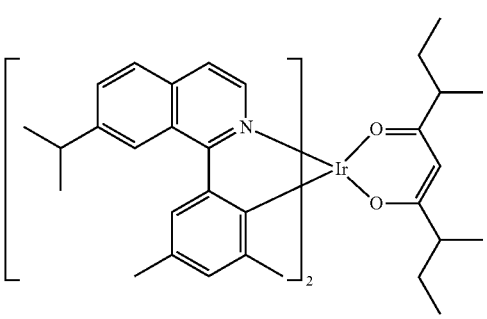

D-118

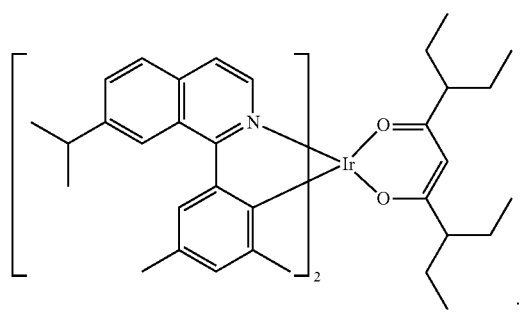

D-119

The formation of each layer of the organic electroluminescence device of the present disclosure can use one of dry film-forming methods such as vacuum evaporation, sputtering, plasma, ion plating methods, etc., and wet film-forming methods such as ink jet printing, nozzle printing, slot coating, spin coating, dip coating, flow coating methods, etc., but is not limited thereto. When forming a layer by the dopant and the host compounds of the present disclosure, co-evaporation or mixture-evaporation may be used, but is not limited thereto.

When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

The co-deposition is a mixed deposition method in which two or more isomer materials are put into respective individual crucible sources and a current is applied to both cells simultaneously to evaporate the materials and to perform mixed deposition; and the mixed deposition is a mixed deposition method in which two or more isomer materials are mixed in one crucible source before deposition, and then a current is applied to one cell to evaporate the materials.

Also, the organic electroluminescent device of the present disclosure can be used for the manufacture of display devices such as smartphones, tablets, notebooks, PCs, TVs, or display devices for vehicles, or lighting devices such as outdoor or indoor lighting.

Hereinafter, the preparation method of an organic electroluminescent compound according to the present disclosure, and the properties thereof will be explained in detail with reference to the representative compounds of the present disclosure in order to understand the present disclosure in detail. However, the present disclosure is not limited by the following examples.

[Example 1] Preparation of Compound C-1

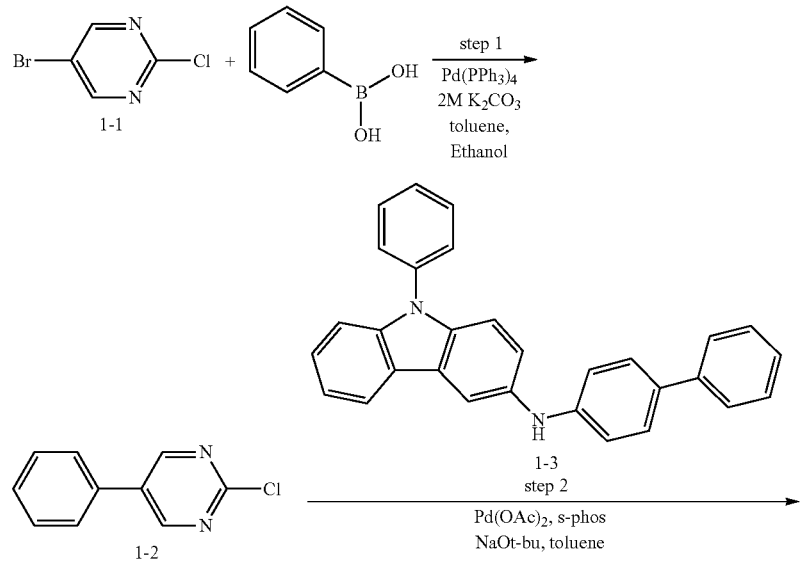

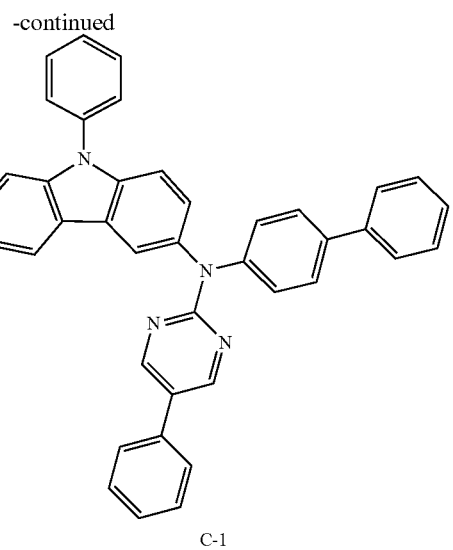

C-1

Preparation of Compound 1-2

Compound 1-1 (5-bromo-2-chloropyrimidine) (4 g, 20.7 mmol), phenylboronic acid (2.78 g, 22.8 mmol), tetrakis(triphenylphosphine)palladium(O) (Pd(PPh$_3$)$_4$) (0.9 g, 0.8 mmol), 2M potassium carbonate (K$_2$CO$_3$) (21 mL), 80 mL of toluene, and 6 mL of ethanol were added into a flask and dissolved, and the mixture was refluxed for 3 hours at 120° C. After completion of the reaction, the organic layer was extracted with ethyl acetate. The residual moisture was removed with magnesium sulfate and dried, and the resulting product was purified by column chromatography to obtain compound 1-2 (2.8 g, yield: 71%).

Preparation of Compound C-1

Compound 1-2 (3.3 g, 17.5 mmol), compound 1-3 (6 g, 14.6 mmol), palladium(II)acetate (Pd(OAc)$_2$) (0.15 g, 0.7 mmol), 2-dicyclohexylphosphino-2',6'-dimethoxybiphenyl (s-phos) (0.61 g, 1.5 mmol), sodium-tert-butoxide (NaOt-bu) (3 g, 29.2 mmol), and 250 mL of toluene were added into a flask, and the mixture was refluxed for 4 hours at 120° C. After completion of the reaction, distilled water was added thereto, and the organic layer was extracted with dichloromethane. The residual moisture was removed with magnesium sulfate and dried, and the resulting product was purified by column chromatography to obtain compound C-1 (4.3 g, yield: 52%).

|     | MW     | UV     | PL     | M.P     |
| --- | ------ | ------ | ------ | ------- |
| C-1 | 564.68 | 334 nm | 489 nm | 203° C. |

[Example 2] Preparation of Compound C-81

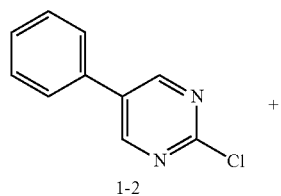

1-2

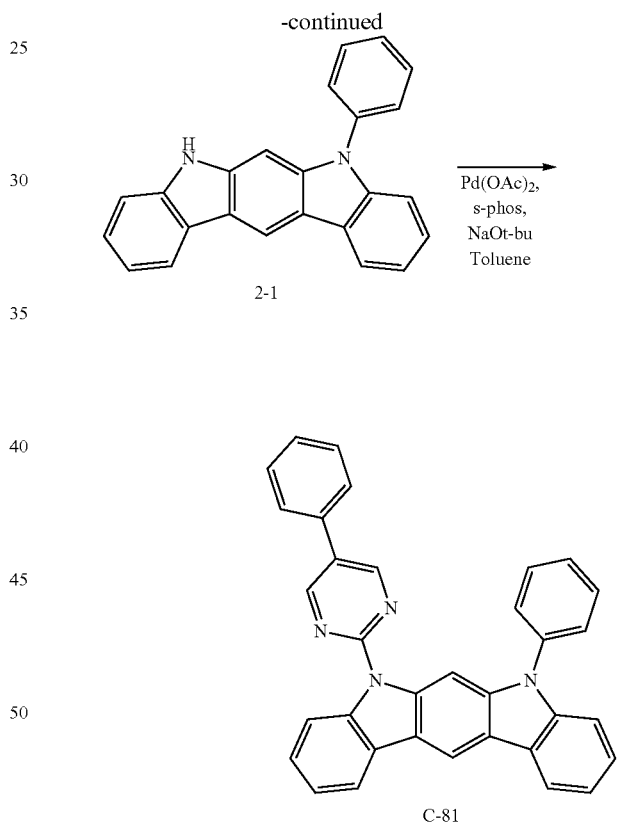

Preparation of Compound C-81

Compound 1-2 (2.7 g, 14.2 mmol), compound 2-1 (3.5 g, 10.9 mmol), Pd(OAc)$_2$ (0.11 g, 0.5 mmol), s-phos (0.45 g, 1.1 mmol), NaOt-bu (2.8 g, 27.3 mmol), and 200 mL of toluene were added into a flask, and the mixture was refluxed for 4 hours at 140° C. After completion of the reaction, distilled water was added thereto, and the organic layer was extracted with dichloromethane. The residual moisture was removed with magnesium sulfate and dried, and the resulting product was purified by column chromatography to obtain compound C-81 (3.2 g, yield: 60.3%).

| | M.P |
|---|---|
| C-81 | 231° C. |

Hereinafter, the preparation method of an organic electroluminescent device comprising the host compound of the present disclosure, and the luminescent characteristics thereof, will be described in order to understand the present disclosure in detail.

[Device Example 1] Producing an Organic Electroluminescent Device by Deposition of the Compound According to the Present Disclosure as a Host An OLED device according to the present disclosure was produced. A transparent electrode indium tin oxide (ITO) thin film (10 Ω/sq) on a glass substrate for an OLED (GEOMATEC CO., LTD., Japan) was subjected to an ultrasonic washing with acetone and isopropanol, sequentially, and then was stored in isopropanol. Next, the ITO substrate was mounted on a substrate holder of a vacuum vapor deposition apparatus. Compound HIL-1 was introduced into a cell of the vacuum vapor deposition apparatus, and the pressure in the chamber of the apparatus was then controlled to be $10^{-6}$ torr. Thereafter, an electric current was applied to the cell to evaporate the introduced material, thereby forming a first hole injection layer having a thickness of 80 nm on the ITO substrate. Compound HIL-2 was then introduced into another cell of the vacuum vapor deposition apparatus, and an electric current was applied to the cell to evaporate the introduced material, thereby forming a second hole injection layer having a thickness of 5 nm on the first hole injection layer. Next, compound HTL-1 was introduced into another cell of the vacuum vapor deposition apparatus. Thereafter, an electric current was applied to the cell to evaporate the introduced material, thereby forming a first hole transport layer having a thickness of 10 nm on the second hole injection layer. Compound HTL-2 was then introduced into another cell of the vacuum vapor deposition apparatus, and an electric current was applied to the cell to evaporate the introduced material, thereby forming a second hole transport layer having a thickness of 30 nm on the first hole transport layer. After forming the hole injection layers and the hole transport layers, a light-emitting layer was then deposited as follows. Compounds C-1 and H-67 as hosts were introduced into one cell of the vacuum vapor deposition apparatus and compound D-50 as a dopant was introduced into another cell of the apparatus. The two host materials were evaporated at a different rate of 2:1, and the dopant was deposited in a doping amount of 10 wt %, based on the total weight of the host and dopant, to form a light-emitting layer having a thickness of 40 nm on the second hole transport layer. Next, compounds ETL-1 and Liq were introduced into another cell, were evaporated at a rate of 4:6, and were deposited to form an electron transport layer having a thickness of 35 nm on the light-emitting layer. Next, compound Liq as an electron injection layer having a thickness of 2 nm was deposited on the electron transport layer, and an Al cathode having a thickness of 80 nm was deposited by another vacuum vapor deposition apparatus on the electron injection layer, and thereby the OLED device was produced.

[Device Example 2] Producing an Organic Electroluminescent Device by Deposition of the Compound According to the Present Disclosure as a Host An OLED device was produced in the same manner as in Device Example 1, except that compounds C-81 and H-67 were the hosts of the light-emitting layer.

[Comparative Example 1] Producing an Organic Electroluminescent Device Comprising the Conventional Compound as a Host An OLED device was produced in the same manner as in Device Example 1, except that compounds R1 and H-67 were the hosts of the light-emitting layer.

[Comparative Example 2] Producing an Organic Electroluminescent Device Comprising the Conventional Compound as a Host An OLED device was produced in the same manner as in Device Example 1, except that compounds R2 and H-67 were the hosts of the light-emitting layer.

The compounds used in Device Examples 1 and 2 and Comparative Examples 1 and 2, are shown in Table 1 below.

TABLE 1

Hole Injection Layer/
Hole Transport Layer

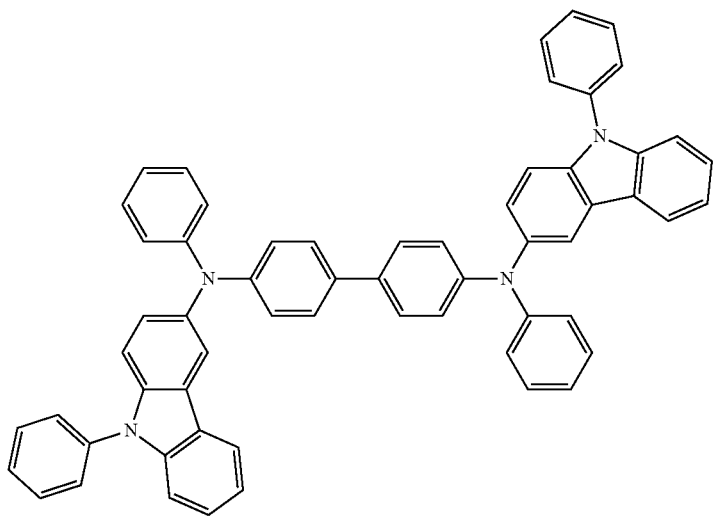

HIL-1

TABLE 1-continued
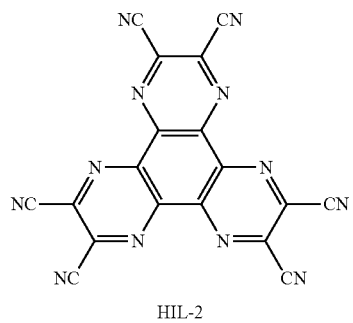 [SMILES: N#Cc1nc2c3nc(C#N)c(C#N)nc3c3nc(C#N)c(C#N)nc3c2nc1C#N]
HIL-2
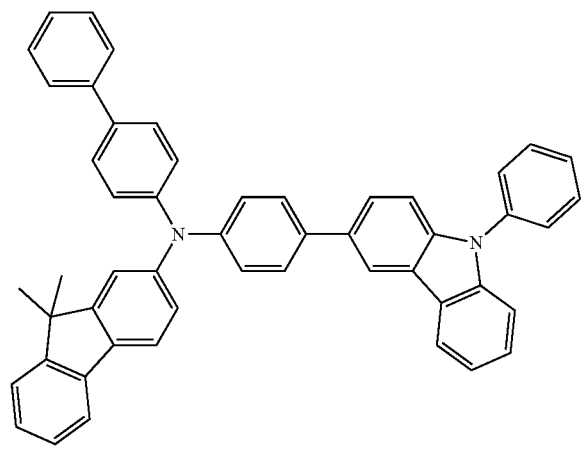
HTL-1
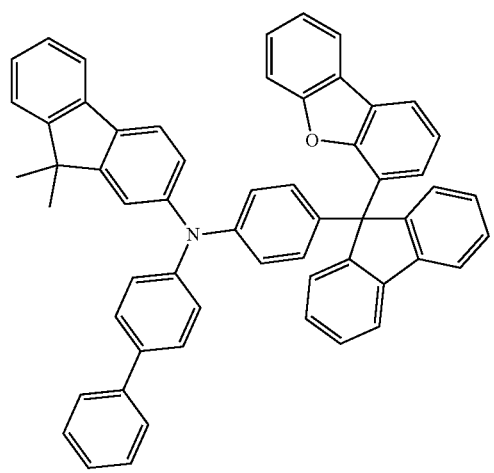
HTL-2

TABLE 1-continued
Light-Emitting Layer
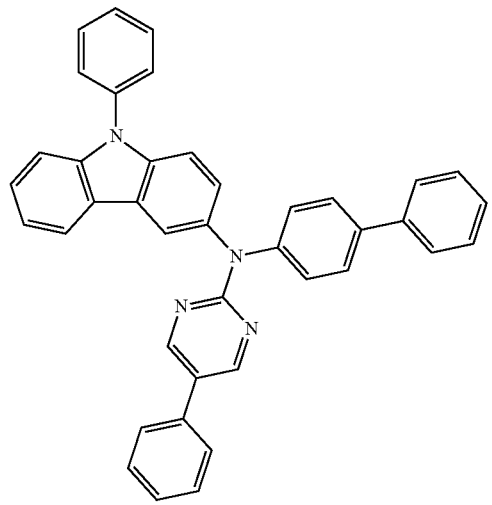
C-1
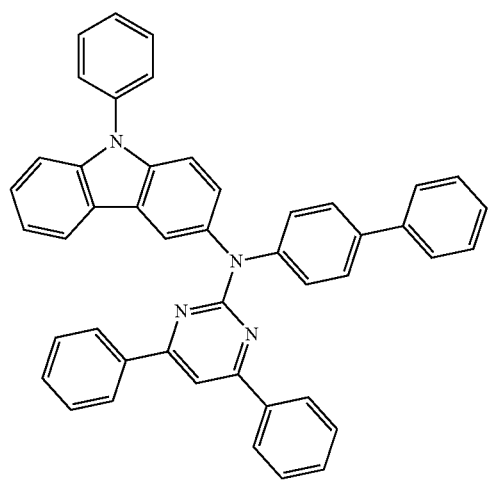
R1
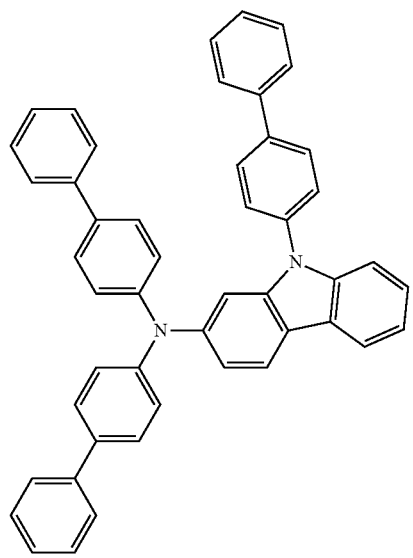
R2

TABLE 1-continued
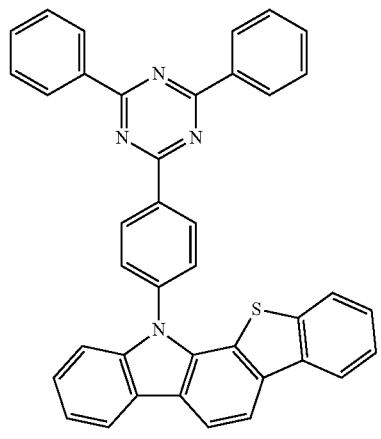
H-67
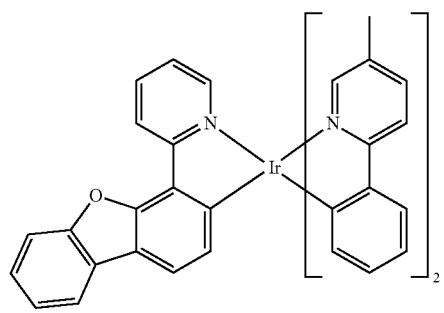
D-50
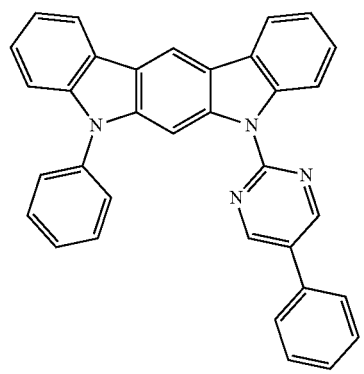
C-81
Electron
Transport Layer/
Electron
Injection Layer
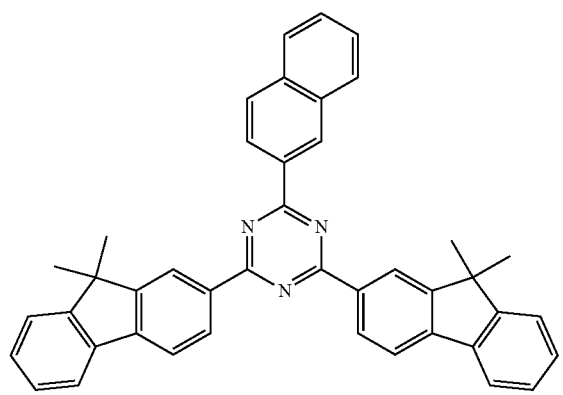
ETL-1

TABLE 1-continued

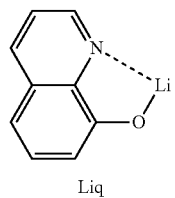

Liq

The HOMO energy level, LUMO energy level, and triplet energy level of compounds C-1, C-81, and R1, as a hole transport host, along with compound H-67, as an electron transport host, which are used in the light-emitting layer of Device Examples 1 and 2, and Comparative Example 1, were measured and are shown in Table 2 below.

TABLE 2

| Compound | Structure | Calculation value B3LYP/6-31g* | | |
|---|---|---|---|---|
| | | HOMO (eV) | LUMO (eV) | Triplet (eV) |
| C-1 | 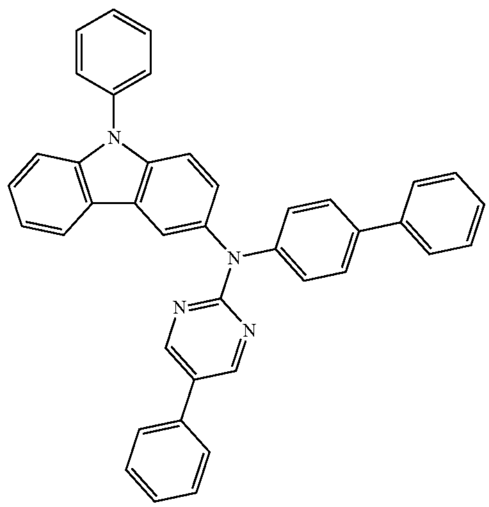 | −5.008 | −0.954 | 2.908 |
| C-81 | 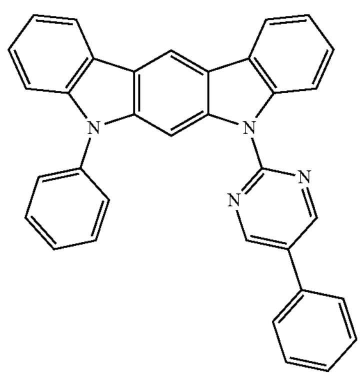 | −5.034 | −1.240 | 2.861 |

TABLE 2-continued

| Compound | Structure | HOMO (eV) | LUMO (eV) | Triplet (eV) |
|---|---|---|---|---|
| R1 | R1 | −5.005 | −1.506 | 2.683 |
| H-67 | H-67 | −5.330 | −1.988 | 2.715 |

In general, as the LUMO energy level of the hole transport host is higher than the LUMO energy level of the electron transport host, and the difference between the LUMO energy of the hole transport host and the LUMO energy of the electron transport host is larger, the exciplex can be smoothly formed without the electron being directly transferred from the hole transport host to the electron transport host. Referring to Table 2 above, it can be confirmed that the difference in LUMO levels between compounds C-1 and H-67, and between compounds C-81 and H-67, which are respectively the host compounds used in Device Examples 1 and 2 according to one embodiment, is greater than the LUMO level difference between R1 and H-67, which are the host compounds used in Comparative Example 1. As a result, in the light-emitting layer of Device Examples 1 and 2, it can be expected that the formation of the exciplex is smooth and the efficiency of the device is superior to that of Comparative Example 1.

The driving voltage, luminous efficiency at a luminance of 1,000 nits, and the results of power efficiency, CIE color coordinates, and the time taken for the light-emission in constant-current to be reduced from 100% to 80% at a luminance of 15,000 nits, of the organic electroluminescent devices produced as above are shown in the following Table 3.

TABLE 3

| | Voltage [V] | Luminous Efficiency [cd/A] | Power Efficiency [lm/W] | Color Coordinates (x, y) | Lifespan T80 [Hr] |
|---|---|---|---|---|---|
| Device Example 1 | 3.0 | 68.0 | 70.3 | 0.316, 0.667 | 150 |
| Device Example 2 | 3.0 | 61.6 | 64.3 | 0.312, 0.673 | 390 |
| Comparative Example 1 | 3.1 | 63.8 | 65.6 | 0.316, 0.668 | 70 |
| Comparative Example 2 | 2.6 | 50.4 | 60.9 | 0.308, 0.674 | 45 |

Referring to Table 3 above, it can be confirmed that Comparative Example 2, including host compound R2, which contains arylamine, in the light-emitting layer, has the lowest luminous efficiency, power efficiency, and lifespan. In addition, Device Examples 1 and 2, which include heteroarylamine as a host in the light-emitting layer, have a substituent at the 5-position of pyrimidine, so that the device according to Device Examples 1 and 2 exhibits excellent driving voltage, high luminous efficiency, and an excellent power efficiency compared with Comparative Example 1, which includes substituents at the 4-position and 6-position of pyrimidine. In particular, it can be confirmed that the lifespan of the Device Examples is at least twice as long as the lifespan of the device according to the Comparative Examples. That is, as mentioned above, at the co-host condition, Device Examples 1 and 2 being more smoothly in the formation of the exciplex have a lower driving voltage and higher luminous efficiency than that of Comparative Example 1, and thereby present excellent lifespan.

In other words, a device using an organic electroluminescent compound according to the present disclosure as a host material for luminescence has excellent luminescence characteristics, and there is an advantage to lowering power consumption, since the voltage used for emitting light of the same luminance is low. Furthermore, the device exhibits improved lifespan characteristics so that it has the advantage of increasing battery usage time in portable display devices where current OLED panels are predominantly used.

The invention claimed is:

1. An organic electroluminescent material, wherein the organic electroluminescent material is a host material, wherein the host material comprises at least one first host compound and at least one second host compound, and wherein the first host compound is represented by formula 2:

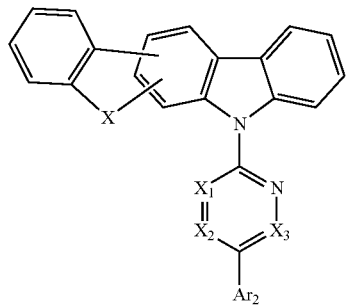

(2)

wherein,
X represents O, S, or $NR_4$;
$X_1$ to $X_3$ each independently represent N or CH;
$Ar_2$ represents a substituted or unsubstituted (C6-C30)aryl or a substituted or unsubstituted (3- to 30-membered) heteroaryl; and
$R_4$ represents hydrogen, deuterium, halogen, cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di- (C6-C30)arylamino; or may be linked to an adjacent substituent to form a substituted or unsubstituted (C3-C30) mono- or polycyclic, alicyclic or aromatic ring wherein the second host compound is represented by the following formula 3:

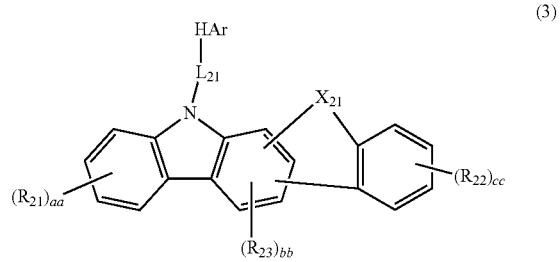

(3)

wherein,
HAr represents a substituted or unsubstituted (5- to 30-membered) heteroaryl;
$L_{21}$ represents a single bond, a substituted or unsubstituted (C6-C30) arylene, or a substituted or unsubstituted (5- to 30-membered) heteroarylene;
$X_{21}$ represents O or S;
$R_{21}$ to $R_{23}$ each independently represent hydrogen, deuterium, halogen, cyano, a substituted or unsubstituted (C1-C30)alkyl, a substituted or unsubstituted (C6-C30)aryl, a substituted or unsubstituted (5- to 30-membered) heteroaryl, a substituted or unsubstituted (C6-30)ar(C1-C30)alkyl, a substituted or unsubstituted (C3-C30) cycloalkyl, a substituted or unsubstituted (C1-C30) alkoxy, a substituted or unsubstituted (C1-C30) alkylsilyl, a substituted or unsubstituted (C6-C30) arylsilyl, a substituted or unsubstituted (C6-C30)ar(C1-C30) alkylsilyl, a substituted or unsubstituted (C1-C30) alkylamino, a substituted or unsubstituted (C6-C30) arylamino, or a substituted or unsubstituted (C1-C30) alkyl(C6-C30)arylamino; or may be linked to an adjacent substituent to form (C3-C30) mono- or polycyclic, alicyclic or aromatic ring; and
aa and cc each independently represent an integer from 1 to 4, and bb represents an integer of 1 or 2.

2. The organic electroluminescent material according to claim 1, wherein the compound represented by formula 2 is selected from the following compounds:

C-47

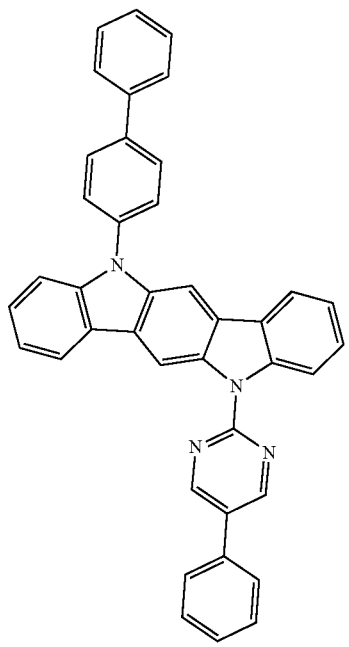

-continued
C-48
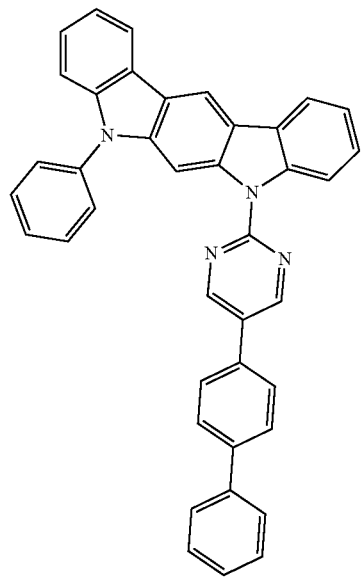
C-49
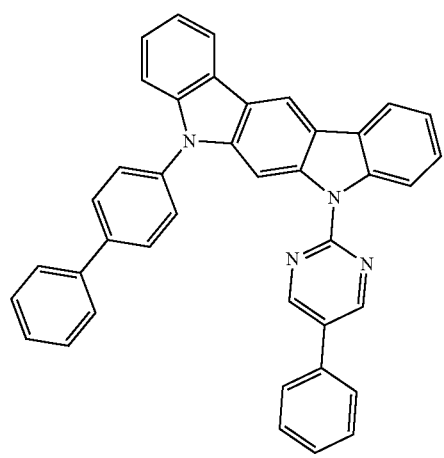
C-50
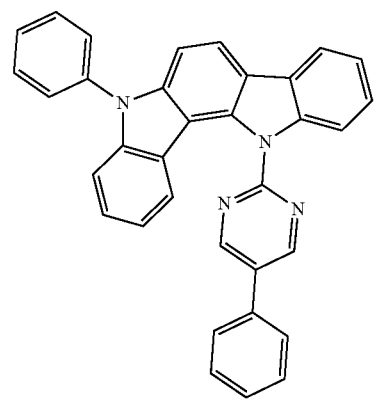
-continued
C-51
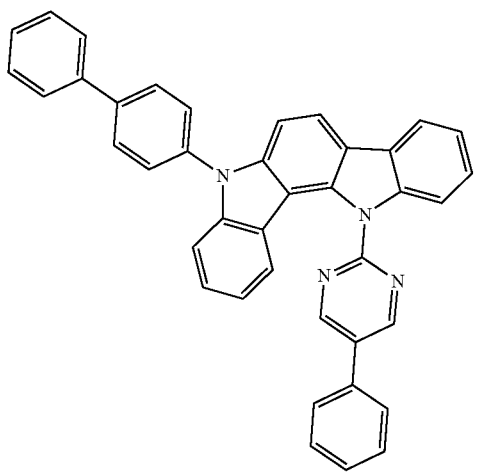
C-52
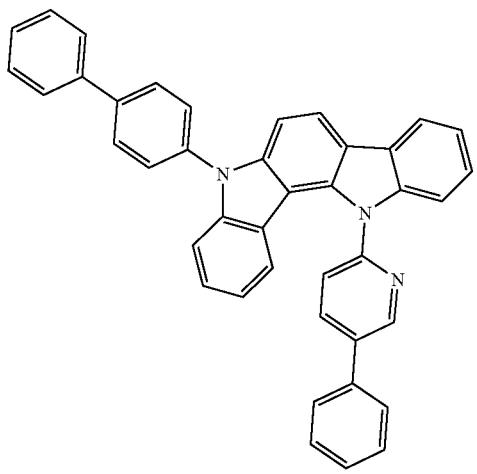
C-53
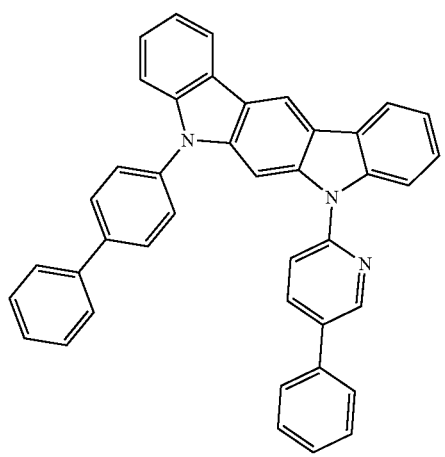

-continued
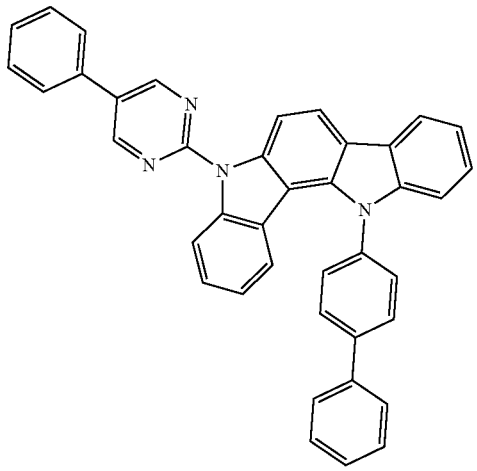
C-54
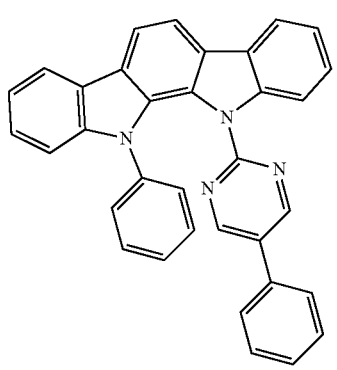
C-55
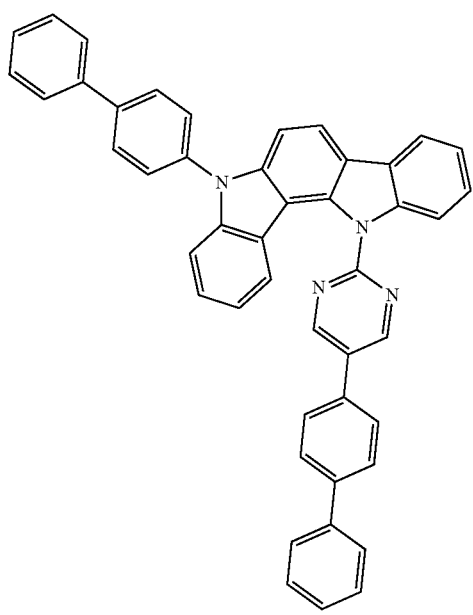
C-56
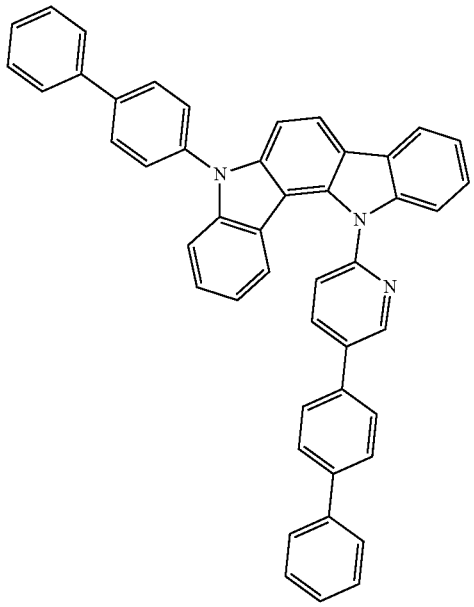
C-57
-continued
C-58
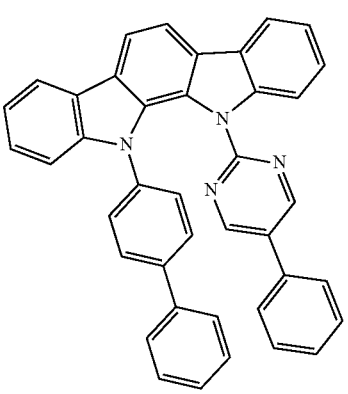
C-61

-continued
C-62
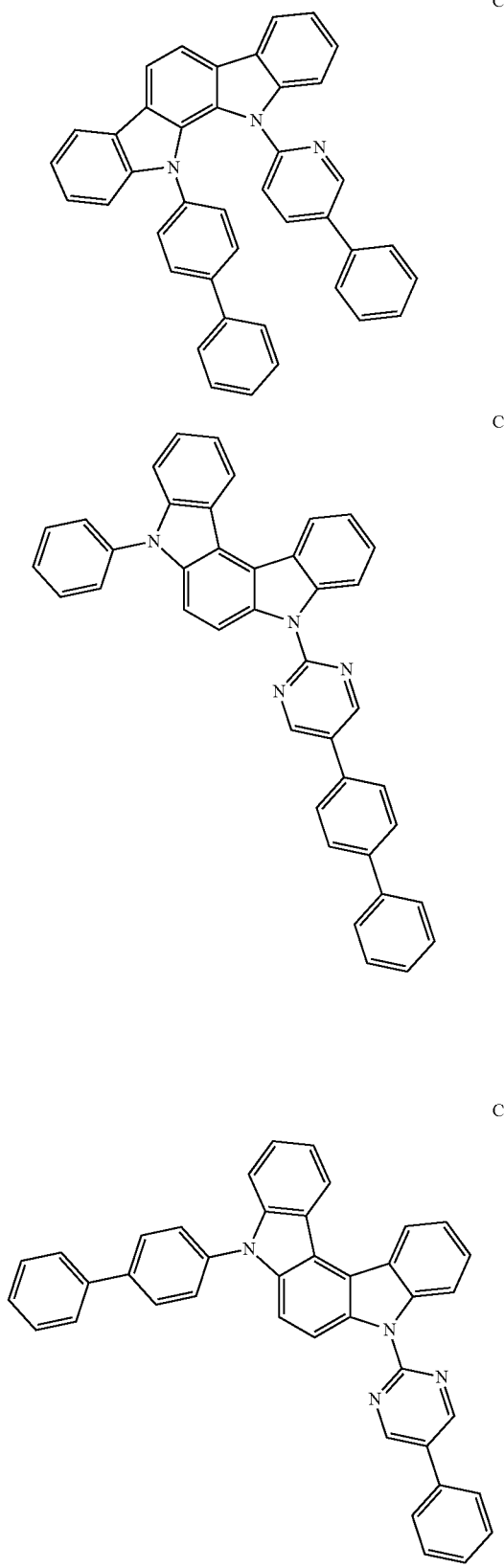
C-64
C-65
-continued
C-81
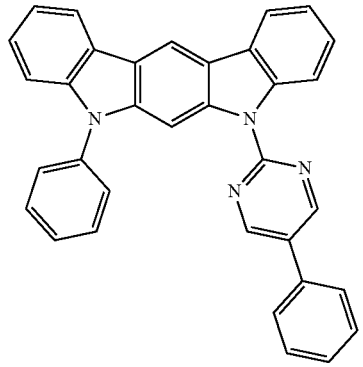
C-82
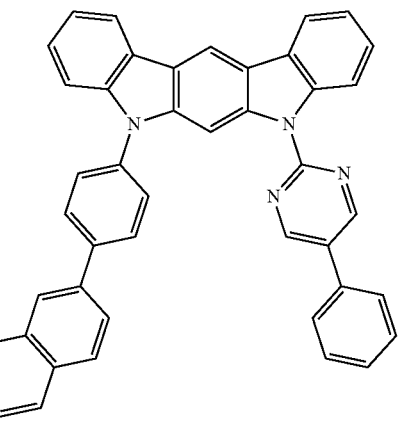
C-83
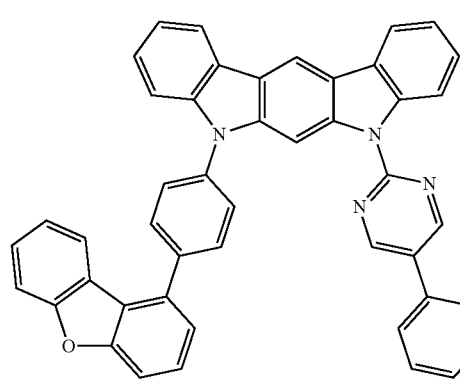
and
C-84
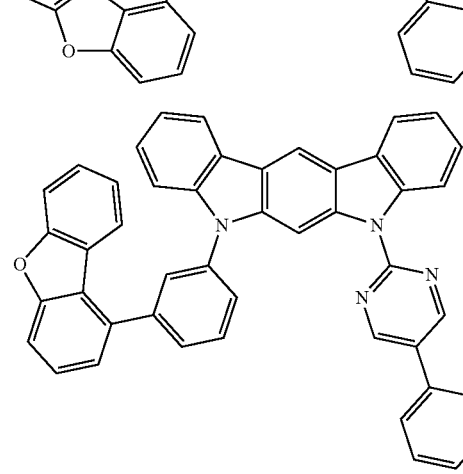
.
3. An organic electroluminescent device comprising the organic electroluminescent material according to claim 1.
* * * * *